United States Patent [19]

Fraser et al.

[11] Patent Number: 4,870,023

[45] Date of Patent: Sep. 26, 1989

[54] RECOMBINANT BACULOVIRUS OCCLUSION BODIES IN VACCINES AND BIOLOGICAL INSECTICIDES

[75] Inventors: Malcolm J. Fraser; Elliot D. Rosen; Victoria A. Ploplis, all of South Bend, Ind.

[73] Assignee: American Biogenetic Sciences, Inc., Copiague, N.Y.

[21] Appl. No.: 153,736

[22] Filed: Feb. 8, 1988

Related U.S. Application Data

[63] Continuation-in-part of Ser. No. 26,498, Mar. 16, 1987, abandoned, which is a continuation-in-part of Ser. No. 26,499, Mar. 16, 1987.

[51] Int. Cl.$^4$ .................. C12N 7/00; C12N 15/00; C12N 1/00; C12P 21/00
[52] U.S. Cl. ........................... 435/320; 435/68; 435/91; 435/172.3; 435/235; 435/243; 536/27; 935/32; 935/57; 935/70; 530/350; 530/820; 530/826
[58] Field of Search ............... 435/68, 70, 91, 172.3, 435/235, 317.1, 320, 240, 243, 240.25, 240.1, 242.2, 241, 253; 536/27; 935/34, 56, 57, 70, 32, 27; 530/820, 826, 350, 351

[56] References Cited

U.S. PATENT DOCUMENTS 4,722,849 2/1988 Valenzuela et al.
4,745,051 5/1988 Smith et al. ........................... 435/68

OTHER PUBLICATIONS

Carstens et al. (1987) J. Gen. Vir., 68: 901-5.
Smith et al. (1981), J. Virology, 39: 125-37.
Kuroda et al. (1986), EMBO J., 5: 1359-65.
Harrap, 1972, Virology, 50: 124-132.
Engstrom, 1974, Biochem. Exp. Biol., 11: 7.
Epstein et al., 1977, Biochem. J., 167: 321-332.
Rohrmann et al., 1977, Biochemistry, 16: 1634.
Maruniak et al., 1978, J. Invert. Pathol., 32: 196-201.
Tinsley, T. and Harrap, K., 1978, "Comprehensive Virology", vol. 12, pp. 1-101, H. Fraenkel-Conrat and R. Wagner, Eds., Plenum Press, NY.
Scharnhorst, D. and Weaver, R., 1980, Virology, 102: 468-472.
McIntosh et al., 1981, J. Invert. Pathol., 37: 258-264.
Tweeten et al., 1981, Microbiological Rev., 45: 379-408.
Duncan et al., 1983, J. Gen. Virology, 64: 1531-1542.
Tjia et al., 1979, Virology, 99: 399-409.
Rohrmann et al., 1981, J. Mol. Evol., 17: 329-333.
Vlak et al., 1981, J. Virology, 40: 1531-1542.
Adang et al., 1982, J. Virology, 44: 782-793.
Smith, G. and Summers, M., 1982, Virology, 123: 393-406.
Vlak et al., 1982, Virology, 123: 222-228.
Erlandson et al., 1983, Virology, 126: 398-402.
Smith et al., 1983, J. Virology, 45: 215-225.
Smith et al., 1983, J. Virology, 46: 584-593.
Knell & Summers, 1984, J. Gen. Virology, 65: 445-450.
Heng et al., 1985, Scientia Sinica, pp. 1051-1059.
Leisy et al., 1986, Virology, 153: 280-288.
Miller, L. K., 1981, Genetic Engineering in Plant Sciences, Praeger Publishers, New York, pp. 203-224.
Smith et al., 1983, Mol. Cell. Biol., 3: 2156-2165.
Maeda et al., 1984, Proc. Japan Acad., 60: 423-426.
Pennock et al., 1984, Mol. Cell. Biol., 4: 399-406.
Carbonell et al., 1985, J. Virology, 56: 153-160.

(List continued on next page.)

*Primary Examiner*—Thomas G. Wiseman
*Assistant Examiner*—Stephanie Seidman
*Attorney, Agent, or Firm*—Pennie & Edmonds

[57] ABSTRACT

The present invention is directed to recombinant baculoviruses which encode fusion polyhedrin proteins capable of forming occlusion bodies containing foreign peptides. The recombinant baculoviruses of the invention are formed by insertion into or replacement of regions of the polyhedrin gene that are not essential for occlusion body formation, with foreign DNA fragments by recombinant DNA techniques. The recombinant occlusion bodies produced in accordance with the present invention have uses in vaccine formulations, immunoassays, immobilized enzyme reactions, as biological insecticides, and as expression vectors.

51 Claims, 26 Drawing Sheets

OTHER PUBLICATIONS

Maeda et al., 1985, Nature, 315: 592–594.
Miyamoto et al., 1985, Mol. Cell. Biol., 5: 2860–2865.
Summers, M. D. and Smith, G., 1985, Genetic Engineering of Baculoviruses, Genetically Altered Viruses and the Environment; Meeting, Cold Spring Harbor, N.Y., Apr. 28–May 1, 1985, pp. 319–331.
Matsura et al., 1986, J. Gen. Virol., 67: 1515–1529.
Possee, 1986, Virus Research, 5: 43–59.
Estes et al., 1987, J. Virology, 61: 1488–1494.
Hu et al., 1987, J. Virology, 61: 3617–3620.
Inumaru et al., 1987, J. Gen. Virol., 68: 1627–1635.
Jeang et al., 1987, J. Virology, 61: 1761–1764.
Matsuura et al., 1987, J. Gen. Virology, 68: 1233–1250.
Rice et al., 1987, J. Virology, 61: 1712–1716.
Luckow et al., 1988, Biotechnology, 6: 47–55.
Hohmann et al., 1983, Virology, 125: 432–444.
Quant et al., 1984, Applied and Environmental Microbiology, 48: 732'736.
Huang et al., 1985, Virology, 143: 380–391.
Steeves et al., 1974, J. Virology, 14: 187–189.
Dalyrample et al., 1981, in "The Replication of Negative Strand Viruses", ed. Bishop, D. and Compans., R., Elseveir North Holland Publishers, N.Y., pp. 167–172.
Massey et al., 1981, Virology, 115: 20–32.
Gonzalez-Scarano et al., 1982, Virology, 120: 42–53.
Mathews et al., 1982, J. Immunol., 129: 2763–2767.
Matsuno et al., 1983, Infection and Immunity, 39: 155–158.
Warren, 1985, "Vaccines", 85, Lerner, R. et al., Eds., Cold Spring Harbor Laboratory, New York, pp. 373–376.
Granoff et al., 1986, J. Infect. Dis., 153: 448–461.
European Patent Application #0 127 839, Smith et al., Application No. 84105841.5, published Dec. 12, 1984.

```
                    -150
         TGCAAGAATATGAAGATTTCTGTCGTCGTGTTGAAAATTTGTAATAAAACTAAATAAACCTTTAATATAA
-80
ATATTAAACATACACTTTTATTTCTAAAATAAGTATTTTTTTCCTATTGTTCAAGATTGTGAAAAATCAAATATCCCATA met tyr thr arg tyr ser tyr ser pro thr leu glu lys thr tyr val tyr asp asn lys
   ATG TAT ACT CGT TAC AGT TAC AGC CCT ACT TTG GGC AAA ACC TAT GTG TAC GAC AAC AAA
   1   AccI                                                        KsoI tyr phe lys asn leu glu ala val ile lys asn ala lys arg lys lys his leu glu glu
   TAC TTT AAG AAT TTA GGT GCT GTT ATT AAA AAT GCC AAA CGC AAG AAG CAT TTA GAG GAG
   61                                                                      MnlI
                                                                            HgiAI/SduI
   his glu his glu gly arg asn leu asp ser leu asp lys tyr leu val ala glu asp pro
   CAC GAA CAT GAA GGA CGC AAC TTG GAT TCG CTC GAC AAA TAC TTG GTG GCG GAA GAT CCT
   121      NlaIII MoeII            HinfI    TaqI phe leu gly pro gly lys asn gln lys leu thr leu phe lys glu ile arg ser val lys
   TTT TTG GGA CCT GGC AAA AAT CAA AAA CTA ACT TTG TTT AAA GAG ATT CGC AGC GTT AAG
   181             pHH5 pro asp thr met lys leu val val asn trp ser gly arg glu phe leu arg glu thr trp
   CCC GAC ACA ATG AAG CTT GTA GTT AAC TGG AGC GGT CGC GAA TTT CTT CGC GAA ACT TGG
   241                 HindIII    HindII          NruI            NruI thr arg phe met glu asp ser phe pro ile val asn asp gln glu ile met asp val phe
   ACT CGT TTC ATG GAA GAC AGT TTT CCC ATT GTA AAC GAC CAA GAA ATT ATG GAC GTG TTT
   301 leu ser val asn met arg pro thr lys pro asn arg cys tyr arg phe leu ala gln his
   CTG TCT GTT AAT ATG CGA CCA ACC AAA CCG AAC CGT TGT TAC CGA TTC TTA GCG CAA CAC
   361 ala leu ala cys asp pro asp tyr ile pro his glu val ile arg ile val glu pro ser
   GCT CTG GCT TGT GAT CCC GAC TAT ATT CCT CAC GAA GTC ATT CGT ATT GTA GAA CCT TCC
   421 tyr val gly ser asn asn glu tyr arg ile ser leu ala lys lys tyr gly gly cys pro
   TAT GTA GGC AGT AAC AAC GAG TAC AGA ATT AGT TTA GCC AAA AAA TAC GGC GGT TGC  CCC
   481 val met asn leu his ala glu tyr thr asn ser phe glu asp phe ile thr asn val ile
   GTT ATG AAT TTG CAC GCT GAA TAC ACT AAT TCC TTT GAA GAT TTC ATT ACC AAC GTA ATT
   541 trp glu asn asn tyr lys pro ile val tyr val gly thr asp ser ala glu glu glu glu
   TGG GAG AAC TTC TAC AAA CCA ATT GTT TAC GTA GGC ACT GAT TCT GCC GAA GAA GAG GAA
   601 ile leu leu glu val ser leu ile phe lys ile lys glu phe ala pro ala pro leu tyr
   ATA CTC CTA GAG GTT TCT TTG ATA TTT AAG ATC AAA GAA TTT GCA CCT GCG CCG CTA TAC
   661 thr gly pro ala tyr stop
   ACT GGT CCT GCA TAT TAA ACTTGCGATTCAGT
   721
```

FIG. 1

FIG. 1A
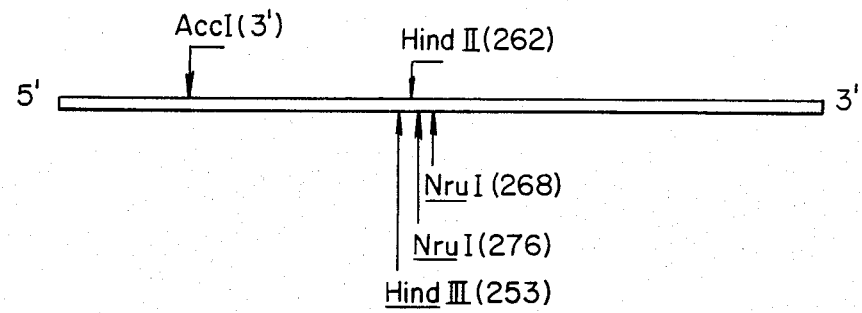
FIG. 1B
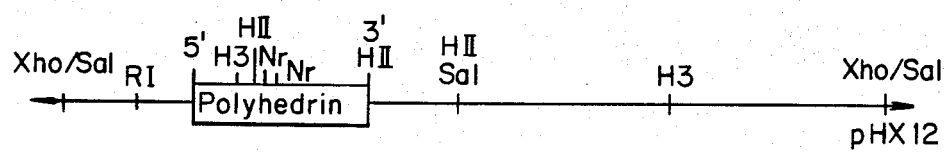
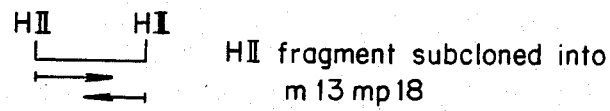
HII fragment subcloned into m13mp18
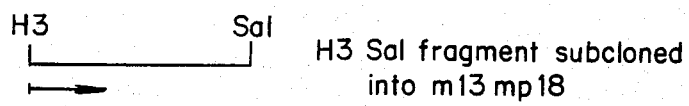
H3 Sal fragment subcloned into m13mp18
RI-H3 fragment subcloned into m13mp18
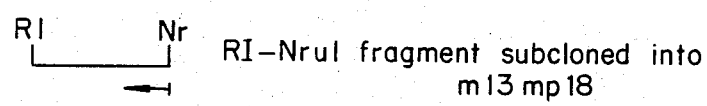
RI-NruI fragment subcloned into m13mp18
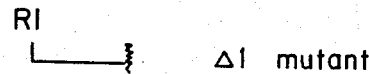
Δ1 mutant

|  |  | ATG | CCG | GAT | TAT | TCA | TAC | CGT | CCC | ACC | ATC | GGG | CGT | ACC | TAC | GTG | TAC | GAC | AAC | AAG |
|---|---|---|---|---|---|---|---|---|---|---|---|---|---|---|---|---|---|---|---|---|
| A.c. |  | Met | --- | Pro | Asp | Tyr | Ser | Tyr | Arg | Pro | Thr | Ile | Gly | Arg | Thr | Tyr | Val | Tyr | Asp | Asn | Lys |
| H.z. | 1 |  | Tyr | Thr | Arg |  |  |  | Ser |  |  | Leu |  | Lys |  |  |  |  |  |  |  |
| B.m. |  |  |  |  | Asn |  |  |  | Asn |  |  |  |  |  |  |  |  |  |  |  |  |

|  |  | TAC | TAC | AAA | AAT | TTA | GGT | GCC | GTT | ATC | AAG | AAC | GCT | AAG | CGC | AAG | AAG | CAC | TTC | GCC | GAA |
|---|---|---|---|---|---|---|---|---|---|---|---|---|---|---|---|---|---|---|---|---|---|
| A.c. |  | Tyr | Tyr | Lys | Asn | Leu | Gly | Ala | Val | Ile | Lys | Asn | Ala | Lys | Arg | Lys | Lys | His | Phe | Ala | Glu |
| H.z. | 21 |  | Phe |  |  |  |  |  |  |  |  |  |  |  |  |  |  |  | Leu | Glu |  |
| B.m. |  |  |  |  |  |  | Gly | Leu |  |  |  |  |  |  |  |  |  |  | Leu | Ile |  |

*BamHI*

|  |  | CAT | GAG | ATC | GAA | GAG | GCT | ACC | CTC | GAC | CCC | CTA | GAC | AAC | TAC | CTA | GTG | GCT | GAG | GAT | CCT |
|---|---|---|---|---|---|---|---|---|---|---|---|---|---|---|---|---|---|---|---|---|---|
| A.c. |  | His | Glu | Ile | Glu | Glu | Ala | Thr | Leu | Asp | Pro | Leu | Asp | Asn | Tyr | Leu | Val | Ala | Glu | Asp | Pro |
| H.z. | 41 |  |  | His |  |  |  | Arg | Asn |  | Ser |  |  | Lys |  |  |  |  |  |  |  |
| B.m. |  | Glu | His | Lys |  |  |  | Lys | Gln | Trp | Leu |  |  |  |  |  | Met |  |  |  |  |

|  |  | TTC | CTG | GGA | CCC | GGC | AAG | AAC | CAA | AAA | CTC | ACT | CTC | TTC | AAG | GAA | ATC | CGT | AAT | GTT | AAA |
|---|---|---|---|---|---|---|---|---|---|---|---|---|---|---|---|---|---|---|---|---|---|
| A.c. |  | Phe | Leu | Gly | Pro | Gly | Lys | Asn | Gln | Lys | Leu | Thr | Leu | Phe | Lys | Glu | Ile | Arg | Asn | Val | Lys |
| H.z. | 61 |  |  |  |  |  |  |  |  |  |  |  |  |  |  |  |  |  |  | Val |  |
| B.m. |  |  |  |  |  |  |  |  |  |  |  |  |  |  |  |  |  |  |  |  |  |

|  |  | CCC | GAC | ACG | ATG | AAG | CTT | GTC | GTT | GGA | TGG | AAA | GGA | AAA | GAG | TTC | TAC | AGG | GAA | ACT | TGG |
|---|---|---|---|---|---|---|---|---|---|---|---|---|---|---|---|---|---|---|---|---|---|
| A.c. |  | Pro | Asp | Thr | Met | Lys | Leu | Val | Val | Gly | Trp | Lys | Gly | Lys | Glu | Phe | Tyr | Arg | Glu | Thr | Trp |
| H.z. | 81 |  |  |  |  |  |  |  | Ile |  |  | Asn |  | Ser |  |  | Arg |  | Leu |  |  |
| B.m. |  |  |  |  |  |  |  |  |  |  |  | Asn |  | Ser |  |  |  |  | Leu |  |  |

|  |  | ACC | CGC | TTC | ATG | GAA | GAC | AGC | TTC | CCC | ATT | GTT | AAC | GAC | CAA | GAA | --- | GTG | ATG | GAT | GTT |
|---|---|---|---|---|---|---|---|---|---|---|---|---|---|---|---|---|---|---|---|---|---|
| A.c. |  | Thr | Arg | Phe | Met | Glu | Asp | Ser | Phe | Pro | Ile | Val | Asn | Asp | Gln | Glu | --- | Val | Met | Asp | Val |
| H.z. | 101 |  |  |  |  |  |  |  |  |  |  |  |  |  |  |  | --- |  | Ile |  |  |
| B.m. |  |  |  | Val |  |  |  |  |  |  |  |  |  |  |  |  |  | Val |  |  |  |

|  |  | TTC | CTT | GTT | GTC | AAC | ATG | CGT | CCC | ACT | AGA | CCC | AAC | CGT | TGT | TAC | AAA | TTC | CTG | GCC | CAA |
|---|---|---|---|---|---|---|---|---|---|---|---|---|---|---|---|---|---|---|---|---|---|
| A.c. |  | Phe | Leu | Val | Val | Asn | Met | Arg | Pro | Thr | Arg | Pro | Asn | Arg | Cys | Tyr | Lys | Phe | Leu | Ala | Gln |
| H.z. | 120 |  |  | Ser |  |  |  |  |  |  | Lys |  |  |  |  |  | Arg |  |  |  |  |
| B.m. |  | Tyr |  |  |  | Ala |  | Leu | Lys |  |  |  |  |  |  |  |  |  |  |  |  |

|  |  | CAC | GCT | CTG | CGT | TGC | GAC | CCC | GAC | TAT | GTA | CCT | CAT | GAC | GTG | ATT | AGG | ATC | GTC | GAG | CCT |
|---|---|---|---|---|---|---|---|---|---|---|---|---|---|---|---|---|---|---|---|---|---|
| A.c. |  | His | Ala | Leu | Arg | Cys | Asp | Pro | Asp | Tyr | Val | Pro | His | Asp | Val | Ile | Arg | Ile | Val | Glu | Pro |
| H.z. | 140 |  |  |  | Ala |  |  |  |  |  |  |  |  |  |  |  |  |  |  | Met |  |
| B.m. |  |  |  |  | --- | Gln | Asn |  |  |  | Ile |  |  | Glu |  |  |  |  |  |  |  |

|  |  | TCA | TGG | GTG | GGC | AGC | AAC | AAC | GAG | TAC | CGC | ATC | AGC | CTG | GCT | AAG | AAG | GGC | GGC | GGC | TGC |
|---|---|---|---|---|---|---|---|---|---|---|---|---|---|---|---|---|---|---|---|---|---|
| A.c. |  | Ser | Trp | Val | Gly | Ser | Asn | Asn | Glu | Tyr | Arg | Ile | Ser | Leu | Ala | Lys | Lys | Gly | Gly | Gly | Cys |
| H.z. | 160 |  |  | Tyr |  |  |  |  |  |  |  |  |  |  |  |  |  |  | Tyr |  |  |
| B.m. |  |  |  | Tyr |  |  | Met |  |  |  |  |  |  |  |  |  |  |  |  |  |  |

|  |  | CCA | ATA | ATG | AAC | CTT | CAC | TCT | GAG | TAC | ACC | AAC | TCG | TTC | GAA | CAG | TTC | ATC | GAT | CGT | GTC |
|---|---|---|---|---|---|---|---|---|---|---|---|---|---|---|---|---|---|---|---|---|---|
| A.c. |  | Pro | Ile | Met | Asn | Leu | His | Ser | Glu | Tyr | Thr | Asn | Ser | Phe | Glu | Gln | Phe | Ile | Asp | Arg | Val |
| H.z. | 180 |  | Val |  |  |  |  |  |  | Ala |  |  |  |  |  | Asp |  |  | Thr | Asn |  |
| B.m. |  |  |  |  |  | Ile |  |  |  |  |  |  |  |  |  | Ser |  | Val | Asn |  |  |

*KpnI*

|  |  | ATC | TGG | GAG | AAC | TTC | TAC | AAG | CCC | ATC | GTT | TAC | ATC | GGT ACC | GAC | TCT | GCT | GAA | GAG | GAG |
|---|---|---|---|---|---|---|---|---|---|---|---|---|---|---|---|---|---|---|---|---|
| A.c. |  | Ile | Trp | Glu | Asn | Phe | Tyr | Lys | Pro | Ile | Val | Tyr | Ile | Gly Thr | Asp | Ser | Ala | Glu | Glu | Glu |
| H.z. | 200 |  |  |  |  |  |  |  |  |  |  |  | Val |  |  |  | Ala | Ser |  |  |
| B.m. |  |  |  |  |  |  |  |  |  |  |  |  |  |  |  |  |  |  |  |  |

|  |  | GAA | ATT | CTC | CTT | GAA | GTT | TCC | CTG | GTG | TTC | AAA | GTA | AAG | GAG | TTT | GCA | CCA | GAC | GCA | CCT |
|---|---|---|---|---|---|---|---|---|---|---|---|---|---|---|---|---|---|---|---|---|---|
| A.c. |  | Glu | Ile | Leu | Leu | Glu | Val | Ser | Leu | Val | Phe | Lys | Val | Lys | Glu | Phe | Ala | Pro | Asp | Ala | Pro |
| H.z. | 220 |  |  |  |  |  |  |  |  | Ile |  | Ile |  |  |  |  |  |  |  | --- |  |
| B.m. |  | Gln |  | Ile |  |  |  |  |  | Ile |  | Ile |  |  |  |  |  |  |  |  |  |

|  |  | CTG | TTC | ACT | GGT | CCG | GCG | TAT |
|---|---|---|---|---|---|---|---|---|
| A.c. |  | Leu | Phe | Thr | Gly | Pro | Ala | Tyr |
| H.z. | 239 |  | Tyr |  |  |  |  |  |
| B.m. |  |  |  |  |  |  |  |  |

*FIG. 2*

```
                met pro asp tyr ser tyr arg pro thr ile
5'-AATTCGC ATG CCG GAT TAT TCA TAC CGT CCC ACG ATC
3'-        GCG TAC GGC CTA ATA AGT ATG GCA GGG TGC TAG
  Eco RI Sph I                                   Pvu I gly arg thr tyr val tyr asp asn lys tyr
           GGG CGT ACC TAC GTG TAC GAC AAC AAG TAC
           CCC GCA TGG ATG CAC ATG CTG TTG TTC ATG
                                               Sca I tyr lys asn leu gly ala val ile lys asn
           TAC AAA AAT TTA GGT GCC GTG ATC AAG AAC
           ATG TTT TTA AAT CCA CGG CAC TAG TTC TTG
                                       Bcl I ala lys arg lys lys his phe ala glu his
           GCT AAG CGC AAG AAG CAC TTC GCC GAA CAT
           CGA TTC GCG TTC TTC GTG AAG CGG CTT GTA glu ile glu glu ala thr leu asp pro leu
           GAG ATC GAA GAG GCT ACT CTA GAC CCC CTA
           CTC TAG CTT CTC CGA TGA GAT CTG GGG GAT
                                       Xba I asp asn tyr leu val ala glu asp
           GAC AAC TAC CTA GTG GCT GAG              -3'
           CTG TTG ATG GAT CAC CGA CTC CTA G        -5'
                                       Bam HI
```

FIG. 4

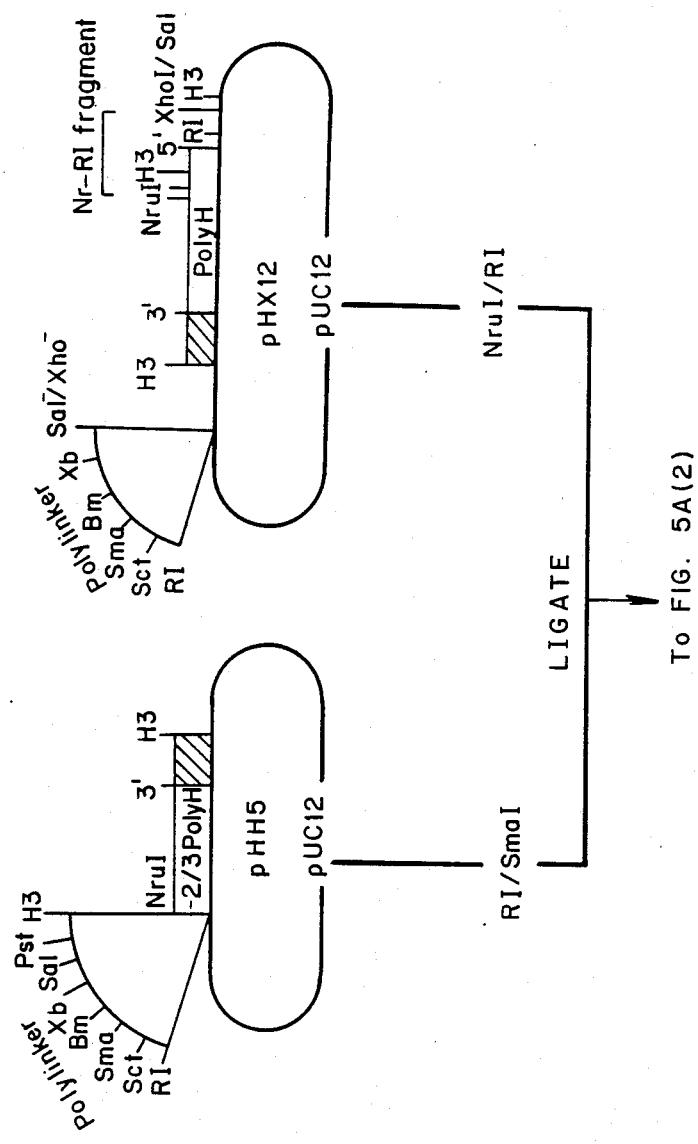
FIG. 5A(1)

FIG. 5A(2)
From FIG. 5A(1)
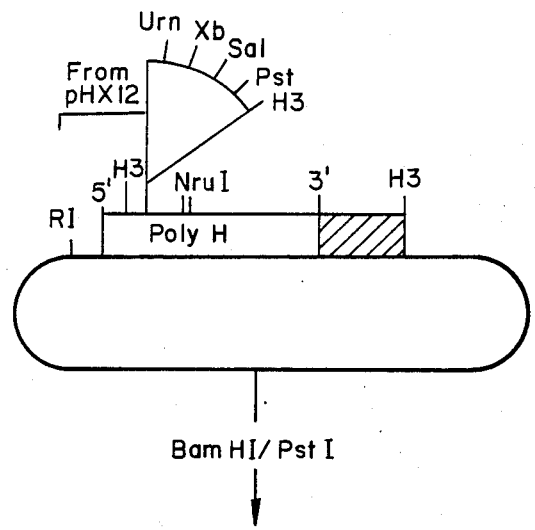
Bam HI/Pst I
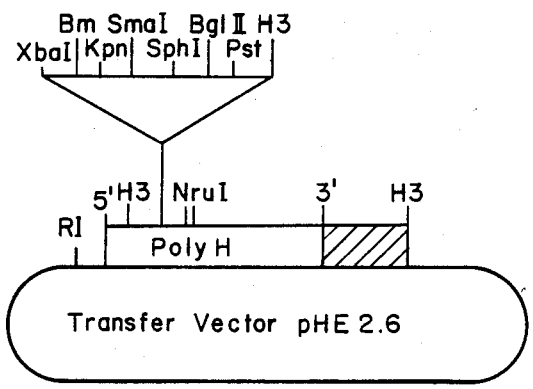
Transfer Vector pHE 2.6

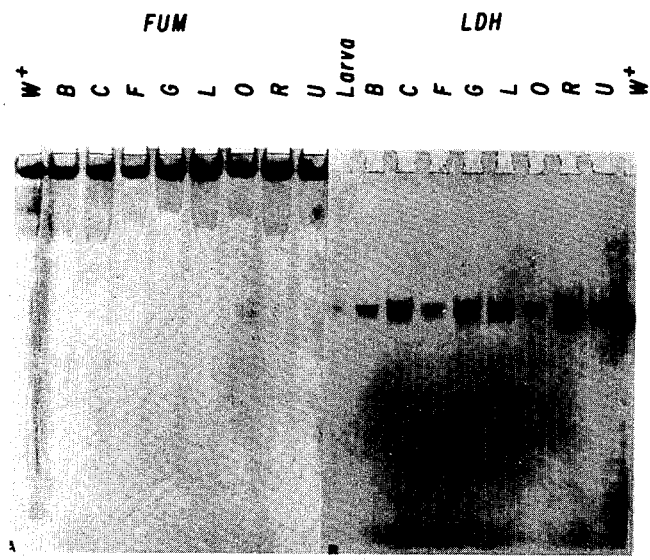
FIG. 11

FIG. 15
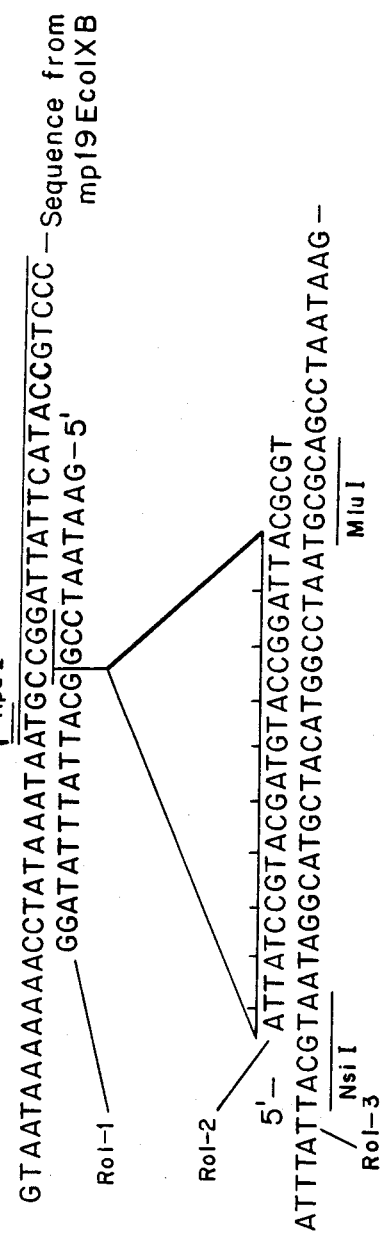
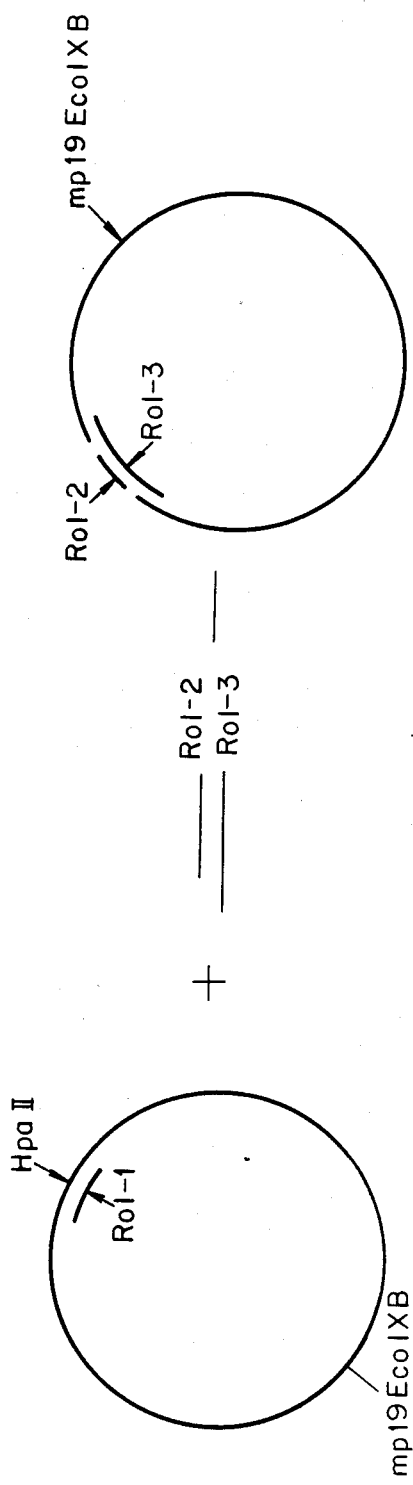

FIG. 16A pEcol — RI, X, B, K, B, RI

Clone 2kb Xho/Bam fragment into mp19 Sal/Bam mp19 Xho/Bam — P, B

Use CREC5 Oligo for in vitro mutagenesis

TRANSFER VECTOR pAV11 — B, K wt Polyhedrin seq
```
                         BglII
AAGAAGCACTTCGCCGAACATGAGATCGAAGAGGCTACCCTCGACCCC...
Crec5  3'—CGGCTTGTACTCTAGATTCTCCGATGGGAG  5'
```
cut with Pst, Bam Crec 5mp19 Xho/Bam — P, Bgl,B Clone Pst/Bam fragment into pAV11 to Construct pAV15 → pAV15 — P, Bgl,B, K cut with BglII and Bam
Insert oligo

```
GATCTATCCGTACGATGTACCGGATTACGCTCTAGACAACTACCTAGTGGCTGAG
    ATAGGCATGCTACATGGCCTAATGCGAGATCTGTTGATGGATCACCGACTCCTAG
```

INFLUENZA EPITOPE | POLYHEDRIN AA 51–58 pAV15 In^hem — P, Bgl, Xba, B, K

FIG. 17A
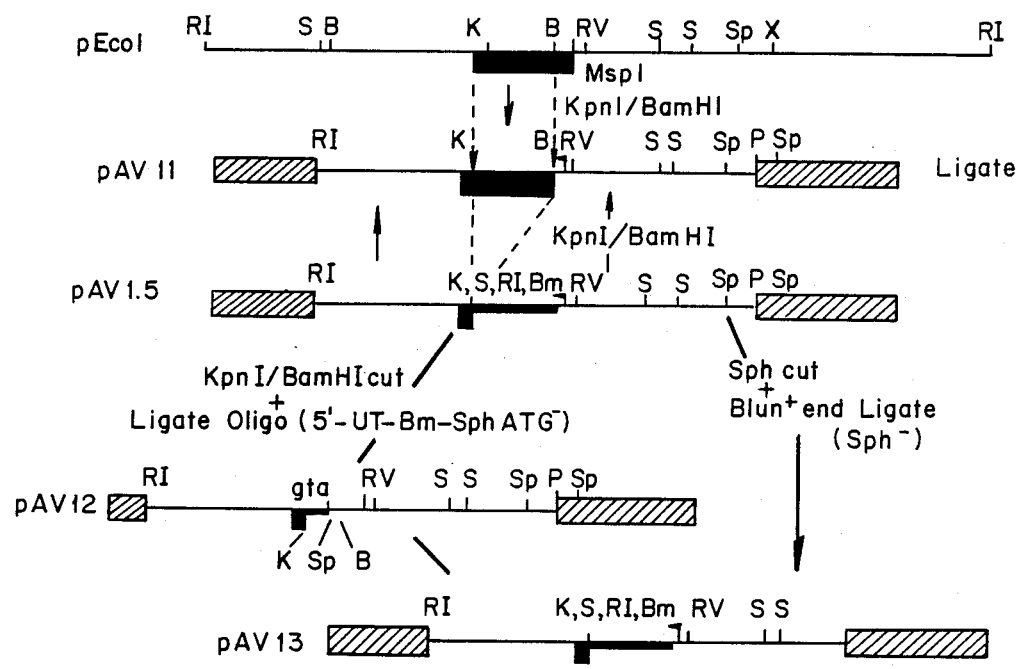
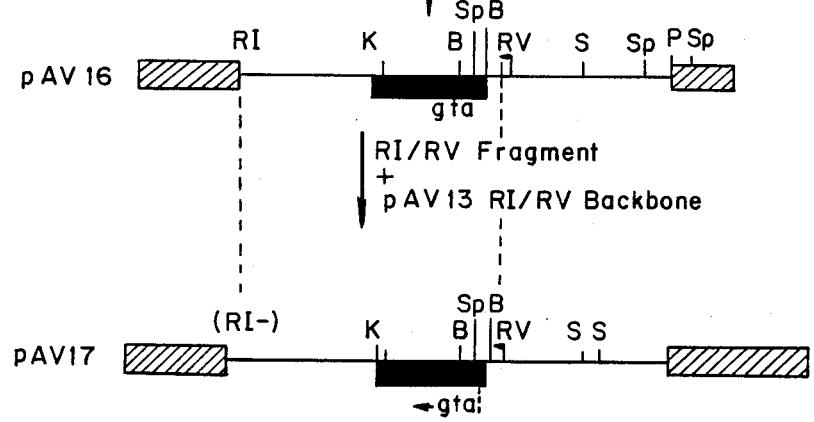

RECOMBINANT BACULOVIRUS OCCLUSION BODIES IN VACCINES AND BIOLOGICAL INSECTICIDES

The present application is a continuation-in-part of copending application Ser. No. 026,498 filed Dec. 16, 1987, by Fraser et al., now abandoned and Ser. No. 026,499 filed Dec. 16, 1987 by Fraser et al., each of which is incorporated by reference herein.

Introduction
Background of the Invention
    Insect Viruses and Occlusion Bodies
    Polyhedrin
    Recombinant DNA Techniques and Baculovirus
Vaccines for viral Infections
Vaccines for Parasitic and Bacterial Infections
Summary of the Invention
    Definitions
Description of the Figures
Detailed Description of the Invention
    The Generation of Recombinant Occlusion Bodies Containing Antigenic Determinants of Heterologous Proteins
        Identification of Modifiable Domains Encoded by the Polyhedrin Gene
        Hydrophilicity Analysis of Polyhedrin
        Sequence Comparisons of Different Polyhedrin Genes
        Sequence Analysis of Polyhedrin Genes Encoding Mutant or Truncated Polyhedrin Proteins
        Structural Analysis of Polyhedrin Amino Acid Sequences
        Preparation and Characterization of Monoclonal Antibodies to Occlusion Bodies
            Identification of Epitopes Recognized by Anti-Polyhedrin Monoclonal Antibodies
        Identification and Characterization of Immunodominant Peptides for Expression on or Within Recombinant Occlusion Bodies
        Construction of Recombinant Polyhedrin Genes
        Selection of Recombinant Occlusion Bodies
        Verification of Expression of Foreign Epitopes on or Within the Recombinant Occlusion Body Vector/Host Systems
        Hosts used in the Vector/Host Systems Insect Cell Lines Larva Hosts
        Expression in Other Microorganisms
    Determination of the Immunopotenoy of Foreign Epitopes Expressed on or Within Recombinant Occlusion Bodies
    Uses of Recombinant Occlusion Bodies
        Vaccines
            Uses of Antibodies Generated by Immunization with Recombinant Occlusion Bodies Biological Insecticides Expression Vectors Immunoassays Immobilized Enzymes
Example: Construction of Transfer Vectors Used for Introducing Foreign Gene Sequences Into the Heliothis Polyhedrin Gene to Produce Hz Recombinants
    Materials and Methods
        Restriction Mapping
        Southern Blotting
        DNA Sequencing
    Identification and Sequencing of the Polyhedrin Gene of Heliothis zea Virus
    Construction of Transfer Vectors
        Parent Plasmids: pHH5 and pHX12
        Construction of Transfer Vectors.
        Transfer Vectors Expressing Beta-Galactosidase
        Generation of Deletions of Heliothis Polyhedrin Amino-Terminal Sequences
Example: Heliothis Viruses For Use In Generation of Recombinant Occlusion Bodies
    Materials and Methods
        In Vitro Propagation of HzSNPV
        Plaque Purification of HzSNPV Isolates
        Larval Propagation of Virus
        Isolation of Virions From Occlusion Bodies
        Isolation of Viral DNA
        Restriction Endonuclease Digestions
        SDS-Polyacrylamide Gel Electrophoresis
    Characterization of HzSNPV In Vitro Propagation and Plaque Purification
    Larval Infections with Occlusion Bodies
    Restriction Enzyme Digestion Patterns of Viral DNAs
    Comparison of Virion Structural Proteins
Example: Cell Line Hosts For Use In Generation of Recombinant Occlusion Bodies
    Materials and Methods
        Cloning of Cell Strains
        Cell Growth Curves
        Quantitation of Polyhedra and Infectious Extracellular Virus Production
        Isozyme Analysis of Cell Isolates
    Characterization of the Cell Lines
        Cell Morphology
        Cell Growth Curves
        Susceptibility to HzSNPV
        Isozyme Analysis of Cell Strains and Cell Lines
Example: Larval Hosts for Use in Generation of Recombinant Occlusion Bodies
    Insect Diet Preparation
    Colony Maintenance
        Rearing of T. ni or H. zea
        Rearing of G. melonella
        Germ-Free Colonies
Example: Heliothis Polyhedrin Gene and Promoter in Autographa Shuttle Vector
    Autographa Shuttle Vectors Encoding an Epitope of the Influenza Hemagglutinin within the Polyhedrin Gene
Example: Production of Recombinant Occlusion Bodies Exposing An Epitope of Influenza Hemagglutinin
    Construction of Shuttle Vectors
    Preparation of Recombinnt Viruses
    Immunological Analyses of the Recombinant Occlusion Bodies
        ELISA Analysis of Surface Expression of Undenatured Influenza Epitope on Recombinant Occlusion Bodies
        Western Blot Analysis of Denatured Recombinant Occlusion Bodies
        Immunoprecipitation Assays of Recombinant Influenza/Polyhedrin Crystals
        Immunogenicity of Recombinant Occlusion Bodies
Deposit of Microorganisms

INTRODUCTION

The present invention is directed to baculoviruses which encode recombinant polyhedrin proteins capable of forming occlusion bodies containing foreign peptides. The recombinant baculoviruses of the invention are formed by replacing regions of the polyhedrin gene that are not essential for occlusion body formation with foreign DNA fragments by recombinant DNA techniques. The recombinant occlusion bodies produced in accordance with the present invention can be particularly useful as vaccines, biological insecticides, and expression vectors. The invention is demonstrated by way of examples in which recombinant baculoviruses were engineered to express recombinant occlusion bodies that present an influenza hemagglutinin epitope. These recombinant occlusion bodies immunoreact with antibodies that define the authentic influenza hemagglutin epitope.

BACKGROUND OF THE INVENTION

INSECT VIRUSES AND OCCLUSION BODIES

Baculoviruses are a group of viruses which are pathogenic for insects and some crustaceans. The virions of these viruses contain rod-shaped nucleocapsids enclosed by a lipoprotein membrane. Two morphologically distinct forms of baculovirus are produced by infected cells: the nonoccluded virus and occluded virus. The nonoccluded virus is synthesized early after infection; nucleocapsids are assembled in the nucleus and acquire an envelope by budding through the plasma membrane to become extracellular virus. In occluded baculoviruses, the virions are embedded in the nucleus in large protein crystals, termed occlusion bodies.

Baculoviruses are members of the family Baculoviridae and the genus Baculovirus. This genus is composed of three subgroups of viruses: the nuclear polyhedrosis viruses (NPV), the granulosis viruses (GV), and the non-occluded viruses.

NPV have occlusion bodies, termed polyhedra, which are polyhedral to cuboidal in shape, and 1–15 $\mu$m in diameter. The lipoprotein membranes contain either single nucleocapsids (SNPV) or multiple (up to 39) nucleocapsids (MNPV) per envelope. Up to 100 virions can be embedded in a single occlusion body (Vlak, J. M. and Rohrmann, G. F., 1985, The Nature of Polyhedrin. In Viral Insecticides for Biological Control, Academic Press, pp. 489–542). Examples of this group of viruses include *Autographa californica* NPV (AcNPV), *Heliothis zea* NPV (HzNPV), and *Bombyx mori* (BmNPV). Comparison of DNA sequences of total viral genomes reveals a less than 2% homology between HzSNPV and AcMNPV, whereas a comparison among various MNPVs shows a greater degree of homology (Smith, G. E. and Summers, M. D., 1982, Virol. 123:393–406). HzSNPV is currently produced and sold in the United States for use as an insecticide under the trade name Elcar ™.

The granulosis viruses have round to ellipsoidal occlusion bodies, termed granula, which are 0.1–1 $\mu$m in size. Each occlusion body contains one singly-enveloped nucleocapsid (Vlak, J. M. and Rohrmann, G. F., supra). (For review, see Tweeten, K. A., et al., 1981, Microbiol. Rev. 45:379–408).

Baculoviruses contain double-stranded, circular DNA molecules, which range from 60–110×10$^6$ daltons. The prototype of the Baculoviridae family is AcNPV, which has a genome of approximately 82–88×10$^6$ daltons (Miller, L. K., 1981, A Virus Vector for Genetic Engineering in Invertebrates. In Genetic Engineering in the Plant Sciences. Praeger Publishers, New York, pp. 203–224). AcNPV replicates in the nucleus of infected insect cells. Two forms of virus are produced as a result of wild-type AcNPV infection, occluded and non-occluded virions.

The apparent role of the occlusion body in the virus life cycle is to provide stability outside the host insect by protecting the virus from inactivating environmental factors. Ingested occlusion bodies dissolve in the alkaline environment of the midgut, releasing virus, particles for another round of infection, late after viral replication. The occlusion body of NPV consists predominantly of a single, approximately 29,000 dalton molecular weight polypeptide, known as polyhedrin (Vlak, J. M. and Rohrmann, G. F., supra). This protein forms the paracrystalline lattice around the virions, and is present as a multimer. Polyhedrin is produced in enormous amounts during the course of viral infection, late after viral replication. As there is no evidence of gene amplification (Tjia, S. T., et al., 1979, Virology 99: 399–409), it is probable that the polyhedrin promoter is an extremely efficient one.

POLYHEDRIN

The occlusion body (OB) exists as a multimer of the approximately 30 kilodalton polyhedrin polypeptide which forms a paracrystalline lattice around the viral particle (Tinsley, T. W. and Harrap, K. A., 1978, Comprehensive Virology, Vol. 12, Fraenkel-Conrat, H. and R. Wagner (eds.), Plenum Press, New York, pp. 1–101). After alkali dissolution of OBs, a polyhedrin particle with a sedimentation coefficient of 11S13S (200–374 kilodaltons) can be isolated (Bergold, G. H. and Schramm, G., 1942, Biol. Zentralblatt. 62:105; Bergold, G. H., 1947, Zeitschr. Naturforsch. 2b:122; Bergold, G. H., 1948, Zeitschr. Naturforsch. 3b:338; Harrap, K. A., 1972, Virology 50:124; Eppstein, D. A. and Thoma, J. A., 1977, Biochem. J. 167:321; Rohrmann, G. F., 1977, Biochem. 16:1631). X-ray diffraction studies determined that polyhedrin is crystallized in a body-centered cubic lattice (Engstrom, A., 1974, Biochem. Exp. Biol. 11:7). Electron microscopic analysis of polyhedrin crystals suggests the arrangement of subunits is consistent with six armed nodal units (Harrap, K. A., 1972, Virology 50:124). Crosslinking analysis of polyhedrin utilizing dimethyl suberimidate indicates a dodecameric structure. Therefore, each arm of the nodal unit is composed of two subunits (Scharnhorst, D. W. and Weaver, R. F., 1980, Virology 102:468). Alkali solubility of the crystal suggests that salt bridges are formed between the amino acid side chains. This indicates that the paracrystalline lattice is maintained by noncovalent, ionic intermolecular associations of the individual monomers. Disulfide bond formation may also influence the quaternary structure of the multimeric form.

Baculovirus occlusion body protein has been termed polyhedrin for NPVs and granulin for GVs. However, recent studies have shown that polyhedrins and granulins all belong to one group of related proteins (Rohrmann, G. F., et al., 1981, J. Mol. Evol. 17:329; Smith, G. E. and Summers, M. D., 1981, J. Virol. 39:125). Tryptic peptide analyses have shown that polyhedrins from MNPVs, SNPVs, and GVs have many common fragments (Summers, M. D. and Smith, G. E., 1975, Intervirology 6:168–180; Maruniak, J. E. and Summers, M. D.,1978, J. Invertebr. Pathol. 32:196). Such similarities in sequence hav been reported (Vlak, J. M. and Rohrmann, G. F., 1985, The Nature of Polyhedrin. In Viral Insecticides for Biological Control. Academic Press, pp. 489–542.). Some polyhedrins have been found to be more closely related to granulins than to other polyhedrins (Rohrmann, G. F., et al., supra). Thus, hereinafter, the term polyhedrin will be used to refer to the entire group of related proteins.

Comparison of the amino acid sequences of six lepidopteran NPV polyhedrins (Vlak, J. M. and Rohrmann, G. F., supra, pp. 506–508) reveals that 80–90% of amino acids are conserved within these proteins. There are several regions which can be distinguished on the basis of sequence conservation. For example, amino acids 15–26 and 58–86 are highly conserved. The region between amino acids 38–55 is hydrophilic and highly variable. Other variable sites include the N-terminal region, amino acids 120–127, 145–148, 165, 195, and 216 (Vlak, J. M. and Rohrmann, G. F., supra).

RECOMBINANT DNA TECHNIQUES AND BACULOVIRUS

The use of recombinant DNA technology for the production of proteins involves the molecular cloning and expression in an appropriate vector of the genetic information encoding the desired proteins. Baculoviruses are useful as recombinant DNA vector systems since they are double-stranded DNA replicating units, into which can be inserted a large amount of foreign DNA (20 megadaltons or more), and which provide at least one strong promoter (polyhedrin) which controls a gene with nonessential function for propagation in cell culture, which is available for replacement or insertion into by foreign DNA (Miller, L. K., 1981, A Virus Vector for Genetic Engineering in Invertebrates, In Genetic Engineering in the Plant Sciences. Praeger Publishers, New York, pp. 203–224; Vlak, J. M. and Rohrmann, G. F., 1985, The Nature of Polyhedrin, In Viral Insecticides for Biological Control. Academic Press, pp. 489–542). A method for the production of recombinant proteins using a baculovirus system has been described (Pennock et al., 1984, Mol. Cell. Biol. 4:399; Smith et al., 1983, J. Virol. 46:584). Baculovirus vectors are constructed, which express foreign DNA which has been inserted into the viral genome. Upon introduction into an appropriate host, the foreign protein is produced.

The expression of foreign DNA in recombinant baculoviruses requires the ligation of baculovirus sequences to a DNA sequence encoding a foreign protein so that the protein-coding sequences are under the control of a promoter. Plasmid vectors, also called insertion vectors, have been constructed to insert chimeric genes into AcNPV. One example of such an insertion vector is composed of: (a) an AcNPV promoter with the transcriptional initiation site; (b) several unique restriction endonuclease recognition sites located downstream from the transcriptional start site, which can be used for the insertion of foreign DNA fragments; (c) AcNPV DNA sequences (such as the polyhedrin gene), which flank the promoter and cloning sites, and which direct insertion of the chimeric gene into the homologous nonessential region of the virus genome; and (d) a bacterial origin of replication and antibiotic resistance marker for replication and selection in E. coli. Examples of such vectors are described by Miyamota et al. (1985, Mol. Cell. Biol. 5:2860).

Recombinant baculoviruses have been produced by cotransfection of cells with recombinant bacterial plasmids containing the foreign gene, together with baculovirus DNA. The foreign gene is inserted into or replaces the nonessential polyhedrin gene of the viral genome through homologous recombination within the infected cell. The resulting recombinant plaques can be screened visually for lack of occlusion bodies resulting from the loss of the functional polyhedrin gene. The infected cells can also be screened using immunological techniques, DNA plaque hybridization, or genetic selection for recombinant viruses which subsequently can be isolated. These baculovirus recombinants retain their essential functions and infectivity.

Foreign gene expression can be detected by enzymatic or immunological assays (for example, immunoprecipitation, radioimmunoassay, or immunoblotting). High expression levels can be obtained by using strong promoters or by cloning multiple copies of a single gene.

Several foreign proteins have been successfully expressed under control of the polyhedrin promoter in occlusion body-negative baculovirus systems. Human interleukin 2 (Smith et al., 1985, Proc. Natl. Acad. Sci. U.S.A. 82: 8404–8408), human c-myc (Miyamoto et al., 1985, Mol. Cell. Biol. 5:2860–2865), bacterial beta-galactosidase (Pennock et al., 1984, Mol. Cell. Biol. 4:399–406), influenza virus haemagglutinin (Kuroda et al., 1986, EMBO 5: 1359–1365), and human beta-interferon (Smith et al., 1983, Mol. Cell. Biol. 3:2156–2165) have all been expressed in insect cells under the control of the polyhedrin promoter in recombinant AcNPV expression vectors. Human alpha-interferon has been expressed in silkworms by ligation to the polyhedrin promoter of BmNPV (Maeda et al., 1985, Nature (London) 315: 592–594). Smith and Summers (European Patent Application Publication No. 0 127 839, 12-1-2-84) propose a method for producing recombinant baculovirus expression vectors, and report the use of recombinant AcNPV vectors to express human beta-interferon and human interleukin 2, under the control of the polyhedrin promoter.

VACCINES FOR VIRAL INFECTIONS

A number of methods are currently in use for the prevention and treatment of viral infections. These include vaccines which elicit an active immune response, treatment with chemotherapeutic agents and interferon treatment.

Traditional ways of preparing vaccines include the use of inactivated or attenuated viruses. Inactivation of the virus renders it harmless as a biological agent but does not destroy its immunogenicity. Injection of these "killed" virus particles into a host will then elicit an immune response capable of neutralizing a future infection with a live virus. However, a major concern in the use of killed vaccines (using inactivated virus) is failure to inactivate all the virus particles. Even when this is accomplished, since killed viruses do not multiply in their host, the immunity achieved is often short lived and additional immunizations are usually required. Finally, the inactivation process may alter the viral proteins rendering them less effective as immunogens.

Attenuation refers to the production of virus strains which have essentially lost their disease producing ability. One way to accomplish this is to subject the virus to unusual growth conditions and/or frequent passage in cell culture. Viral mutants are then selected which have lost virulence but yet are capable of eliciting an immune response. The attenuated viruses generally make good immunogens as they actually replicate in the host cell and elicit long lasting immunity. However, several problems are encountered with the use of live vaccines, the most worrisome being insufficient attenuation.

An alternative to the above methods is the use of subunit vaccines. This involves immunization only with those proteins which contain the relevant immunological material. For many enveloped viruses, the virally encoded glycoprotein contains those epitopes which are capable of eliciting neutralizing antibodies; these include the glycoproteins of La Crosse Virus (Gonzalez-Scarano, F., Shope, R. E., Calisher, C. E., and Nathanson, N., 1982, Virology 120:42), Neonatal Calf Diarrhea Virus (Matsuno, S. and Inouye, S., 1983, Infection and Immunity 39:155), Venezuelan Equine Encephalomyelitis Virus (Mathews, J. H. and Roehrig, J. T., 1982, J. Imm. 129:2763), Punta Toro Virus (Dalrymple, J. M., Peters, C. J., Smith, J. F., and Gentry, M. K., 1981, In Replication of Negative Strand Viruses, D. H. L. Bishop and R. W. Compans, eds., p. 167. Elsevier, New York), Murine Leukemia Virus (Steeves, R. A., Strand, M., and August, J. T., 1974, J. Virol. 14:187), and Mouse Mammary Tumor Virus (Massey, R. J. and Schochetman, G., 1981, Virology 115:20). One advantage of subunit vaccines is that the irrelevant viral material is excluded.

Vaccines are often administered in conjunction with various adjuvants. The adjuvants aid in attaining a more durable and higher level of immunity using smaller amounts of antigen in fewer doses than if the immunogen were administered alone. The mechanism of adjuvant action is complex and not completely understood. However, it may involve the stimulation of phagocytosis and other activities of the reticuloendothelial system as well as a delayed release and degradation of the antigen. Examples of adjuvants include Freund's adjuvant (complete or incomplete), Adjuvant 65 (containing peanut oil, mannide monooleate and aluminum monostearate), the pluronic polyol L-121, Avridine, and mineral gels such as aluminum hydroxide, aluminum phosphate, or alum. Freund's adjuvant is no longer used in vaccine formulations for humans because it contains nonmetabolizable mineral oil and is a potential carcinogen.

VACCINES FOR PARASITIC AND BACTERIAL INFECTIONS

The development of vaccines for the prevention of parasitic or bacterial diseases is the focus of much research effort. Vaccines are presently available for diphtheria, pertussis, and tetanus (Warren, K. S., 1985, In Vaccines85, Lerner, R. A., R. M. Chanock, and F. Brown (eds.), Cold Spring Harbor Laboratory, New York, pp. 373-376). In addition, a vaccine consisting of the polysaccharide capsule of Hemophilus influenzae was recently licensed, although it is ineffective in preventing disease in certain subgroups of the population (Granoff, D. M. and Munson, R. S., Jr., 1986, J. Infect. Dis. 153:448-461). No vaccines currently exist for any of the many protozoan infections such as malaria or helminth infections such as schistosomiasis and ascariasis. The protective effects of antisera directed against epitopes of Escherichia coli toxins, cholera toxins, gonococcal pili, and malaria surface antigens (Vaccines85, 1985, Lerner, R. A., R. M. Chanock, and F. Brown (eds.), Cold Spring Harbor Laboratory, New York; Modern Approaches to Vaccines, 1984, Chanock, R. M., and R. A. Lerner (eds.), Cold Spring Harbor Laboratory, New York) are among the many systems presently under investigation.

SUMMARY OF THE INVENTION

The present invention is directed to recombinant baculoviruses which encode fusion polyhedrin proteins capable of forming occlusion bodies containing foreign peptides. The recombinant baculoviruses of the invention are formed by insertion into or replacement of regions of the polyhedrin gene that are not essential for occlusion body formation with foreign DNA fragments by recombinant DNA techniques. The present invention also relates to vector/host systems which can direct the expression of the recombinant polyhedrin genes in different hosts, including but not limited to, cultured cells, larvae, or microorganisms.

The recombinant occlusion bodies (OBs) of the present invention comprise crystallized polyhedrin fusion proteins which bear the heterologous gene product on the surface of or within the occlusion body. Where the heterologous gene product comprises an epitope of a pathogenic microorganism, the recombinant OBs of the present invention can be particularly useful in vaccine formulations. In another embodiment, the foreign sequence can encode a molecule with insecticidal activity, thus increasing the lethality of the baculovirus to the host agricultural pest. Recombinant OBs expressing foreign peptides comprising antigenic determinants have uses in immunoassays. In yet another embodiment of the invention, the foreign sequence can encode a molecule with enzymatic activity so that the recombinant OBs can be used as a reaction surface. The recombinant viruses of the present invention can also be used as expression vectors for the production of the foreign peptide(s) contained on the recombinant OB. The production of recombinant OBs can also facilitate the isolation of the component heterologous gene product in substantially pure form.

The invention is demonstrated by way of examples in which recombinant baculoviruses were engineered to express recombinant occlusion bodies that present an influenza hemagglutinin epitope. These recombinant occlusion bodies immunoreact with antibodies that define the authentic epitope.

DEFINITIONS

The following terms and abbreviations have the meanings indicated:
Ac=*Autographa californica*
Hz=*Heliothis zea*
ECV=extracellular virus
poly H=polyhedrin
Isozymes:
EST=esterase
FUM=fumarate hydratase
LDH=lactate dehydrogenase
MDH=malate dehydrogenase
Buffers:
TE=10 mM Tris-HCl, 1 mM EDTA, pH 7.6
TBE=81.2 mM Tris, 20 mM boric acid, 1.5 mM EDTA, pH 8.9
TC=9.7 mM Tris, 2.13 mM citric acid, pH 7.1
OB=Occlusion body, a paracrystalline protein matrix which occludes baculovirus virions. The paracrystalline protein matrix forms a refractile body which is polyhedral, cuboidal or spherical in shape. The term OB will also be used hereinafter to refer to lattices formed in vitro by the recrystallization of soluble polyhedrin.

NPV=Nuclear Polyhedrosis Viruses, a subgroup of the baculovirus genus in which the nucleocapsids are enveloped by a lipoprotein membrane singly (SNPV) or in multiples (MNPV) per common envelope. Up to 100 of these virion packages are embedded in an occlusion body, polyhedral to cuboidal in shape and 1–15 μm in diameter.

GV=Granulosis Virus, a subgroup of the baculovirus genus in which one singly-enveloped nucleocapsid is embedded per occlusion body, round to ellipsoidal in shape, and 0.1–1 μm in size.

NOBV=Non-occluded baculoviruses.

MCS=Multiple cloning site. A region of DNA containing a series of unique restriction endonuclease cleavage sites.

SDS-PAGE=Sodium dodecylsulfate polyacrylamide gel electrophoresis

Cassette Transfer Vector=A transfer vector comprising a polyhedrin promoter and a restriction enzyme recognition site into which a heterologous gene sequence can be inserted under the control of the polyhedrin promoter, in which a polyhedrin promoter and the restriction site are flanked by sequences that are homologous to parent vector sequences. Heterologous gene sequences can be inserted into the cassette transfer vectors which can then be used to construct recombinant expression vectors via homologous recombination in vivo with a parent vector.

Transfer Vector=A transfer vector comprising a polyhedrin promoter and a heterologous gene sequence positioned under the control of the polyhedrin promoter, in which the polyhedrin promoter and the heterologous gene sequences are flanked by sequences that are homologous to parent vector sequences. The transfer vector containing the heterologous gene sequence can be used to construct recombinant expression vectors via homologous recombination in vivo with a parent vector.

Cassette Expression Vector=An expression vector comprising a polyhedrin promoter and a restriction enzyme recognition site into which a heterologous gene sequence can be inserted under the control of the polyhedrin promoter so that the gene is expressed in a suitable host.

Expression Vector=An expression vector comprising a polyhedrin promoter and a heterologous gene sequenoe positioned under the control of the polyhedrin promoter so that the heterologous gene is expressed in a suitable host.

DESCRIPTION OF THE FIGURES

FIG. 1. Nucleotide sequence of the polyhedrin gene of *Heliothis zea.* The nucleotide sequence was determined using the dideoxy chain termination method of Sanger et al. (1977, Proc. Natl. Acad. Sci. U.S.A. 74:5463). The deduced amino acid sequence is presented below the nucleotide sequence. Restriction sites which were used in the cloning protocols are indicated. Solid bars indicate regions of the amino acid sequence which have been identified as hydrophilic portions of polyhedrin.

FIG. 1A. Restriction map of the Heliothis polyhedrin gene. A restriction endonuclease digestion map of the Heliothis polyhedrin gene for the restriction endonucleases HindIII, NruI, HincII, and AccI is presented. The map was derived from the nucleotide sequence shown in FIG. 1. Numbers in parentheses represent the number of the nucleotide in FIG. 1.

FIG 1B. Nucleotide sequencing strategy of the Heliothis polyhedrin gene. The sequencing strategy used in the dideoxy chain termination method (Sanger, F., et al., 1977, Proc. Natl. Acad. Sci. U.S.A. 74:5463–5467) of sequencing of the Heliothis polyhedrin gene is depicted. The arrows indicate the direction of sequencing on each fragment. The following abbreviations are used in the figure: Xho (XhoI), Sal (SalI), RI (EcoRI), H3 (Hind III), HII (HindII), and Nr (NruI).

FIG. 2. Homology of amino acid sequences of polyhedrin genes of *Autographa californica* MNPV (Ac), Heliothis zea SNPV (Hz) and *Bombyx mori* NPV (Bm). The DNA and deduced amino acid sequence of the polyhedrin gene of Ac is presented (Hooft van Iddekinge, B. J. L., et al., 1983, Virology 131:561). The differences between the deduced amino acid sequence of the Ac polyhedrin and that of Bm (Kozlov, E. A., et al., 1981, Khim 7:1008) and Hz (see FIG. 1, supra), are indicated. Where an amino acid is present in one sequence and absent from another, the missing amino acid is indicated by the following symbol: ———.

FIG. 4. Polyhedrin polylinker sequence. A synthetic polylinker gene sequence and its encoded amino acids are depicted. This gene segment encodes the *Autographa californica* polyhedrin gene extending from the amino terminus to the BamHI site corresponding to amino acid 58. Restriction endonuclease digestion sites are indicated below the DNA sequence. The PvuI, ScaI, BclI, and XbaI sites correspond to amino acids 9, 19, 27, and 46, respectively.

FIG. 5B. The construction of transfer vector Phe2.-61ac, which contains a functional *E. coli* betagalactosidase gene. Phe2.61ac can be used to insert other foreign genes or fragments thereof within the Heliothis polyhedrin gene, which can then be transferred to the Heliothis virus genome by in vivo recombination. The following abbreviations are used in the figure: Xba (XbaI), Bam (BamHI), Kpn (KpnI), Sma (SmaI), Oligo (Oligonucleotide), and MCS (Multiple Cloning Site).

FIG. 5C. The construction of transfer vectors which contain deletions in the amino terminal-coding region of the Heliothis polyhedrin gene. These transfer vectors can be used to insert foreign genes within the polyhedrin gene and to produce $H_z$ viruses via in vivo recombination. The following abbreviations are used in the figure: Xba (XbaI), bam (BamHI), kpn (KpnI), sma (SmaI), sph (SphI), bgl (BglI), and pst (PstI).

FIG. 11. Comparison of isozyme banding patterns between all IPLB-HZ1075 derived cell strains and Heliothis zea larvae with isozymes FUM, LDH, and EST. Cell and larval extracts were electrophoresed in a 5% polyacrylamide gel (95% acrylamide, 5% bis-acrylamide) in either TBE or TC buffer and stained for the appropriate enzyme. Staining for FUM and for LDH confirm that the cell strains were derived from the parental IPLB-HZ1075 (W+) cell line and that they are ultimately derived from Heliothis zea larvae. The differences in the EST gels suggest that all of the strains are not identical. Staining procedures for the isozymes are described infra. A) FUM=Fumarate Hydratase B) LDH=Lactate Dehydrogenase C) EST=Esterase.

FIG. 15. The construction of a transfer vector containing a foreign DNA sequence encoding amino acids 98-106 of the influenza hemagglutinin inserted at a specific HpaII site within the Autographa polyhedrin gene. This transfer vector can be used to produce recombinant Autographa viruses containing the influenza sequence via in vivo recombination, which express the foreign sequence under the control of the Autographa polyhedrin promoter.

FIG. 16A. The construction of vector pAV15InHem. This vector contains an altered polyhedrin gene in which the polyhedrin sequence between amino acid residue numbers 43 through 50 were replaced with an epitope of influenza hemagglutinin.

FIG. 17A and 17B. The construction of vector pAV17b InHem-1 in which the epitope of influenza hemagglutinin is located after amino acid residue number 1 of polyhedrin. This plasmid encodes a unique SphI restriction site at the initiation codon of polyhedrin.

DETAILED DESCRIPTION OF THE INVENTION

Figure 3:
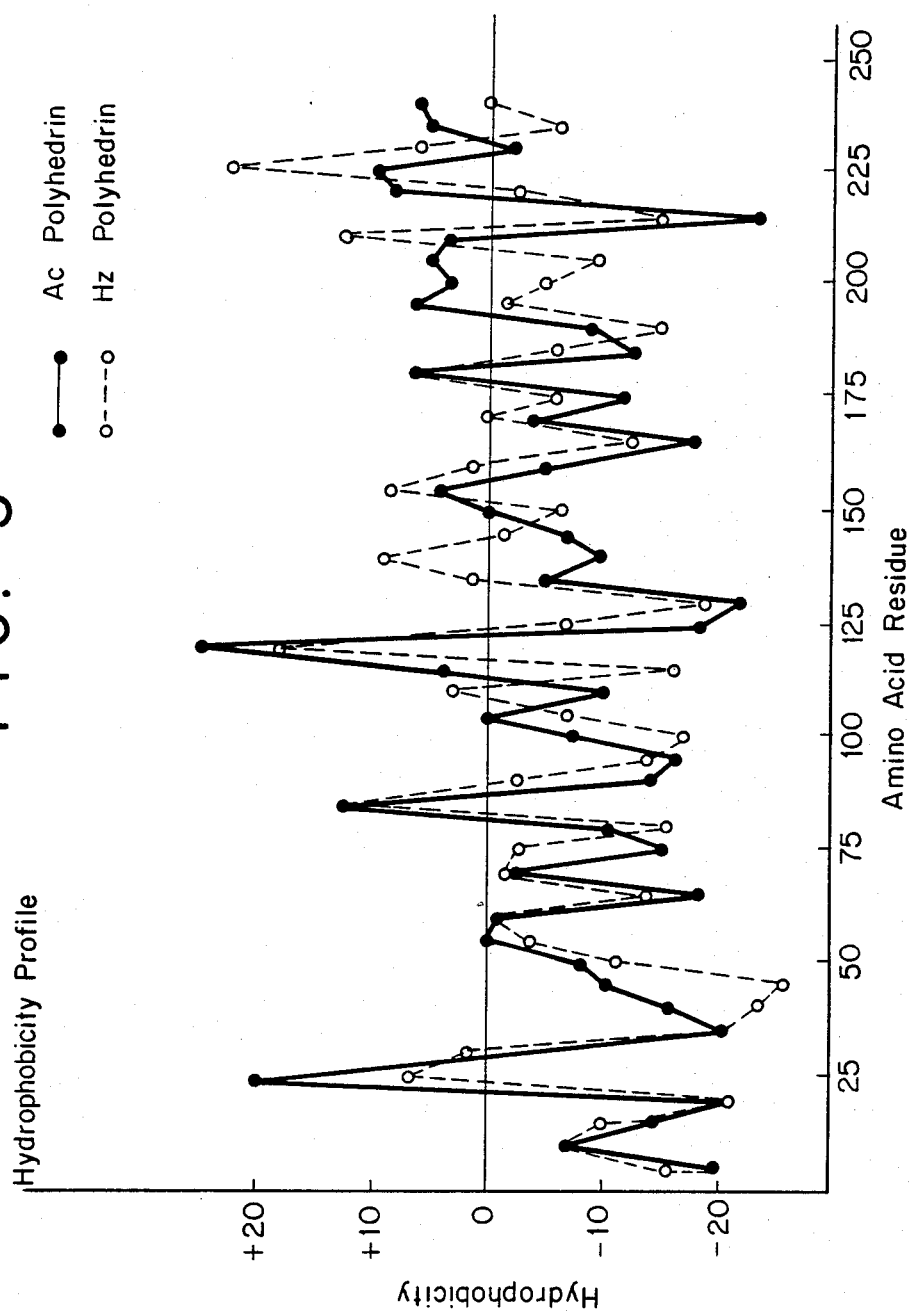
FIG. 3. Hydrophobicity profile of Hz and Ac polyhedrin. The hydrophobicity of each amino acid residue as measured by Hopp and Woods (1981, Proc. Natl. Acad. Sci. U.S.A. 78: 3824) was plotted against the amino acid residue number of the polyhedrin gene. The amino terminus and amino acid residues 35–50 were identified as hydrophilic regions of the Heliothis polyhedrin molecule.

The present invention relates to recombinant baculoviruses which encode fusion polyhedrin proteins capable of forming occlusion bodies containing foreign peptides. The recombinant OBs of the present invention comprise crystallized polyhedrin fusion proteins which bear the heterologous gene product on the surface of or within the occlusion body. The recombinant OBs are formed by replacing regions of the baculovirus polyhedrin gene that are nonessential for occlusion body formation with sequences encoding foreign peptides. The present invention is also directed to vector/host systems which can express the recombinant polyhedrin gene in different hosts, including but not limited to, cultured cells, larvae, or microorganisms.

According to one embodiment of the invention, the recombinant OB which contains an immunogenic determinant of a pathogenic microorganism can be used in vaccine formulations.

In another embodiment of the invention, recombinant OBs comprising sequences with insecticidal activity can be used to increase lethality of the baculovirus to host agricultural pests.

According to another embodiment of the invention, the recombinant OBs which expose an active site of an enzyme can be used as immobilized enzyme in appropriate procedures.

In other embodiments, the recombinant OBs of the present invention have uses in immunoassays and as expression vectors. The production of recombinant polyhedrin crystals can also facilitate the isolation of the component heterologous gene product in substantially pure form.

The method of the invention may be divided into the following general stages solely for the purpose of description: (a) identification of modifiable domains encoded by the polyhedrin gene, (b) identification and characterization of immunodominant peptides for expression on or within recombinant occlusion bodies, (c) construction of recombinant polyhedrin genes, (d) selection of recombinant occlusion bodies, (e) verification of expression of foreign epitopes on or within the recombinant occlusion body, and (f) determination of immunopotency of foreign epitopes expressed on or within recombinant occlusion bodies.

THE GENERATION OF RECOMBINANT OBs CONTAINING ANTIGENIC DETERMINANTS OF HETEROLOGOUS PROTEINS

IDENTIFICATION OF MODIFIABLE DOMAINS ENCODED BY THE POLYHEDRIN GENE

Exposing new antigenic determinants on the surface of or within the OB requires identifying regions of the polyhedrin protein that can be modified without affecting the formation or stability of the lattice. Such segments can be altered by the insertion of ne epitopes without interfering with the integrity of the crystalline lattice. The identification of modifiable domains can be accomplished by comparing sequences of cloned polyhedrin genes, analyzing polyhedrin genes encoding truncated polyhedrin proteins, and by structural analysis of polyhedrin amino acid sequences. Exposing the heterologous gene product on the surface of the OB may be preferable (but not required) for formulation in vaccines. Surface domains of the OB may be more amenable to alteration without concomitant destruction of crystal integrity than internal domains. The identification of polyhedrin surface domains can be accomplished by hydrophilicity analysis of polyhedrin, and by generating and characterizing monoclonal antibodies to OBs. Segments of the sequence which are hydrophilic and hypervariable regions are prime candidates for insertion into or replacement with the foreign sequence of interest. However, sequences of the polyhedrin gene which encode hydrophobic regions of the polyhedrin protein may also be inserted into or replaced by heterologous sequences.

In the specific embodiments which exemplify the invention described herein we have used the analyses described infra to identify the amino terminus and amino acid residue numbers 38-50 of the Autographa polyhedrin as modifiable domains. In particular, the data presented in the Examples, infra, demonstrate that foreign epitopes may be inserted in the polyhedrin sequence at amino acid residue number 1, 43 or 50 in order to produce recombinant OBs that expose the foreign epitope.

HYDROPHILICITY ANALYSIS OF POLYHEDRIN

In order to determine which portions of the polyhedrin gene sequence are more likely to be surface domains, hydrophobic and hydrophilic regions of the polyhedrin amino acid sequence and the corresponding regions of the gene sequence which encode the hydrophilic and hydrophobic regions should be identified. Since the hydrophilic regions of the amino acid sequence are likely to be external domains of the crystal, and, furthermore, are likely to be external domains of the polyhedrin monomer upon crystal dissolution, such regions may be especially useful in an embodiment of the invention employing recombinant OBs in a vaccine formulation, since they would readily provide for presentation of the foreign epitope to the host immune system. Portions of the polyhedrin gene which encode hydrophilic regions are prime candidates for insertion into or replacement by a heterologous gene sequence, since the foreign epitope inserted therein is thus likely to be immunogenic in a vaccine formulation. Thus, the portions of the polyhedrin gene sequence which encode regions of the polyhedrin protein which are both hydrophilic and which are also determined to be highly variable (see Section 5.1.1.2, infra), are good candidates for replacement by heterologous gene sequences, so that the resulting fusion polyhedrin proteins will crystallize and form recombinant OBs containing immunogenic foreign epitopes.

Sequences of the polyhedrin gene which encode hydrophobic regions of the polyhedrin protein may also be inserted into or replaced by heterologous gene sequences, and provide for a recombinant OB that is useful in a vaccine formulation. In a particular embodiment, gene sequences which encode an amphipathic peptide (i.e. a peptide having one face which is hydrophobic, one face which is hydrophilic) (see Section 5.4.1., infra) may be inserted into a region of the polyhedrin gene that is nonessential for crystallization and which encodes a hydrophobic portion of the polyhedrin protein.

In a particular embodiment of the invention, we have identified the hydrophobic and hydrophilic regions of the Autographa, Heliothis and Bombyx morii polyhedrin amino acid sequence and the corresponding DNA fragments which encode them (See FIG. 3 and FIG. 1). We have identified the amino terminus and amino acid residue numbers 38-50 of Autographa polyhedrin (see FIG. 3) as hydrophilic regions of the polyhedrin protein which are probably on the surface of the protein and are thus also likely to be on the surface of the OB. The heterologous gene sequence can be inserted into the polyhedrin gene sequence so that the heterologous gene either interrupts or replaces all or a portion of nucleotide residue numbers 1 to 12, or 142 to 180, which encode these regions of the amino acid sequence (see FIG. 1). It should be noted that these residue numbers are approximate and that any restriction site or sites which occur, or are genetically engineered to occur, within or in proximity to these regions may be used to specifically cleave the polyhedrin gene sequence in order to insert the heterologous gene sequence. Some restriction sites which may be useful include, but are not limited to, the restriction sites indicated in FIG. 1. It is preferred to use restriction sites that are unique, so that where no suitable sites exist, new sites may be obtained, for example, by in vitro mutagenesis (see Section 5.1.3, infra).

SEQUENCE COMPARISONS OF DIFFERENT POLYHEDRIN GENES

Comparison of the sequences of different polyhedrin genes is with the aim of identifying regions of the gene that are hypervariable. The most hypervariable regions probably constitute regions nonessential for lattice formation which may be genetically manipulated for use in exposing a new antigenic determinant on the surface of or within the OB.

In a specific embodiment, regions of the polyhedrin gene which are variable and which encode alpha-helical domains may be inserted into or replaced by a sequence encoding a foreign epitope that is also alpha-helical and which may be amphipathic, so that a recombinant protein is produced which allows both the OB and the epitope within it to retain their structural integrity. (An example of such a polyhedrin gene sequence, which is both variable and encodes an alpha-helical region, is that encoding amino acids 37–49; see the discussion infra and section 5.1.1.4.).

In a specific embodiment, amino acid sequence comparisons of a number of baculovirus polyhedrin proteins reveal a high degree of sequence homology among these different proteins (FIG. 2). Overall, the Heliothis zea (HzSNPV), Bombyx mori (BmMNPV) and *Autographa californica* (AcMNPV) polyhedrin proteins are 80–85% homologous. The sequence homology is expected given the similar functional and structural roles of these proteins in the different viruses. One might expect that the conservation of certain regions is essential for crystal formation. However, there are small regions where the amino acid sequence is highly variable among the different polyhedrin proteins. In particular, the region between amino acids 37–49 of the polyhedrin protein shows significant variability. Interestingly, the procedures of Hopp and Woods (Hopp, T. and Woods, K., 1981, Proc. Natl. Acad. Sci. U.S.A. 78:3824) indicate that this segment coincides with the most hydrophilic region of the *Heliothis zea* polyhedrin protein. These results indicate that this variable hydrophilic region may define a section of the protein that is not essential for crystallization and is probably on the surface of the protein. From this analysis the segment encoding amino acids 37–49 is a putative modifiable surfacedomain. Through a similar analysis, the amino terminus (roughly amino acids 1 through 4) is also identified as a hydrophilic, potentially variable region of the polyhedrin protein.

A comparison of the sequences from six lepidopteran NPV polyhedrins (Vlak, J. M. and Rohrmann, G. F., 1985, The Nature of Polyhedrin, In Viral Insecticides for Biological Control, Academic Press, pp. 489–452) reveals regions of homology which can be identified for modification; these include but are not limited to the amino terminus (e.g., amino acid 1); amino acids 37–49, 86–96, 120–127, 141–150, 193–198, and 208–216 (id.); as well as the carboxy terminus (e.g., the amino acid residues after amino acid number 245). In particular, amino acid residue numbers 58 and 211 are attractive candidates for modification due to the location of unique BamHI and KpnI sites, respectively, in the coding sequences for these regions.

As discussed previously, polyhedrins of NPVs and polyhedrins of GVs form a group of related molecules (Vlak, J. M. and Rohrmann, G. F., *supra*; Tweeten, K. A., et al., 1981, Microbiol. Rev. 45:379–408). Thus, polyhedrins of 9granulosis viruses (qranulins) can also be altered in accordance with the present invention to express a foreign peptide on or within the occlusion body. A comparison of some NPV and GV polyhedrin (Vlak, J. M. and Rohrmann; G. F, supra of pp. 489–542) reveals that the variable N-terminal amino acid sequences of some NPV polyhedrins and a GV polyhedrin, may be manipulated to form recombinant OBs in particular embodiments of the present invention.

SEQUENCE ANALYSIS OF POLYHEDRIN GENES ENCODING MUTANT OR TRUNCATED POLYHEDRIN PROTEINS

A second approach for identifying modifiable regions of polyhedrin is to analyze sequences of mutant or truncated polyhedrin proteins. Any mutant polyhedrin gene which is contained within the genome of a virus that still produces OBs, can be analyzed to determine its mutation. The mutation contained in such a gene represents a point or region of the wild-type polyhedrin gene which can be altered without losing the ability to form OBs.

For example, a baculovirus that produces a truncated polyhedrin protein, which still forms occlusion bodies, can be analyzed by cloning and sequencing its polyhedrin gene. Regions that are non essential for crystallization may be identified by comparison of the truncated sequence to that of other known polyhedrins. The corresponding region of the full length polyhedrin gene could be replaced, or heterologous sequences could be inserted into the appropriate region of the truncated gene, in order to express a new antigenic determinant. One example of a mutant which has been isolated and may be analyzed in such a fashion, is a mutant AcMNPV which may differ from other polyhedrins by a small deletion of 20–30 amino acids. This AcMNPV produces tetrahedral rather than polygonal occlusion bodies, which contain a 31 kD polyhedrin protein rather than the 33 kD wild-type polyhedrin.

Another AcMNPV mutant, termed M5, has been described (Carstens, E. B., 1982, J. Virol. 43:809–818; Carstens, E. B., et al., 1986, J. Virol. 58:684–688). M5 has a single point mutation within the polyhedrin gene which results in a substitution of leucine for proline at amino acid 58 of the polyhedrin protein. However, this single alteration results in a drastic morphological change in the polyhedra, producing cubic occlusion bodies. Thus amino acid 58 is possibly critical to the proper folding of the polyhedrin molecule (Carstens, E. B., et al., supra).

Cloning and sequencing the mutant polyhedrin gene can be accomplished by any technique known in the art (Maniatis, T., et al., 1982, Molecular Cloning, A Laboratory Manual, Cold Spring Harbor Laboratory, New York). For example, in order to generate DNA fragments encoding polyhedrin sequences (hereinafter referred to as polyhedrin DNA), the polyhedrin DNA may be cleaved by restriction enzyme digestion, DNase digestion, physical shearing, etc. Identification of the polyhedrin DNA can be accomplished in a number of ways, including, but not limited to, nucleic acid hybridization, comparison of restriction digestion patterns with known restriction maps, and mRNA selection through nucleic acid hybridization followed by in vitro translation. The polyhedrin DNA, or total baculovirus DNA, is inserted into the cloning vector which is used to transform appropriate host cells so that many copies of the polyhedrin sequences are generated. This can be accomplished by ligating the polyhedrin DNA into a cloning vector with complementary cohesive termini, with or without first ligating linkers onto DNA termini in order to generate desired restriction sites, or blunt-end ligation, homopolymeric tailing, etc. Any of a large number of vectorhost systems may be used. Vector systems may be either plasmids or modified viruses, but the vector system must be compatible with the host cell used. Recombinant molecules can be introduced into cells via transformation, transfection, or infection. Identification of a cloned polyhedrin gene can be achieved by any technique known in the art. Such techniques include, but are not limited to, screening for expression of the gene by colony blot analysis (Huynh, T. V., et al., 1985, In DNA Cloning: A Practical Approach, Vol. 2, Glover, D. M. (ed.), IRL Press, Oxford, pp. 49–78) using anti-polyhedrin antibody as a probe, or using a labelled polyhedrin gene fragment to screen colonies or plaques. DNA sequence analysis can be used to verify the identity of the polyhedrin gene.

In a specific embodiment of the present invention, plasmid or bacteriophage lambda libraries containing DNA inserts derived from the mutant AcMNPV strain can be constructed. Clones containing the mutant polyhedrin gene can be identified by colony or plaque hydridization to labelled polyhedrin gene probes (Grunstein, M. and Hogness, D., 1975, Proc. Natl. Acad. Sci. U.S.A. 72:3961; Benton, W., and Davis, R., 1977, Science 196:180).

Once the polyhedrin DNA-containing clone has been identified, it may be grown, harvested and its DNA insert may be characterized as to its restriction sites by various techniques known in the art (Maniatis, T., et al., Molecular Cloning, A Laboratory Manual, Cold Spring Harbor Laboratory, New York).

The sequence of the polyhedrin DNA insert can then be determined. Methods by which this may be accomplished include the Maxam-Gilbert procedure (Maxam, A. M., and Gilbert, W., 1980, Meth. Enzymol. 65:499) or the Sanger dideoxy chain termination procedure (Sanger, F., et al., 1977, Proc. Natl. Acad. Sci. U.S.A. 74:5463). In a specific embodiment employing the Sanger technique, appropriate segments of the polyhedrin DNA can be preferably subcloned into M13 vectors (Messing, J., 1983, Meth. Enzymol. 101:20) for optimal sequencing efficiency.

STRUCTURAL ANALYSIS OF POLYHEDRIN AMINO ACID SEQUENCES

While the hydrophilicity profile and sequence comparisons of the polyhedrin protein help identify modifiable domains, these analyses rely on the primary structure of the protein. There may be conformational restrictions that severely limit the ability to modify such domains. The region may be either directly or indirectly involved in lattice formation such that modification of the region would destabilize the crystal. Secondary structural analysis (Chou, P. and Fasman, G., 1974, Biochemistry 13:222) can therefore be done in order to identify regions that assume secondary structures which may be more conducive to modification without concomitant lattice disruption. Similar analysis of the amino acid sequences of foreign epitopes to be expressed on the OB may further help to identify compatible structures in the polyhedrin protein which may be altered by recombinant DNA techniques. As an example, secondary structural analysis of the Autographa polyhedrin using the procedures of Chou and Fasman, supra, indicates that the region between amino acids 37–49 is primarily an alpha helical structure. Incorporating foreign peptides that are not alpha helical may alter the structure of surrounding regions and possibly disrupt crystallization. Similarly, the conformation of the surrounding regions may interfere with the proper folding of the foreign peptide domain and block the proper presentation of the epitope.

Chou-Fasman analysis of the hydrophilic amino terminus of the Autographa protein suggests that this region is involved primarily in the formation of a beta turn. This conformation provides some degree of structural flexibility for a new peptide inserted in this region. A new determinant incorporated at this site may not be forced into an intricate secondary structure and could possibly assume its native structure without interfering with the stability of the polyhedrin crystal.

In a similar fashion, polyhedrin molecules and the foreign epitopes proposed for insertion can be analyzed to determine secondary structures that are potentially compatible, resulting in recombinant OBs which express the foreign epitopes in their naturally antigenic conformations.

Other methods of structural analysis can also be employed to aid in identifying modifiable domains of the polyhedrin molecule. These include but are not limited to X-ray crystallography and computer modelling. X-ray crystallography (Engstom, A., 1974, Biochem. Exp. Biol. 11:7–13) can be used to analyze the domains of the polyhedrin protein which interact to form the paracrystalline lattice, and to confirm overall structures generated by computer modelling. Computer modelling (Fletterick, R. and Zoller, M. (eds.), 1986, Computer Graphics and Molecular Modeling, In Current Communications in Molecular Biology, Cold Spring Harbor Laboratory, New York) can provide theoretical three-dimensional images representing sequences comprising foreign epitopes, in an attempt to identify higher order structures that are compatible with the structure of the polyhedrin crystal.

PREPARATION AND CHARACTERIZATION OF MONOCLONAL ANTIBODIES TO OCCLUSION BODIES

The isolation and characterization of monoclonal antibodies to intact OBs or to recrystallized polyhedrin will identify regions of the polyhedrin protein that are exposed on the surface of the crystal. Once these regions are identified, it will be possible to test whether these domains can be altered without interfering with the integrity of the crystalline lattice.

The occlusion bodies of NPVs are surrounded by a carbohydrate envelope (Minion, F. C., et al., 1979, J. Invert. Pathol. 34:303) that may affect the immunogenicity of the OB. Therefore, in order to avoid such interference, monoclonal antibodies can be prepared to recrystallized polyhedrin, in addition to using the purified OBs. An 11S-13S polyhedrin aggregate can be purified from alkali solubilized occlusion bodies and recrystallized by standard techniques (Shigematsu, H., and Suzuki, S., 1971, J. Invert. Pathol. 17:375). Recrystallization results in a polyhedrin particle free of contaminating virions and carbohydrate.

OBs can be purified from a number of host cells by known techniques (for example, see Section 7.1.4. infra, and Tweeten, K. A., et al., 1981, Microbiol. Rev. 45:379–408). These host cells include, but are not limited to, cell lines and larvae in which the baculovirus can be propagated and produce OBs. For example, such cell lines include, but are not limited to, *Spodoptera frugiperda* IPLB-SF-21AE cells, *Heliothis zea* IPLBHZ-1075 cells, *Estigmene acrea* BTI-EAA cells, *Trichoplusia ni* TN-368 cells, *Trichoplusia ni* BTI-TN4BI, BTI-TN5F2, BTI-TN5F2P, and BTI-TN5F2A cells (Granados, R. R., et al., 1986, Virology 152:472–476), *Mamestra brassicae* Mb 0503, and Mb 1203 cells (Miltenburger, H. G., et al., 1976, Z. Angew. Entomol. 82(3):306–323); *Heliothis zea* BCIRL-HZ-AM1,2, or 3 cells (McIntosh, A. H. and Ignoffo, C. M., 1981, J. Invert. Pathol. 37:258–264); *Heliothis virescens* BCIRL-HV-AMI cells (id.); and their derivative cell lines. Infection of tissue culture cells can be accomplished by standard procedures known in the art (Smith, G., and Summers, M., 1979, J. Virol. 30:828). In a specific embodiment of the invention, *Spodoptera frugiperda* cells can be infected with *Autographa californica* MNPV at 1–2 pfu/cell. Polyhedrin protein can then be purified from OBs by techniques known in the art. For example, polyhedrin protein can be purified by incubating the purified occlusion bodies in 0.1 M $Na_2CO_3$ (pH 11), 0.17M NaCl, 1 mM EDTA, and spinning the dissolved protein at 24,000 rpm in an SW50.1 rotor for 30 minutes at 4° C. to remove virus particles and any insoluble material. The solubilized polyhedrin can be stored at −20° C. (Huang, Y. S., et al., 1985, Virology 143:380), and the homogeneity of the preparation can be determined by SDS polyacrylamide gel electrophoresis, among other methods.

Monoclonal antibodies to OBs or to recrystallized polyhedrin can be prepared by using any technique which provides for the production of antibody molecules by continuous cells in culture. These include, but are not limited to, the hybridoma technique originally described by Kohler and Milstein (1975, Nature 256:495), and the more recent human B cell hybridoma technique (Kozbor et al., 1983, Immunology Today 4:72) and EBV-hybridoma technique (Cole et al., 1985, Monoclonal Antibodies and Cancer Therapy, Alan R. Liss, Inc., pp. 77–96). In a specific embodiment of the invention, BALB/c mouse monoclonal antibodies can be prepared by use of a fusion protocol utilizing the BALB/c myeloma cell line, NS-1, and the fusagent, polyethyleneglycol 1000, as described by Ploplis et al. (Ploplis, V. A., et al., 1982, Biochemistry 21:5891). Hybridomas producing antibodies to OBs can be identified preferably by use of a solid-phase immunoassay with a labelled ligand, such as an enzyme-linked immunosorbent assay (ELISA) (as described, for example, by Ploplis, V. A., et al., supra).

Monoclonal antibodies generated to the OBs or to recrystallized polyhedrin can then be tested to ensure recognition of epitopes on the polyhedrin monomer. This can be accomplished by any immunoassay known in the art such as immunoprecipitation or radioimmunoassay, although a Western blotting procedure is preferable (Towbin, H., et al., 1979, Proc. Natl. Acad. Sci. U.S.A. 76:4350). For instance, purified polyhedrin can be denatured and reduced with a sample buffer containing SDS and B-mercaptoethanol. The denatured sample can then be electrophoresed through a gel, transferred to nitrocellulose, and incubated with the monoclonal antibody solution. The presence of an epitope on the monomeric polyhedrin molecule that can be recognized by a monoclonal antibody generated to the OB or to recrystallized polyhedrin, can then be detected by use of a second antibody, directed against the monoclonal antibody, conjugated to a label such as an enzyme or radioisotope. For example, horseradish peroxidase can be used, in which case visualization of the antigenantibody complex can be facilitated by using the enzyme substrate 4-chloro-1-naphthol.

IDENTIFICATION OF EPITOPES RECOGNIZED BY ANTI-POLYHEDRIN MONOCLONAL ANTIBODIES

Characterization of the epitopes recognized by antipolyhedrin monoclonal antibodies involves the study of polyhedrin-encoded peptides' interactions with the monoclonal antibodies. Peptides representing putative epitopes can be tested for antibody binding. The peptides for use in such tests can be generated by any method known in the art, including, but not limited to, protease digestion or chemical fragmentation of polyhedrin, chemical synthesis of peptides, or expression by recombinant DNA vector-host systems.

In a preferred embodiment of the invention, protease digestion of polyhedrin can be accomplished by use of V8 protease (Brown, M., et al., 1980, J. Gen. Virol. 50:309), although any protease known in the art such as trypsin, chymotrypsin, papain, or pepsin, among others, can be used. Peptides generated by protease digestion are preferably isolated by HPLC utilizing reverse phase chromatography, although any standard techniques which result in the purification of the peptides can be used. The peptides can then be assayed for antibody binding. Peptides that effectively compete with the intact protein for antibody binding possess the antigenic determinant recognized by the antibody. Any type of competitive immunoassay may be used, such as radioimmunoassays, and, preferably, ELISAs. Peptides that are determined to comprise the antigenic determinant can be sequenced by techniques known in the art, and their location in the polyhedrin protein determined by sequence analysis.

Chemical fragmentation of the polyhedrin protein can be accomplished, for example, by use of cyanogen bromide, partial acid hydrolysis, BNPS-skatole, N-bromosuccinimide, hydroxylamine, or other methods of specific cleavage.

In an alternative method for identification of the antigenic determinants, the identification of modifiable, hydrophilic (Hopp, T., and Woods, K., 1981, Proc. Natl. Acad. Sci. U.S.A. 78:3824) and/or hypervariable regions (see sections 5.1.1.1 and 5.1.1.2, supra) can pinpoint potential antigenic sites. Small peptides that correspond to the putative epitopes can be chemically synthesized, for example, by the Merrifield solid phase method (Merrifield, R. B., 1963, J. Am. Chem. Soc. 85:2149). These peptides can then be analysed for cross-reactivity with the monoclonal antibody as described supra.

Another way in which to pinpoint potentially modifiable regions of the polyhedrin protein which can then be synthesized and tested for competitive antibody binding, is to identify species-specific epitopes. Monoclonal antibodies directed toward an OB antigenic determinant can be analyzed for crossreactivity to other polyhedra species. This can be most easily accomplished by an ELISA method although other immunoassays including, but not limited to, Western blotting, immunoprecipitation, and radioimmunoassays are within the scope of the invention. Species-specific epitopes exposed on the surface of the crystal represent potentially modifiable regions of the polyhedrin protein. Some such species-specific monoclonal antibodies to OBs have been described (Huang, Y. S., et al., 1985, Virology, 143:380), suggesting that there are epitopes which can be varied on the occlusion body surface.

Another method for mapping epitopes on the polyhedrin protein is by comparing poteolytic digests of polyhedrin in the presence and absence of the monoclonal antibody. It has been shown that epitopes are protected from proteolysis in the presence of their respective antibodies (Jemmerson, R., and Paterson, Y., 1986, BioTechniques 4:18). Protease-digested fragments can be generated by known methods in the art, including, but not limited to, the use of proteases such as trypsin, chymotrypsin, V8 protease, papain, pepsin, etc. Protease-generated peptides can be identified by various techniques, including, but not limited to, reverse-phase chromatography and two-dimensional gel electrophoresis. In a preferred embodiment of the invention, tryptic peptides of polyhedrin can be identified using reverse-phase chromatography. The digestion patterns of a nonspecific immunoglobulin molecule, digested in the presence of polyhedrin, can also be determined, in order to identify those peptides which are derived from the immunoglobulin molecule that have retention times, electrophoretic migrations, or other characteristics that are similar to those of the polyhedrinderived peptides. The thus identified polyhedrin-specific and immunoglobulin-specific digestion patterns can be compared to the digestion patterns obtained from the polyhedrinantipolyhedrin complex. Presumably, the antibody will protect some proteolytic cleavage sites and reduce the recovery of peptides containing the epitope. These peptides, putatively comprising the epitope, can be isolated and characterized by sequence analysis. Due to probable steric hindrance of the antibody on overall proteolysis of the protein, this procedure could potentially identify some peptides which are not involved in antibody binding. Therefore, a variety of other proteases can be used. Such proteases include, but are not limited to, trypsin, chymotrypsin, V8 protease, papain, and pepsin. Comparing the results generated by several proteases will identify the region containing the epitope. This method has proven to be effective in mapping conformational dependent epitopes that cannot be easily mimicked by synthetic peptides (Jemmerson, R., and Paterson, Y., 1986, BioTechniques 4:18).

IDENTIFICATION AND CHARACTERIZATION OF IMMUNODOMINANT PEPTIDES FOR EXPRESSION ON OR WITHIN RECOMBINANT OBs

In one embodiment of the invention, the generation of recombinant OBs which contain one or more foreign antigenic determinants, for use in vaccine formulations or immunoassays, requires the identification and characterization of specific antigenic determinants which may be used in constructing recombinants. For use in vaccine formulations, a peptide or protein should be identified which encodes an immunopotent sequence of a pathogenic microorganism. In other words, the peptide should be capable of eliciting an immune response against a pathogen. In addition, molecules which are haptens (i.e. antigenic, but not immunogenic) may also be used, since the polyhedra functions as a carrier molecule in conferring immunogenicity on the hapten. (For a further discussion of peptides which may be exposed on or within recombinant OBs, see Section 5.4.1., infra.) Peptides containing epitopes which are reactive with antibody although incapable of eliciting immune responses, even when exposed on recombinant OBs, still have potential uses in immunoassays (see Section 5.4.4., infra).

Peptides or proteins which are known to encode antigenic determinants can be incorporated into recombinant polyhedra. If specific antigens are unknown, identification and characterization of immunoreactive sequences should be carried out. One way in which to accomplish this is through the use of monoclonal antibodies generated to the surface molecules of the pathogen. Such a technique has been used to help identify and characterize the major epitopes of myoglobin (Berzofsky, J. A., et al., 1982, J. Biol. Chem. 257:3189), lysozyme (Smith-Gill, S. J., et al., 1982, J. Immunol. 128:314), and influenza hemagglutinin (Wilson, I. A., et al., 1984, Cell 37:767). The peptide sequences capable of being recognized by the antibodies are defined epitopes. These peptide sequences can be identified, for example, by virtue of the ability of small synthetic peptides containing such sequences, to compete with the intact protein for binding of monospecific antibodies. Alternatively, small synthetic peptides conjugated to carrier molecules can be tested for generation of monoclonal antibodies that bind to these sites, encoded by the peptide, on the intact molecule. Such an approach has been used for the recognition of an immunodominant peptide determinant in the influenza hemagglutin protein (Wilson, I.A., et al., 1984, Cell 37:767). Other methods which may be employed for the identification and characterization of antigenic determinants are also within the scope of the invention. These include, but are not limited to, protease protection experiments such as described in Section 5.1.1.5.1, supra. In this technique, epitopes are identified by their protection from proteolysis in the presence of their respective antibodies.

CONSTRUCTION OF RECOMBINANT POLYHEDRIN GENES

Once modifiable, and preferably surface, regions of the polyhedrin protein have been identified, all or part of the corresponding segments of the gene can be replaced with sequences encoding one or more foreign epitopes. Many strategies known in the art can be used for this purpose, provided the antigenicity of the heterologous sequence and the ability of the polyhedrin to form an occlusion body are not destroyed. The relevant sequences of the polyhedrin gene and of the heterologous gene can, by techniques known in the art, be cleaved at appropriate sites with restriction endonuclease(s), isolated, and ligated in vitro. If cohesive termini are generated by restriction endonuclease digestion, no further modification of DNA before ligation may be needed. If, however, cohesive termini of the polyhedrin DNA are not available for generation by restriction endonuclease digestion, or different sites other than those available are preferred, any of numerous techniques known in the art may be used to accomplish ligation of the heterologous DNA at the desired sites. For example, cleavage with a restriction enzyme can be followed by modification to create blunt ends by digesting back or filling in single-stranded DNA termini before ligation. Alternatively, the cleaved ends of the polyhedrin or heterologous DNA can be "chewed back" using a nuclease such as nuclease Bal 31, exonuclease III, lambda exonuclease, mung bean nuclease, or T4 DNA polymerase exonuclease activity, to name but a few, in order to remove portions of the sequence. An oligonucleotide sequence which encodes one or more restriction sites that are unique to the polyhedrin gene sequence and/or to the baculoviral genome itself can be inserted in a region of the polyhedrin gene that is nonessential for crystallization (hereinafter this oligonucleotide linker will be referred to as a polylinker). The polylinker can be inserted into the polyhedrin sequence by in vitro techniques such as those discussed supra. The resulting recombinant gene is akin to a "cassette vector" into which any heterologous gene can be inserted using appropriate restriction enzymes. In this embodiment, it is beneficial to insert a polylinker sequence within the polyhedrin gene so that the interrupted polyhedrin sequence is no longer in the correct translational reading frame, in which case the recombinant virus containing the cloning sites will be OB−. The subsequent ligation of a heterologous gene into the cloning site located within the region of the polyhedrin gene sequence that is non-essential for crystallization, so that both sequences are in the correct translational reading frame uninterrupted by translational stop signals, will result in a construct that directs the production of a fusion polyhedrin protein that will crystallize and form recombinant occlusion bodies. A polylinker may also be used to generate suitable sites in the heterologous gene sequence. Additionally, polyhedrin or heterologous gene sequences can be mutated in vitro or in vivo in order to form new restriction endonuclease sites or destroy pre-existing ones, to facilitate in vitro ligation procedures. Any technique for mutagenesis known in the art can be used, including but not limited to, in vitro site-directed mutagenesis (Kunkel, 1985, Proc. Natl. Acad. Sci. 82:488–492; Hutchinson, C., et al., 1978, J. Biol. Chem. 253:6551), use of TAB ® linkers (Pharmacia), etc.

The particular strategy for constructing gene fusions will depend on the specific polyhedrin sequence to be replaced or inserted into, as well as the heterologous gene to be inserted. The discussion infra relates several strategies by which manipulation of restriction sites of the polyhedrin gene for in vitro recombination purposes may be accomplished, and is intended for descriptive purposes only. Many other recombination strategies are within the scope of the invention.

One specific embodiment of the invention is a strategy for replacing the region of the AcMNPV polyhedrin gene encoding amino acids 37–49 with oligonucleotides encoding an epitope of influenza hemagglutinin. There is a BamHI site within the polyhedrin structural gene at the sequence encoding amino acid 58. A deletion strain can be constructed by cleavage with BamHI followed by digestion with exonuclease Bal 31, and ligation to a synthetic BamHI polylinker. In this way, we constructed a deletion strain in which DNA sequences encoding amino acids 35 through the BamHI site were replaced with a synthetic BamHI linker. The plasmid containing this gene can then be cut at the BamHI site, "blunt-ended" with either S1 or mung bean nucleus, and ligated to the termini of the following synthetic oligonucleotide:

Lys His Phe Ala Leu Asp Asn Tyr Leu Val Ala Glu Asp
5' AAG CAC TTC GCG AGA TCTA GAC AAC TAC CTA GTG GCT GAG GATC
3' TTC GTG AAG CGC TCT AGAT CTG TTG ATG GAT CAC CGA CTC CTAG
Nru I  BglII  Xba I

The synthetic oligonucleotide is thus inserted into the polyhedrin gene, and, by virtue of its encoded unique restriction sites, makes more cleavage sites available for recombination purposes. The clone thus generated contains the AcMNPV polyhedrin gene from the amino terminus to amino acid 37, the oligonucleotide with unique NruI, BglII, and XbaI sites, and the polyhedrin coding sequence from amino acid 50 through the BamHI site at amino acid 58. Once this clone is generated, additional sequences can be inserted into the unique NruI, BglII, or XbaI sites, that would restore the translational reading frame and encode antigenic determinants of foreign proteins, such as an epitope of a pathogenic microorganism. As one example, cloning the following oligonucleotide:

Tyr Pro Tyr Asp Val Pro Glu Tyr Ala
5' - CG TAT CCG TAC GAT GTA CCG GAT TAC GCT
3' - GC ATA GGC ATG CTA CAT GGC CTA ATG CGA GATC into the NruI and XbaI sites would generate a gene fusion in which the influenza hemagglutinin epitope extending from amino acid 98–106 would be inserted in frame between amino acids 38 and 50 of the Autographa polyhedrin gene.

Alternative strategies for inserting the foreign oligonucleotide include, but are not limited to, insertion of a BglII site at amino acid 43 by changing nucleotide 127 of the Autographa polyhedrin gene from a G to a T by in vitro mutagenesis (Kunkel, 1985, Proc. Natl. Acad. Sci. 82:488–492; Hutchinson, C., et al., 1978, J. Biol. Chem. 253:6551). Synthetic oligonucleotides can then be inserted between the unique BglII and BamHI sites. Thus, many gene fusions can be generated, adding new antigenic determinants and deleting as much of the region between the BglII and the BamHI sites as desired. A DNA synthesizer (e.g., Applied Biosystems Model 380A) may be used to generate a large variety of constructs. A method for preparing this type of construct is described in detail in Section 11 infra.

Similar strategies may be used to recombine other regions of the polyhedrin gene. In vitro mutagenesis followed by insertion of synthetic polylinkers can enable manipulation of most, if not all, of the regions of the polyhedrin gene.

In another particular embodiment of the invention, a strategy can be employed to insert foreign DNA within the polyhedrin gene at a particular restriction site, which may or may not be a unique restriction site. In this embodiment, single-stranded DNA of the polyhedrin gene of a recombinant vector is manipulated to produce site-specific cleavage at a specific restriction site. (For an example using this strategy, see Section 10.1., infra). Single-stranded DNA from the polyhedrin gene is isolated. This can be accomplished by many standard techniques such as heat-denaturation of the double-stranded form followed by fractionation, or preferably, by isolating the single-stranded DNA of a vector such as a bacteriophage derivative (e.g. an M13 phage, a phagemid) which contains the polyhedrin DNA inserted within its genome. Specific cleavage at a particular restriction site within the DNA is accomplished by annealing a complementary synthetic oligonucleotide (oligo-1) to the single-stranded DNA, before restriction digestion. This annealing creates the requisite double-stranded region for recognition and cleavage by the restriction endonuclease. After cleavage, the single-stranded linear DNA can then be isolated by known techniques (e.g. heat denaturation and column chromatography). An oligonucleotide with a sequence encoding a foreign epitope can also be synthesized (termed hereinafter oligo 2). Another oligonucleotide can then be synthesized (termed hereinafter oligo 3) which is complementary to oligo 2 and which, in addition, has 5' and 3', termini which extend beyond oligo 2 which are complementary to the singlestranded termini of the polyhedrin DNA. Olig 2 and oligo 3 can then be annealed together, followed by ligation of the duplex to the single-stranded polyhedrin DNA. Transformation of a suitable vector host such as E. coli will produce a recombinant transfer vector which contains the DNA encoding a foreign peptide inserted at a specific restriction site within the polyhedrin gene.

Irrespective of the manner of constructing the recombinant polyhedrin gene, transfer of the gene fusion into the baculovirus can be accomplished by homologous recombination in vivo between viral DNA and DNA sequences containing the fusion. In a preferred embodiment, such DNA sequences are contained in a transfer vector such as a plasmid (Pennock, G., et al., 1984, Mol. Cell. Biol. 4:399; Smith, G., et al., 1983, Mol. Cell. Biol. 3:2156). The transfer vector can be constructed to contain the heterologous gene inserted within the polyhedrin gene sequence and flanked by baculoviral sequences adjacent to the viral polyhedrin gene. This can be accomplished by DNA recombination involving the use of standard techniques in molecular biology (Maniatis, T., et al., 1982, Molecular Cloning, A Laboratory Manual, Cold Spring Harbor Laboratory, New York). Parental baculoviral DNA plus transfer vector DNA can be cotransfected into cells susceptible to infection, where in vivo recombination will then take place, producing the recombinant virus of the invention. The transfections can be accomplished by any procedures known in the art, including, but not limited to, the calcium-phosphate precipitation method (see, for example, Smith, G., et al., 1983, J. Virol. 46:584), treatment with polybrene and dimethyl sulfoxide (Kawai, S. and Nishizawa, M., 1984, Mol. Cell. Biol. 4:1172), or electroporation (e.g., Kuta, A. E., Rhine, R. S. and Hebner, G. M., 1985, "Electrofusion-A New Tool for Biotechnology", Amer. Biotech. Lab. 3:31-37). In another embodiment, a cassette vector can be constructed which comprises a polylinker sequence inserted within a region of the polyhedrin gene that is nonessential for crystallization. This recombinant polyhedrin gene can then be transferred to a baculovirus by in vivo recombination within baculovirus-infected cells, producing a "cassette-expression" virus. The genome of this cassette-expression virus can be isolated for in vitro recombination purposes, in which insertion or replacement of polyhedrin regions which are nonessential for crystallization, by a heterologous sequence, is facilitated by virtue of the polylinker.

SELECTION OF RECOMBINANT OCCLUSION BODIES

As explained supra, baculoviruses that produce recombinant occlusion bodies may be constructed via recombination by replacing or interrupting regions of the polyhedrin gene sequence, that are nonessential for crystallization, with the heterologous gene sequence so that the sequences are not interrupted by translational stop signals. Since the gene products of these recombinants will be expressed as recombinant occlusion bodies, it is preferred to use an OB- parent baculovirus strain, in order to select OB+ virus plaques against an OB- background. Viruses generating OBs can be detected in plaque assays among the large number of parental viruses which fail to make OBs, since OB+ viruses form more refractile plaques than OB- viruses. Alternatively, an OB+ background would be preferred where the recombinant OBS form plaques that are less refractile than those formed by wild type viruses. For instance, the recombinant OBs expressed by InHem-43 and InHem-50 detailed in the Examples, infra (see Section 11 et seq) are morphologically very different from wild type occlusion bodies. These recombinants were found to produce cuboidal occlusion bodies that express the foreign epitope. The cuboidal recombinant OBs, formed placques which were less refractile than those produced by wild type virus. Therefore, the recombinant OBs were easily selected against an OB+ background.

Selection can also be done on the basis of physical, immunological, or functional properties of the inserted heterologous gene product. For example, an enzyme-linked immunosorbent assay (ELISA) can be used to detect expression of a foreign antigenic determinant. If a heterologous gene has been incorporated that encodes an enzyme, selection may be done on the basis of enzymatic activity. Staining techniques based on chemical reactivity of the foreign peptide may be used. Many other techniques known in the art can be used, depending on the foreign sequence expressed, and are within the scope of the invention.

While attempting to select recombinant viruses that produce recombinant occlusion bodies, whether the selection is against an OB- or OB+ background, it is possible to employ other markers which aid in selection. For example, a second gene, encoding a selectable marker, can also be introduced into a region of the baculovirus genome which is not essential for crystallization. Prior to transfer to the baculovirus genome, the selectable marker may exist as a totally distinct DNA fragment or, preferably may be contained in adjacent sequences of the transfer vector containing the recombinant polyhedrin gene. The selectable marker should be cotransfected with the recombinant polyhedrin gene into the baculovirus where in vivo recombination will occur. OB+ recombinants which also express the selectable marker can then be selected. Many cloned genes known in the art can be used as the selectable marker, including, but not limited to, genes encoding enzymes such as beta-galactosidase, which have standard procedures for selection.

Another method for selection is to screen for presence of the heterologous DNA sequence inserted into the polyhedrin gene. This can be accomplished by techniques known in the art, such as nucleic acid hybridization to replica plaques (Benton, W. D. and Davis, R. W., 1977, Science 196:180), and variations thereof.

Another technique known in the art which may be used for selection is loss of a marker gene activity through inactivation or replacement of the marker gene. In this embodiment, parental baculoviruses can be constructed which contain a selectable marker flanked by sequences homologous to those surrounding the recombinant polyhedrin. For example, a parental baculovirus can be constructed containing a beta-galactosidase gene downstream of the polyhedrin promoter. In vivo recombination between the recombinant polyhedrin gene and the constructed parental strain will result in insertion of the recombinant polyhedrin gene by virtue of its homologies with the parental polyhedrin sequences surrounding the betagalactosidase gene. The recombination which results in insertion of the recombinant polyhedrin gene and inactivation or replacement of the beta-galactosidase gene may be selected for by the lack of beta-galactosidase activity by known methods (Messing, J., et al., 1977, Proc. Natl. Acad. Sci. U.S.A. 74:3642). This selection can be accomplished against an OB− or OB+ background as previously described.

A control selection experiment which may be done is to cotransfect with wild-type viral DNA (OB+) in order to detect, among the wild-type progeny, recombinants failing to make OBs. Although the identification and characterization of the recombinant generated in this type of cotransfection represents a negative result, it will provide valuable information regarding what modifications of the polyhedrin gene interfere with lattice formation and are therefore unsuitable for the practice of the present invention.

VERIFICATION OF EXPRESSION OF FOREIGN EPITOPES ON OR WITHIN THE RECOMBINANT OCCLUSION BODY

After selection for recombinant OBs, the OBs should be isolated (see, for example, Section 7.1.4., infra and Tweeten, K. S., et al. 1981, Microbiol. Rev. 45:379–408) and analysed for the expression of the foreign epitope.

OBs can be purified by any standard technique (for example, see Section 7.1.4., infra, and Tweeten, K. A., et al., 1981, Microbiol. Rev. 45:379–408). In one embodiment, monoclonal antibodies directed against the recombinant polyhedrin protein can be used as an effective means of purifying the polyhedrin protein. As an example, isolated preparations of recombinant OBs can be solubilized, the recombinant polyhedrin protein purified by immunoaffinity chromatography (Goding, J. W., 1983, Monoclonal Antibodies: Principles and Practice, Ch. 6, "Affinity Chromatography Using Monoclonal Antibodies", *Academic Press, Inc.*, London, pp. 188-207) and then recrystallized to form a purified preparation of recombinant OBs. This method requires an antigen that remains capable of binding to antibody even after the stringent conditions necessary for crystal dissolution.

The foreign gene product can be analyzed by assays based on physical, immunological, or functional properties of the product. Immunological analysis is especially important where the ultimate goal is to use the recombinant OBs that express the product in vaccine formulations and/or as antigens in diagnostic immunoassays. Antibodies to the peptide, preferably monoclonal, can be tested for their ability to interact with the crystalline recombinant polyhedrin. This can be accomplished by various techniques known in the art including, but not limited to, an enzyme-linked immunosorbent assay (ELISA) method (for example, a solid-phase binding assay on polyvinyl chloride plates), or a radioimmunoassay. Methods known in the art such as western blotting or immunoprecipitation procedures can be used to determine the presence of the peptide on the polyhedrin monomer.

VECTOR/HOST SYSTEMS

Any baculovirus may be used as the parent for construction of the recombinant baculoviruses of the present invention. These vectors include but are not limited to NPVs and GVs. For example, NPVs which may be used in accordance with the present invention include but are not limited to AcMNPV, HzSNPV, *Heliothis virescens* NPV, *S. littoralis* NPV, *Rachoplusia ou* MNPV, *Galleria mellonella* MNPV, *Lymantria dispar* MNPV, *Bombyx mori* SNPV, *Orygia pseudotsugata* SNPV and MNPV, *Orygia leucostigma* NPV, *Choristoneura fumiferana* MNPV, *Pseudohazis eglanterina* SNPV, *N. sertifer* SNPV, *T. paludosa* SNPV, *Trichoplusia ni* MNPV, and *Spodoptera frugiperda* MNPV (Vlak, J. M. and Rohrmann, G. F., *supra*). GVs which may be used in accordance with the present invention include but are not limited to *P. brassicae* GV, *Estigmene area* GV, *Choristoneura vindis* GV, *Plodia interpunctella* GV, *Choristoneura vindis* GV, *Plodia interpunctella* GV, *T. ni* GV, *Choristoneura murinana* GV, *Cirphis unipuncta* GV, *L. pomonella* GV, *Cydia pomonella* GV, *Mamestra oleracea* GV, *Pseudaletia unipuncta* GV, *Pygera anastomosis* GV, *S. frugiperda* GV, *Zeiraphera diniana* GV, and *Choristoneura fumiferana* GV (Vlak, J. M. and Rohrmann, G. F., *supra;* Tweeten, K. A., et al., 1981, Microbiol. Rev. 45:379–408).

In a preferred embodiment, a plaque-purified isolate with a homogeneous genotype should be used as the parent baculovirus. Moreover, a recombinant baculovirus can be constructed from parent viruses which possess particularly advantageous properties with respect to the host systems used in accordance with the present invention. For example, viruses which demonstrate high infectivity and high virus titers in the host system are preferred.

When using larvae host systems, viruses which do not cause melanization are preferred. Melanization is a normal response to viral infection which comprises the production of melanin, a pigment which is incorporated into the insect's cuticle, and appears to involve the polymerization of indol ring compounds derived by oxidation of tyrosine (Wigglesworth, V. B., 1974, in The Principles of Insect Physiology, Chapman and Hall, London, p. 610). The tyrosinase which is involved in the melanization process appears to be abundant in the hemolymph of the insect and can react fairly non-specifically with available proteins. Thus, the tyrosinase activity in an insect carrying the recombinant baculoviruses of the invention may non-specifically metabolize the recombinant polyhedrin protein, interfering with and decreasing the yield and purity of the recombinant product. Melanization of occlusion bodies can cause subsequent chemical alteration of virion proteins and nucleic acids. Melanization can also severely reduce infectious extracellular virus titers in collected hemolymph, as well as poison cultured cells following inoculation. Thus non-melanizing or slow-melanizing host strains are preferred in order to avoid these problems.

In the discussion that follows, parent vectors and cell lines are discussed in terms of *Heliothis zea* SNPV and *Heliothis zea* cell lines. It should be noted that this discussion is for descriptive purposes only and the scope of the invention includes many other baculoviruses, such as GVs and other NPVs.

In a specific embodiment, *Heliothis zea* SNPV may be used as the parent virus strain. Restriction digestion patterns of eight different geographic isolates of HzSNPV suggest each is a separate population of viruses having a slightly different predominant genotype, but none represents a totally unique virus species (Gettig and McCarthy, 1982, Virology 117:245-252). Seven of the eight geographical isolates examined have similar major occluded virus structural protein profiles in SDS-polyacrylamide gel electrophoresis (SDS-PAGE) (Monroe and McCarthy, 1984, J. Invert. Path. 43:32-40). Even though the eight Heliothis SNPV isolates are genetically and biochemically similar, several isolates exhibit significant differences in virulence towards *H. zea* larvae (Gettig and McCarthy, 1982, Virology 117:245-252).

We have thus far analyzed plaque purified strains derived from the Elcar TM isolate of HzSNPV (originally isolated by Dr. J. J. Hamm, U.S.D.A., Tifton, Ga.). We characterized the genotypic and phenotypic heterogeneity of the Elkar TM isolate by comparing restriction enzyme digestions of viral genomes, SDS-PAGE profiles of occluded virus structural proteins, and differences in larval pathology among the plaque-purified strains.

After purifying and analyzing 20 strains from the Elcar TM isolate we found no single predominant genotype. Each strain could be distinguished using one or more restriction enzymes, and none was identical to the molar restriction pattern of the wild-type isolate. The inability to identify a predominant genotype indicated that this virus is highly variable.

We have localized a major region of variability to between 23.4 and 43.4 map units. This region includes HindIII fragments G, H, M, and N (see FIG. 6). At least 15 of the twenty plaque-purified strains diverge from the wild-type strain in this region, with alterations in one or more of these HindIII fragments.

When working with HzSNPV in larvae host systems it is advantageous to time the infection carefully to avoid melanization of either virion containing hemolymph or occlusion bodies, and to use a slow or non-melanizing strain of virus. Since melanization is a constant problem when studying the biochemistry of HzSNPV, the non-melanizing strains described herein are preferred for use in larval host systems in this specific embodiment of the invention. In particular, strains 5, 7, 8, 9, 21, 22, 24 and 25 described infra (See Section 7, in particular, Table II) cause slow melanization. In a preferred embodiment, strain HzS-15, (also described in Section 7 infra) which causes extremely slow melanization can be used as the parent strain for constructing recombinant Heliothis viruses for use in larval host systems.

The genotype map of the HzS-15 strain (see FIGS. 7 and 8) differs from the wild-type map (Knell and Summers, 1984, J. Gen. Virol. 65:445-450) in the hypervariable region. The divergence in this strain is evident with the enzymes EcoRI, HindIII, and SstI. Comparison of the maps of HzS-15 with those of the wild-type isolate shows that the divergence is caused by changes in the relative positions of several restriction sites, rather than in overall genome size or apparent organization.

The region of hypervariability in HzSNPV is not restricted to the Elcar strain. Reexamination of Gettig and McCarthy's (1982) study of geographic variation reveals that this window of hypervariability exists in other Heliothis species SNPVs. In addition, many HindIII fragments that are conserved among our plaque-purified isolates are also conserved among the previously analyzed geographic variants. This is especially true of HindIII fragments A, B, C, L, M, and O, all of which appear in 7 out of 8 geographic variants and in 13 out of 20 of the present isolates. Whether or not the high degree of variability found in the Heliothis spp. SNPVs confers advantages to the virus population under different geographic conditions remains to be determined (Gettig and McCarthy, 1982, Virology 117:245-252).

The restriction enzyme map of HzS-15 (FIGS. 7 and 8) substantially confirms the previous map of Knell and Summers (1984, J. Gen. Virol. 64:445-450). While we found no evidence of major errors in the position of SstI or BamHI restriction sites, we did find that one alteration of band position was necessary in the SstI map of the wild-type isolate. Band hybridization was not employed in this analysis, but we were able to confirm the relative position of most restriction sites with a high degree of certainty using cloned PstI or BamHI fragments.

Working with the HzS-15 plaque-purified isolate, we obtained a slightly different estimation of the overall genomic size. Our estimate of genome size based upon double digests and analysis of individual cloned fragments is approximately 131 kb, rather than the 120 kb previously reported (Knell and Summers, 1984, supra). Since we found little difference in the restriction maps outside of alterations in position of restriction sites, we feel that our estimate is a closer approximation of HzSNPV genome size.

Figure 9:
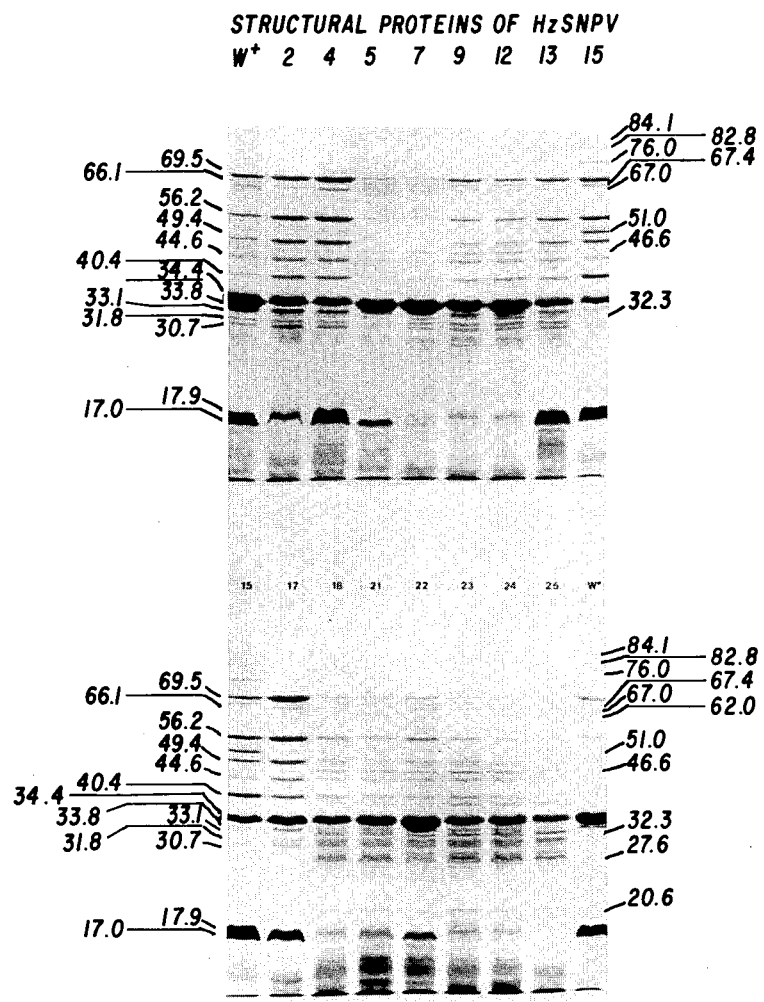
FIG. 9. Structural proteins of HzSNPV Elcar TM isolate and plaque purified strains. Sucrose gradient purified virions were electrophoresed for 4.5 hours on a 12% SDS-polyacrylamide gel The position and size of major wild-type proteins are labeled on the left, while unique proteins found in several of the plaque-purified strains are labeled on the right.

The variability between isolates is not limited to the genotype, but is also reflected in the structural proteins of the virions (see FIG. 9). We observed differences between isolates in several of the occluded virus proteins. In fact, there were more differences between these plaque-purified isolates from the single Elcar TM strain than were observed between several different geographical isolates of HzSNPV (Monroe and McCarthy, 1984, J. Invert. Path. 43:32-40).

The exact reason for the differences in rate of melanization may be related to the relative ability of individual strains to lyse cells, or in some tissue tropism. Evidence that cell lysis may be responsible for the differences in larval melanization response comes from freeze-thaw experiments with larvae infected with the nonmelanizing strain, HzS-15. Unmelanized HzS-15 infected larvae will quickly melanize following freezing and thawing. Preliminary cell culture data also supports this hypothesis, but further work is required to confirm that cell lysis is the predominant factor.

HOSTS USED IN THE VECTOR/HOST SYSTEMS

The recombinant baculoviruses of the present invention can be used to direct the expression of the heterologous gene product in a number of host systems including but not limited to cell lines and larvae in which the virus can be propagated. Some useful cell lines and larval systems which can be used in accordance with the invention are described in the subsections below.

INSECT CELL LINES

Any insect cell line in which the baculovirus can be propagated can be used in the procedures of the present invention. Such cell lines include but are not limited to IPLB-SF-21AE (*Spodoptera frugiperda* cells); TN-368, BTI-TN4BI, BTI-TN5F2, BTI-TN5F2P, BTI-TN5F2A (*Trichoplusia ni* cells; Granados, R. R., et al., 1986, Virology 152:472–476); ILPB-HZ1075 (*Heliothis zea* cells; Goodwin, R. H., et al., 1982, In Vitro Cell. Dev. Biol. 18:843–850); BCIRL-HZ-AM1,2, or 3 (*Heliothis zea* cells; McIntosh, A. H. and Ignoffo, C. M., 1981, J. Invert. Pathol. 37:258–264); BCIRL-HV-AM1 (*Heliothis virescens* cells; id.); BTI-EAA (*Estigmene area* cells); Mb 0503, Mb 1203 (*Mamestra brassicae* cells) (Miltenburger, H. G., et al., 1976, Z. Angew. Entomol. 82(3):306–323); and cell lines derived from these lines, etc.

For an informative discussion of the in vitro replication of baculoviruses, see Volkman, L. E. and Knudson, D. L., 1986, "In Vitro Replication of Baculoviruses, in The Biology of Baculoviruses, Vol. I, Biological Properties and Molecular Biology, Granados, R. R. and B. A. Federici, eds., CRC Press, Florida, which is incorporated by reference herein.

In the discussion which follows, cell lines for use in a specific embodiment of the invention involving HzSNPV and Heliothis cell lines is described, which is intended for descriptive purposes only, and in no way limits the scope of the invention.

The in vitro propagation of most SNPVs has been difficult to achieve. The IPLB-HZ1075 cell line, which was originally established by Goodwin (Goodwin, R. H., et al., 1982, In Vitro Cell. Dev. Bio. 18:843–850) from larval ovaries and fat body of the cotton bollworm, *Heliothis zea*, can support the growth of HzSNPV. However, numerous reports have demonstrated that 100% infection is difficult to routinely achieve with this system (Granados, R. R., et al., 1981, Intervirology 16:71–79; Yamada, K., et al., 1982, J. Invert. Path. 39:185–191). It is more common to obtain only 50 to 70% infection as measured by the presence of intranuclear OBs; thus, the usefulness of this system for analysis of HzSNPV replication processes is severely limited. In an effort to increase the productivity of HzSNPV in vitro, some investigators have established new cell lines from *Heliothis zea* (Goodwin et al., *supra*; McIntosh, A. H., et al., 1985, Intervirology 23:150–156). McIntosh and Ignoffo (1981, J. Invert. Pathol. 37:258–264) have demonstrated replication of HzNPV, with production of OBs, in cell lines derived from *Heliothis zea* or *Heliothis virescens*.

During routine subculturing of the HZ1075 cell line (Goodwin et al., 1982, In Vitro Cell. Dev. Bio. 18: 843–850), we frequently observed clonal outgrowth of cells having similar morphologies. This observation led us to consider the possibility that this cell line is highly heterogeneous, and that perhaps not all cells of the population were equally susceptible to infection with HzSNPV. We reasoned that isolation and characterization of subclones might provide a cell strain which would be more susceptible and produce more occlusion bodies upon infection with HzSNPV.

In the specific embodiments of the examples herein, we describe the isolation and characterization of clonal cell strains derived from the IPLB-HZ1075 insect cell line which can be used in the practice of the present invention. These strains exhibited different growth characteristics, morphologies, and productivities of HzSNPV, which are defined herein. We also utilized isozyme markers to characterize the cell strains and demonstrate that they are all derived from *Heliothis zea*.

Figure 10:
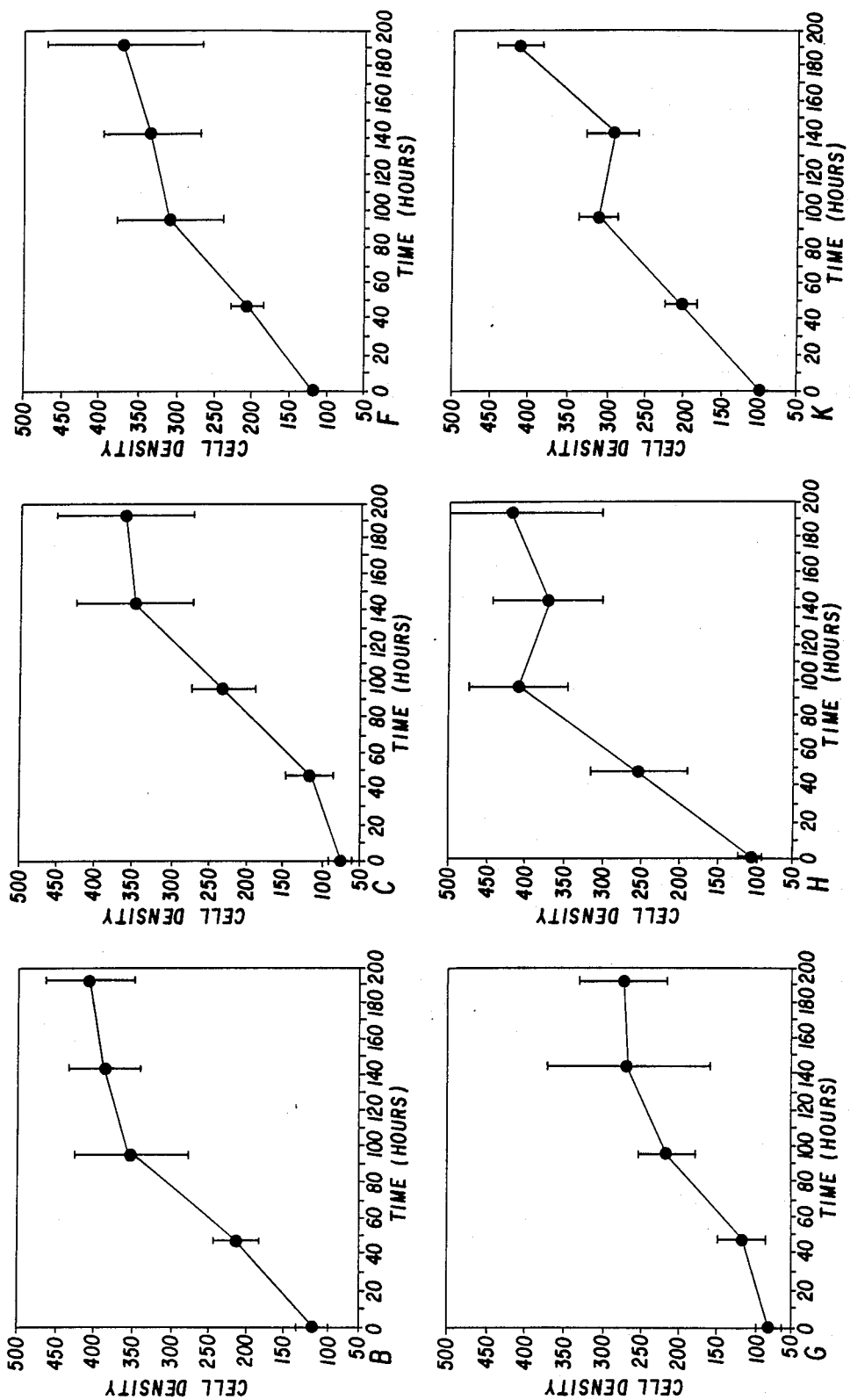
FIG. 10. Cell growth curves for clonally isolated cell strains derived from IPLB-HZ1075. Three defined regions of a tissue culture flask (25 cm$^2$) were counted at 48 hour intervals for a total of 8 days. Points on the graphs represent the average of the three counted areas with the error bars indicating 1 standard deviation. Letters in the lower left corner of each graph correspond to the nomenclature of the specific cell strain.
Figure 10:
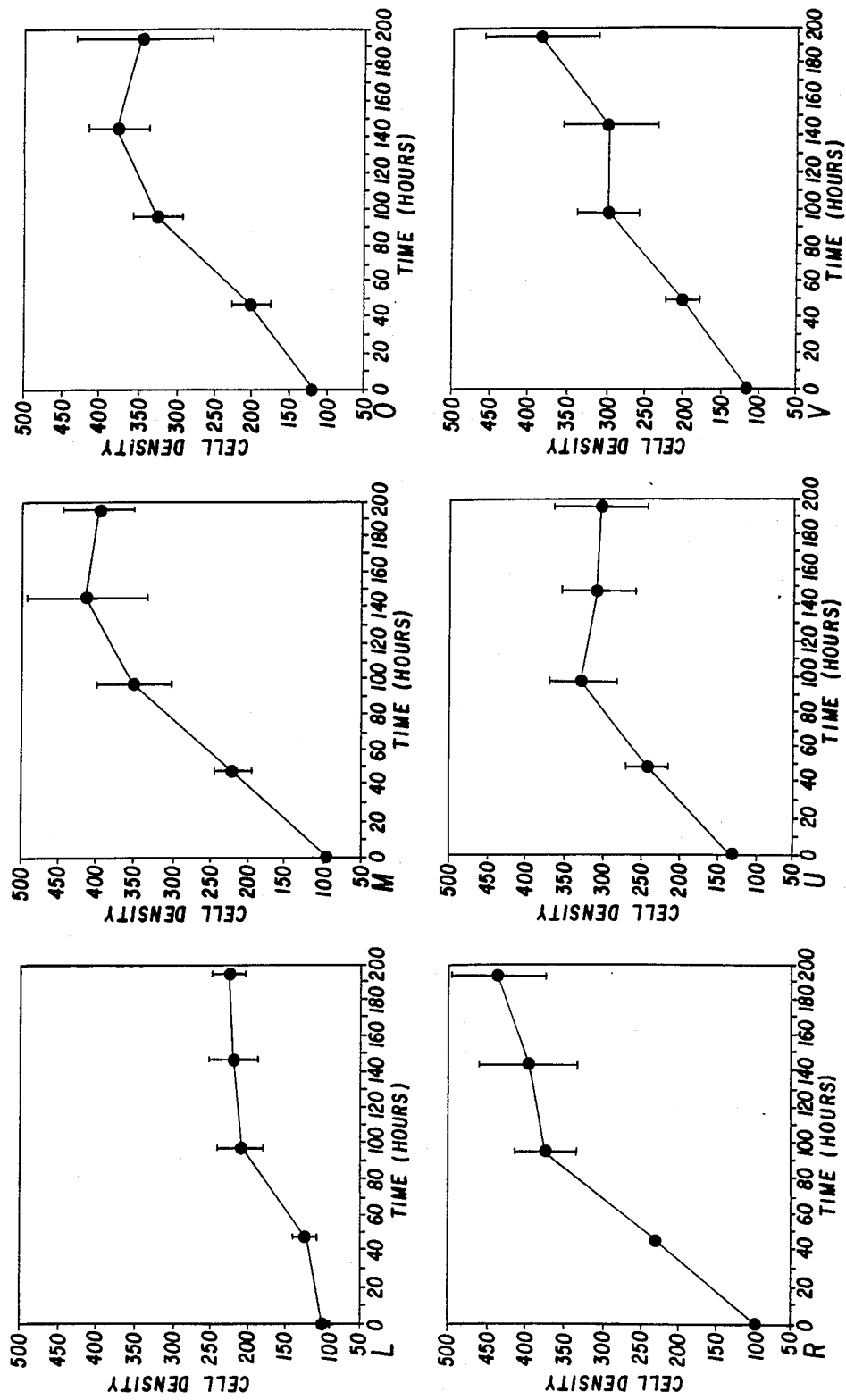
Figure 12A:
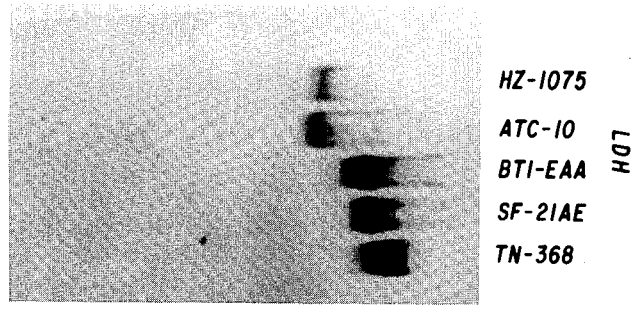
FIG. 12. Comparison of isozyme banding patterns for several insect cell lines. Cell lines prepared as described were electrophoresed in a 5% polyacrylamide gel (95% acrylamide, 5% Bis-acrylamide) in TC buffer. LDH separates IPLB-HZ1075 from all other cell lines; however, ATC-10 and IPLB-HZ1075 differ by an Rf value of only 0.03. MDH clearly separates IPLB-HZ1075 from ATC-10 and also BTI-EAA from IPLB- SF-21AE which co-migrated when stained with LDH. Staining procedures are described infra.
Figure 12B:
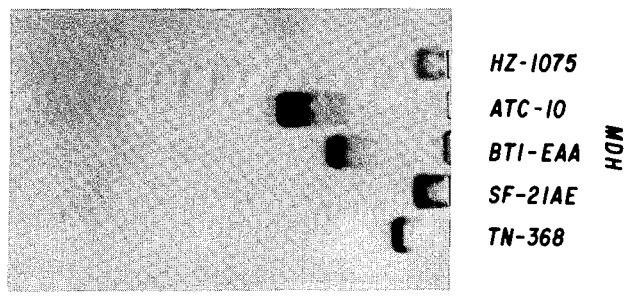

The IPLB-HZ1075 cell line consists of a heterogeneous population of cells, and this heterogeneity seems to account in part for the inability to obtain 100% infection upon inoculation with HzSNPV. To obtain a more homogeneous response to infection through cloning of individual cell strains, we subcloned and characterized twelve strains from IPLB-HZ1075 using dilution plating.

All of the subcloned cell lines were similar to the parental cell line in that none of them were capable of 100% infection upon inoculation with the HzSNPV isolate HzS-15 under our culture conditions. Each cell strain exhibited slightly different growth kinetics (see FIG. 8), predominant cell morphology, and ability to replicate virus (see Table VI infra).

While predominant cell morphologies were different for most of the cell lines, only two (UND-B and UND-G) exhibited a fairly homogeneous cell morphology. The others were composed of several different morphologies even though they originated from clonal populations. All of the cell strains were fibroblastic, similar to the parental cell line (Goodwin, R. H., et al., 1982, In Vitro 18:843–850).

Population doubling times for the cell strains varied widely between 37.33 and 65.48 hours, and the parental cell line had a doubling time near the maximum (63.15 hours). Routine subculturing of the parental cell line does not appear to select for cells with similar growth kinetics. Perhaps the mixed cell population regulates the growth of individual cell strains in some way, possibly by suppressing the growth of faster growing strains.

There was an equally wide variability in OB and ECV production upon infection, and no apparent correlation between any of the measured parameters. OB production could not be linked to either ECV titers or relative cell growth rates. If the results were influenced by the low multiplicity of infection, we might expect some correlation between OB or ECV production and cell growth rates. Analysis of the fast growing strains did not reveal any consistent pattern of either higher or lower OB or ECV production relative to the slower growing strains. In addition, we did not observe significant cell growth in any of the strains during the 10 day infection period. Consequently, we feel that the estimates do reflect the relative productivities of the cloned cell strains for either OBs or ECVs, but may not accurately reflect the overall relative susceptibility of the cell strains for HzSNPV.

Several of the subcloned populations seemed to replicate HzSNPV better than the parental IPLB-HZ1075 cell line with respect to both OB (UND-B,C,G,K,M,R) and ECV production (UND-B,C,F,G,K,L,M,O,R,V). This result differed from earlier studies with *Trichoplusia ni* cell line TN-368 (Faulkner, P., et al., 1976, In Invertebrate Tissue Culture Applications in Medicine, Biology, and Agriculture, Kurstak, E. and K. Maramorosch, eds., Academic Press, New York, pp.347–360; Volkman, L. E. and Summers, M. D., 1976, In Invertebrate Tissue Culture Applications in Medicine, Biology, and Agriculture, supra, pp. 289–296). Subcloned cell strains of TN-368 were distinguishable from the parental cell line with respect to cell doubling time (Faulkner, P., et al., supra) and ability to plaque *Autographa californica* MNPV (AcMNPV) (Volkman, L. E. and Summers, M. D., *supra*), but none of the TN-368 subcloned cell strains replicated AcMNPV better than the uncloned parental cell line.

Confirmation that all cell strains were derived from the IPLB-HZ1075 cell line came from comparisons of isozyme patterns (see FIG. 9). We also compared isozyme patterns of several invertebrate cell lines (see FIG. 10) and found that all could be separated unambiguously using the enzymes MDH and LDH in tandem. This is in contrast to earlier reports that were unable to separate IPLB-SF21AE and IPLB-HZ1075 using a large number of enzymes and two different gel systems (Brown, S. E. and Knudson, D. L., 1980, In Vitro 16:829-832; Tabachnik, W. J. and Knudson, D. L., 1980, In Vitro 16: 389-392).

In a specific embodiment, the IPLB-HZ1075 UND-K cell line may be preferred for use in the expression vector/host systems of the present invention because of its ability to grow Heliothis virus quickly and at high titers which plaque, thus enabling identification.

In a preferred embodiment, the growth medium of any IPLB-HZ1075 cell line used as a host in accordance with the invention should contain 1% bovine serum albumin and 2 g/liter L-glutamine in order to improve infectivity to about 100%. When using cultured cells as hosts in the expression/host systems of the present invention, it is preferred to infect the cell cultures with ECVs rather than OBs. The infectious cell culture supernatant can be stabilized by the addition of liquid agarose to a final concentration of 0.1%. Alternatively, virions can be isolated from the OBs according to procedures known in the art such as the technique described by Smith and Summers, 1978, Virology 84: 390-402, and the modified procedure described herein in Section 7.1.4. infra.

LARVA HOSTS

Baculoviruses expressing the recombinant polyhedrin genes of the present invention can be propagated and/or mass-produced by infection of various host insect larvae. The propagation and isolation of baculoviruses using laboratory larval populations has been previously described (e.g., Wood, H. A., et al., 1981, J. Inverter. Pathol. 38:236-241; Ignoffo, C. M. and Garcia, C., 1979, Environ. Entomol. 8:1102-1104). Larva hosts which may be used in the propagation and production of viruses expressing recombinant polyhedrin genes include but are not limited to those species listed in Table I, infra.

TABLE I

INSECT LARVA SPECIES WHICH CAN BE USED FOR THE PROPAGATION AND PRODUCTION OF VIRUSES EXPRESSING RECOMBINANT POLYHEDRIN GENES OF THE PRESENT INVENTION

*Heliothis zea* (Boddie)
*Trichoplusia ni* (Huber)
*Galleria mellonella*
*Spodoptera frugiperda*
*Estigmene area*
*Aedes aegypti*
*Choristoneura fumiferana*
*Heliothis virescens*
*Autographa californica*
*S. littoralis*
*Rachoplusia ou*
*Lymantria dispar*
*Bombyx mori*
*Orygia pseudotsugata*
*Pseudohazis eglanterina*
*N. sertifer*
*T. paludosa*
*P. brassicae*
*Orygia leucostigma*
*Choristoneura vindis*
*Plodia interpunctella*
*Choristoneura murinana*
*Cirphis unipuncta*
*L. pomonella*
*Cydia pomonella*
*Mamestra oleracea*
*Pseudaletia unipuncta*
*Pygera anastomosis*
*Zeiraphera diniana*

In particular embodiments, *T. ni* or *G. mellonella* larvae can be used for the propagation and production of recombinant AcMNPV, *G. mellonella* MNPV, or *T. ni* MNPV, while *H. zea* can be used to support the growth of recombinant HzSNPV.

Any rearing conditions and diet formulations can be used which support the growth and maintenance of the larvae. One example of a diet mix which can be used to support the growth of *T. ni* or *H. zea* larvae is described in Section 9.1. infra. Examples of rearing conditions which can be used for *H. zea*, *T. ni*, or *G. melonella* are described infra, in Sections 9.2.1., 9.2.2., and 9.3. It is possible that the larval strains are cannibalistic (e.g., *Heliothis zea*) and, therefore, cannot be grown all together. It would therefore be preferable to separate the larvae so that only one or two insects are dispensed into each container for growth.

It is preferable, but not required, to maintain the larval cultures in a germ-free environment. The cultures thus maintained would be free from the presence of exogenous microorganisms which can potentially produce substances toxic or allergenic for humans.

In a further preferred method of the invention, insect larvae can be cultured free of both exogenous and endogenous microorganisms. Since Lepidopterans (e.g., *Heliothis zea, Trichoplusia ni*) contain no endogenous symbiotic microorganisms, they can be maintained in the absence of both endogenous and exogenous microorganisms, thus eliminating the danger of contamination by microorganisms pathogenic for humans. In accomplishing and maintaining these germ-free conditions, the insect eggs can be sterilized (e.g. by treatment with peracetic acid; see Section 9.3., infra). The insect diet mix can be sterilized, e.g. by the use of radiation.

In addition, as discussed in Section 5.2., supra, a non-melanizing strain of virus is preferred for use, in order to optimize yield and purity of the recombinant polyhedrin obtained from the infected larvae.

In another embodiment of this aspect of the invention, it is possible to produce and use giant larvae for the propagation of the recombinant baculoviruses of the invention. Selective inhibition of juvenile hormone (JH) esterase has been shown to result in the maintenance of JH titers and in the production of giant larvae (Sparks, T. C., et al., 1983, Insect Biochem. 13:529; Hammock, B. D. and Roe, R. M., 1985, Meth. Enzymol. 111B:487). The use of such larvae in the mass production of the recombinant polyhedrins of the invention can greatly increase the obtained yields.

EXPRESSION IN OTHER MICROORGANISMS

The recombinant polyhedrin genes of the present invention can also be expressed in vector/host systems involving other microorganisms including but not limited to other viruses such as vaccinia viruses, adenoviruses, retroviruses, etc.; yeast; and bacteria.

As one embodiment, the production of recombinant polyhedrin crystals in bacterial cells has a number of attractive advantages. It would eliminate the need to transfer gene fusions into a baculovirus and to identify and characterize the resulting recombinant virus. In addition, it is cheaper and easier to grow large quantities of bacterial cells than to culture insect cells. Many different strains of bacteria and types of plasmids known in the art can be used in this embodiment of the present invention, as long as the host allows for appropriate expression of the recombinant polyhedrin gene of the vector.

Production in bacterial expression systems can be accomplished by use of the same type of genetic manipulations as described in Section 5.1.3., supra. For example, by taking advantage of the degeneracy of the genetic code, a polyhedrin gene segment can be synthesized which contains new and unique restriction sites, yet encodes the same amino acids as the wild-type polyhedrin gene. Thus, a "polyhedrin polylinker" sequence is created, a type of cassette vector, which can be ligated to the remainder of the parental polyhedrin gene, and which can be utilized to insert sequences encoding foreign epitopes at its unique restriction sites. Such a gene construction provides the potential to easily engineer a large number of changes into the polyhedrin gene. In addition, the gene construction can be designed with flanking restriction sites suitable for insertion into E. coli expression vectors. Insertion of the polyhedrin polylinker sequence into an E. coli expression vector will produce a cassette-expression vector which can greatly facilitate construction and expression, in bacteria, of a recombinant polyhedrin gene of the present invention. Such a construction is not restricted to use in E. coli; it can also be engineered for use in the baculovirus or other systems. One example of a polyhedrin polylinker is shown in FIG. 4. FIG. 4 shows a gene segment encoding the amino terminus to amino acid 58 (at the BamHI site) of the Autographa polyhedrin protein, which also contains new PvuI, ScaI, BclI, and XbaI sites at positions corresponding to amino acids 9, 19, 27, and 46, respectively. Ligation of a two kilobase pair BamHI fragment containing the 3' end of the AcMNPV polyhedrin gene will reconstruct the entire gene. The unique restriction sites can facilitate the replacement of small regions in the 5' section of the gene with synthetic oligonucleotides encoding new antigenic determinants. In particular, replacing the segment between the XbaI site and either the BamHI or BclI site enables the insertion of new determinants in a putatively modifiable region between amino acids 37-49. The SphI site can be used to add determinants to the amino terminus of the protein. The unique EcoRI site immediately 5' to the synthetic gene permits cloning the fusion gene into an EcoRI site of an E. coli expression vector. For example, in an embodiment involving the synthetic gene of FIG. 4, a vector which may be used is the E. coli expression vector PK223-3 (Pharmacia). This plasmid contains the tac promoter (de Boer, H. A., et al., 1983, Proc. Natl. Acad. Sci. U.S.A., 78:21) and Shine-Delgarno sequences upstream of unique cloning sites. In addition, there are strong ribosomal termination sequences downstream of the cloning sites. Thus, the PK223-3 plasmid construction would permit efficient regulated expression of genes inserted at its cloning site. Numerous other plasmids with suitable cloning sites and signals for expression may also be used.

The preceding discussion is intended only as an example of the types of manipulations and constructions which may be employed in the cloning and expression of recombinant polyhedrins. Other vectors, hosts, and synthetic gene sequences may be manipulated in similar fashions to express the recombinant polyhedrins of the present invention. Appropriate cassette vectors, transfer vectors, and/or cassette-expression vectors can be constructed and used to facilitate the appropriate recombinations.

Construction and expression in a suitable vector/host system will determine whether the recombinant polyhedrin expressed in such a system will crystallize. If the protein will not crystallize in vivo, the solubilized polyhedrin protein can be purified and crystallized in vitro (Shigematsu, H. and Suzuki, S., 1971, J. Invert. Pathol. 17:375-382). Thus by expressing the recombinant polyhedrin genes, polyhedrin crystals exposing new epitopes can be generated.

DETERMINATION OF THE IMMUNOPOTENCY OF FOREIGN EPITOPES EXPRESSED ON OR WITHIN RECOMBINANT OCCLUSION BODIES

Demonstration of immunopotency of the epitope of a pathogenic microorganism, carried on or within a recombinant occlusion body in accordance with the present invention, is a necessary step prior to vaccine formulation. Immunopotency of the foreign epitope expressed on or within recombinant occlusion bodies can be determined by monitoring the immune response of test animals following immunization with the recombinant OB. Occlusion bodies for immunization purposes can be obtained by purification from insects or insect cell cultures (for example, by the procedures of Section 7.1.4. infra, and Tweeten, K. A., et al., 1981, Microbiol. Rev. 45:379-408), or by in vitro recrystallization of polyhedrin (Shigematsu, H. and Suzuki, S., 1971, J. Invert. Pathol. 17:375-382). Test animals may include but are not limited to mice, rabbits, chimpanzees, and eventually human subjects. Methods of introduction of the immunogen may include oral, intradermal, intramuscular, intraperitoneal, intravenous, subcutaneous, intranasal, or any other standard route of immunization. The immune response of the test subjects can be analyzed by three approaches: (a) the reactivity of the resultant immune serum to the authentic pathogenic molecule or a fragment thereof containing the desired epitope, or to the isolated naturally occurring pathogenic microorganism, as assayed by known techniques, e.g. enzyme linked immunosorbant assay (ELISA), immunoblots, radioimmunoprecipitations, etc., (b) the ability of the immune serum to neutralize infectivity of the pathogen in vitro, and (c) protection from infection and/or attenuation of infectious symptoms in immunized animals.

In a specific embodiment of the invention, rabbits can be inoculated by a variety of protocols with recombinant AcMNPV OBs expressing amino acids 98-106 of the influenza A virus hemagglutinin. Rabbit antisera reacting to the recombinant OBs can be examined for cross-reactivity to the influenza hemagglutin monomer as well as to the homologous strain of influenza virus, by hemagglutin A inhibition and by antibody titer determination. In protection experiments, mice can be inoculated intraperitoneally with the recombinant OBs, subsequently challenged by intranasal inoculation of virulent virus, and monitored for the onset of disease symptoms.

USES OF RECOMBINANT OCCLUSION BODIES VACCINES

Recombinant OBs expressing epitopes of pathogenic microorganisms are particularly useful in the formulation of vaccines. In a preferred embodiment, the foreign epitope is exposed on the surface of the crystal. Since the crystalline lattice of the occlusion body is composed predominantly of the polyhedrin molecule, foreign epitopes within this molecule are presented a large number of times on the surface of the OB. Recombinant OBs can be used in vaccine formulations even if the foreign epitope is not presented on the surface of the crystal but is internal, since alterations in crystallization properties (e.g. dissociation in vivo) can allow slow release of protein (comprising the foreign epitope) from the crystal, allowing presentation of the epitope to the host's immune system. In addition, the occlusion bodies are produced in large quantity, are stable structures, and are easy to purify. They can be generated in insect cell cultures that do not produce known human pathogens. In a particular embodiment, recombinant OBs for vaccine use can be obtained from infected insect larvae grown in a germ-free environment.

The use of recombinant OBs may be especially advantageous when the heterologous peptide or protein to be used in a vaccine formulation is a hapten (i.e., a molecule that is antigenic but not immunogenic) which ordinarily must be coupled to a carrier molecule that confers immunogenicity. The production of recombinant OBs carrying the heterologous hapten on their surface using the expression vector/host systems of the present invention would render the molecule immunogenic and eliminate coupling reactions. Furthermore, the recombinant OBs can be dissociated and recrystallized so that (a) the enveloped recombinant virions can be removed from the solubilized recombinant OBs, which can then be recrystallized without the recombinant virus; and/or (b) a mixture of recombinant OBs, each of which bears a different heterologous protein, can be solubilized and recrystallized. The resulting OBs would bear each of the heterologous proteins and would be particularly useful as a multivalent vaccine. Alternatively, multivalent vaccines can be produced by engineering multiple epitopes into the polyhedrin gene so that multiple epitopes are expressed on each recombinant polyhedrin molecule which form the recombinant OBs.

In another specific embodiment of this aspect of the invention, the foreign peptide or protein to be expressed on or within a recombinant OB may be amphipathic, that is, having one face hydrophilic and one face hydrophobic. Such a foreign peptide may be especially useful in the induction of T cell-mediated immunity. An amphipathic epitope may provoke T cell stimulation by providing for the interaction of its hydrophobic face with the presenting cell membrane or Ia, and the interaction of its hydrophilic face with the T cell receptor (Allen, P. M., et al., 1984, Proc. Natl. Acad. Sci. U.S.A. 81:2489; Berzofsky, J. A., et al., 1985, in Immune Recognition of Protein Antigens, Laver, W. G. and G. M. Air, eds., Current Communications in Molecular Biology, Cold Spring Harbor Laboratory, New York, pp. 156–160). In a particular embodiment, a heterologous sequence encoding an amphipathic alpha-helical structure can be inserted into or replace portions of the polyhedrin gene which are nonessential for crystallization and which encode alphahelical regions, which may be hydrophobic.

Any protein epitope of a pathogenic microorganism which is capable of inducing an immune response specific to the microorganism can potentially be used in a recombinant OB vaccine formulation. Demonstration of the production of recombinant OBs which express the foreign epitope in an immunopotent state, as provided for by the present invention, is necessary prior to formulation as a vaccine.

Potentially useful antigens for recombinant OB vaccine formulations can be identified by various criteria, such as the antigen's involvement in neutralization of the pathogen's infectivity (Norrby, E., 1985, Summary, In Vaccines85, Lerner, R. A., R. M. Chanock, and F. Brown (eds.), Cold Spring Harbor Laboratory, New York, pp. 388–389), type or group specificity, recognition by patients, antisera, and/or the demonstration of protective effects of antisera generated to the antigen. In addition, the antigen's encoded epitope should preferably display a small or no degree of antigenic variation in time. The gene sequence encoding the epitope to be expressed on or within recombinant OBs may be obtained by techniques known in the art including but not limited to purification from genomic DNA of the microorganism, by cDNA synthesis from RNA of the microorganism, by recombinant DNA techniques, or by chemical synthesis.

Recombinant OBs have potential uses as vaccines for diseases and disorders of viral, parasitic, and bacterial origins. Many viral-specific antigens are known and can potentially be incorporated into the recombinant OB vaccine formulations of the invention. For example, such antigens, and/or portions thereof which encode the epitope(s), which may be used include but are not limited to influenza A hemagglutinin; Hepatitis A virus VP1; Hepatitis B surface, core, or e antigens; retroviral envelope glycoproteins or capsid proteins; poliovirus capsid protein VP1; rabies virus glycoprotein; foot and mouth disease virus VP1; Herpes simplex virus glycoprotein D; Epstein-Barr virus glycoprotein; pseudorabies virus glycoprotein; vesicular stomatitis virus glycoprotein, etc. In a particular embodiment, the recombinant OBs of the present invention can comprise an epitope of the AIDS virus (HTLV-III/LAV/HIV) glycoprotein and/or capsid proteins. Such an embodiment may be particularly useful in vaccinating against AIDS without concomitant induction of detrimental effects caused by the presence of the active AIDS virus glycoprotein such as the induction of T lymphocyte cell fusion and death.

Recent research has identified many potential antigens of bacteria or parasites which may be formulated in vaccines in accordance with the present invention. For example, such antigens, or fragments thereof which encode the epitope(s), which may be formulated in vaccines in accordance with the present invention include but are not limited to malaria antigens (Miller, L. H., 1985, In Vaccines85, Lerner, R. A., R. M. Chanock, and F. Brown (eds.), Cold Spring Harbor Laboratory, New York, pp. 1–5), cholera toxin, diptheria toxin, and gonococci antigens. As more specific examples, microbial genes which have been successfully cloned and may be used in recombinant OB vaccine formulations include but are not limited to, enterotoxin genes of *E. coli*, the toxin and filamentous hemagglutinin genes of *Bordetella pertussis*, and the circumsporozoite (CS) antigen of the malaria parasite *Plasmodium falciparum* (Norrby, E., 1985, In Vaccines85, supra, pp. 387-394; Dame, J. B., et al., 1985, In Vaccines85, supra, pp. 7-11).

USES OF ANTIBODIES GENERATED BY IMMUNIZATION WITH RECOMBINANT OCCLUSION BODIES

The antibodies generated against pathogenic microorganisms by immunization with the recombinant OBs of the present invention also have potential uses in diagnostic immunoassays, passive immunotherapy, and generation of antiidiotypic antibodies.

The generated antibodies may be isolated by standard techniques known in the art (e.g. immunoaffinity chromatography, centrifugation, precipitation, etc.), and used in diagnostic immunoassays to detect the presence of viruses, bacteria, or parasites of medical or veterinary importance in human or animal tissues, blood, serum, etc. The antibodies may also be used to monitor treatment and/or disease progression. Any immunoassay system known in the art may be used for this purpose including but not limited to competitive and noncompetitive assay systems using techniques such as radioimmunoassays, ELISA (enzyme linked immunosorbent assays), "sandwich" immunoassays, precipitin reactions, gel diffusion precipitin reactions, immunodiffusion assays, agglutination assays, complementfixation assays, immunoradiometric assays, fluorescent immunoassays, protein A immunoassays and immunoelectrophoresis assays, to name but a few.

The vaccine formulations of the present invention can also be used to produce antibodies for use in passive immunotherapy, in which short-term protection of a host is achieved by the administration of pre-formed antibody directed against a pathogenic microorganism. Passive immunization could be used on an emergency basis for immediate protection of unimmunized individuals who have been exposed to a pathogenic microorganism, for instance, in hospitals and other health-care facilities. Human immunoglobulin is preferred for use in humans since a heterologous immunoglobulin will induce an immune response directed against its foreign immunogenic components.

The antibodies generated by the vaccine formulations of the present invention can also be used in the production of antiidiotypic antibody. The antiidiotypic antibody can then in turn be used for immunization, in order to produce a subpopulation of antibodies that bind the initial antigen of the pathogenic microorganism (Jerne, N. K., 1974, Ann. Immunol. (Paris) 125c:373; Jerne, N. K., et al., 1982, EMBO 1:234).

BIOLOGICAL INSECTICIDES

Baculoviruses are major pathogens of a large number of agricultural pests (Vlak, J. M. and Rohrmann, G. F., supra; Tweeten, K. A., et al., 1981, Microbiol. Rev. 45:379-408). For example, one baculovirus host, the corn earworm *Heliothis zea,* in many areas routinely damages 90-100% of the ears of sweet corn (Kirk-Othmer, Encyclopedia of Chemical Technology, 1981, 3rd Ed., Vol. 13, John Wiley & Sons, New York, p. 415). HzSNPV has been approved as a viral insecticide and is used as a pathogen for the cotton bollworm and the corn earworm. The OB is the infectious particle responsible for transmission of the virus from organism to organism in the wild. The production of recombinant occlusion bodies in accordance with the present invention thus provides for horizontal transmission of infection with concomitant expression of the foreign gene. Manipulation of the polyhedrin protein to incorporate enzymatic activities, toxic peptides, or any molecule with insecticidal activity can increase the lethality of the OB to host agricultural pests. Thus, the recombinant OBs of the present invention have valuable applications as biological insecticides.

Genes which may be recombined into OBs in accordance with this embodiment of the invention include any genes which encode molecules that effectively increase the desired insecticidal activity of the baculovirus without impairing the viability or infectivity of the virus itself. Such molecules include but are not limited to those which encode enzymes, enzyme inhibitors, insect hormone antagonists, neurotoxins, metabolic inhibitors, insect chemattractants, endotoxins of other insect pathogens, etc. For example, molecules which interfere with physiological and/or developmental processes unique to arthropods that are susceptible to baculoviral infection, may be expressed on or within recombinant OBs. Such molecules include but are not limited to insect growth regulators such as hormone antagonists (e.g. neotenin antagonists), and chitin synthesis inhibitors. Neuropeptides which are toxic or which induce detrimental behavioral modifications (e.g. loss of appetite or mating behavior) may be encoded within the polyhedrin gene. Sex pheromones which act as chemattractants may be used to increase spread of the baculovirus infection throughout the insect population. A chitinase incorporated into the OB may increase the infectivity of the virus. An endotoxin of another insect pathogen, such as the *Bacillus thuringiensis* endotoxin, may be expressed in order to increase pathogenicity. Many specific embodiments of the invention are possible, provided that the recombinant form of the insecticidal molecule is functionally active within the physiological environment of the infected insect. Metabolic precursors to insecticidal molecules may also be encoded by the recombinant polyhedrin gene, provided that the metabolic machinery to convert the peptide to a biologically active form is available and functional at the site of infection within the host insect.

Any standard method can be used to assay lethality of the recombinant baculovirus. Such methods include but are not limited to the diet-surface technique and container, to bioassay OB activity (Ignoffo, C. M., 1966, J. Invert. Pathol. 8:531-536; Ignoffo, C. M. and Boening, O. P., 1970, J. Econ. Entomol. 63:1696-1697).

EXPRESSION VECTORS

The recombinant viruses which form occlusion bodies expressing heterologous peptides, the production of which is provided for by the present invention, can be used generally as expression vector systems for the production of the foreign peptide(s) which they encode. In this embodiment of the invention, the recombinant baculoviruses which express the foreign peptide under control of the polyhedrin promoter are used to infect an appropriate host cell in order to obtain the desired quantities of the heterologous peptide. To this end, the foreign peptide (which is a fusion polyhedrin protein) may be purified from the occluded virions, isolated occlusion bodies, cell culture media, infected larvae, etc., by standard techniques known in the art for the purification of proteins, including but not limited to chromatography (e.g. ion exchange, affinity, and sizing column chromatography), centrifugation, differential solubility, isoelectric focusing, and preparative electrophoresis.

Expression as part of a (polyhedrin) crystal can greatly facilitate isolation of the heterologous peptide or protein in substantially pure form. In addition, standard procedures such as solubilization of the crystal, followed by immunoaffinity chromatography, and, if desired, recrystallization (as described in Section 5.1.5., supra) can be used to increase purity of the final product.

IMMUNOASSAYS

The recombinant OBs of the present invention, expressing foreign epitope(s), may be used as antigens in immunoassays for the detection of antibodies to the epitope(s). The recombinant OBs may also be used to detect the same or related epitope(s) by competition assays. The recombinant OBs, or the foreign epitope(s) expressed by them, may be used in any immunoassay system known in the art including but not limited to competitive and noncompetitive assay systems using techniques such as radioimmunoassays, ELISA (enzyme-linked immunosorbent assay), "sandwich" immunoassays, precipitin reactions, gel diffusion precipitin reactions, immunodiffusion assays, agglutination assays, complement-fixation assays, immunoradiometric assays, fluorescent immunoassays, protein A immunoassays. and immunoelectrophoresis assays, to name but a few.

As demonstrated in the Examples detailed herein, the recombinant OBs of the invention are capable of capturing and precipitating antibodies specific for the foreign epitope(s) presented on the recombinant OBs. This is an attractive feature of the recombinant OBs which makes them particularly useful for the detection of antibodies in sample fluids, especially where the antibodies are presented at low concentrations. For example, the recombinant OBs bound to their captured antibodies could be immobilized by antipolyhedrin antibodies. The presence of the captured antibody can be detected using appropriate anti-immunoglobulin antibodies. Thus, a "sandwich" type of immunoassay for detecting different antibodies in sample fluids can be accomplished using "universal" capture (e.g., antipolyhedrin) and detection antibodies (e.g., anti-human Ig).

Alternatively, recombinant OBs which present the Fc binding region of protein G or A could be produced by cloning appropriate regions of those genes into the polyhedrin gene within the modifiable domains described herein. These recombinant OBs can be used to bind any antibody. The resulting recombinant OB/antibody complexes can then be used in immunoassays to bind and capture antigens in sample fluids. These could similarly be used in the "sandwich" type of assay system described above to detect antigens in sample fluids.

IMMOBILIZED ENZYMES

The recombinant OBs of the present invention which express the active site of an enzyme on their surface can be used in a variety of procedures which require immobilized enzymes. For example, the recombinant enzymatic OBs may be packed into a column on which reactions catalyzed by the enzyme can be carried out. The resulting products can easily be separated from the mixture of reactants and enzyme.

EXAMPLE: CONSTRUCTION OF TRANSFER VECTORS USED FOR INTRODUCING FOREIGN GENE SEQUENCES INTO THE HELIOTHIS POLYHEDRIN GENE TO PRODUCE Hz RECOMBINANTS

The subsections below describe the sequencing of the Heliothis polyhedrin gene and the construction of a family of plasmid transfer vectors which allow for the production of *Heliothis zea* virus recombinants which contain foreign genes within the polyhedrin gene sequence.

MATERIALS AND METHODS

RESTRICTION MAPPING

Plasmid DNAs were digested with restriction endonucleases HindIII, EcoRI, PstI, XbaI, BamHI, SalII XhoI, NruI, ClaI, HincII, BclI, or KpnI under conditions specified by the manufacturer (Bethesda Research Laboratories or Promega Biotec). Digested DNAs were size fractionated on 0.7% to 1.2% agarose or 8% acrylamide gels containing 90 mM Tris-borate, 90 mM boric acid, 2 mM EDTA (pH 8.0), and 0.1 ug/ml of ethidium bromide. DNA bands were visualized with an ultraviolet transilluminator and photographed. Analyses of single and multiple digestions were used to construct the restriction maps.

SOUTHERN BLOTTING

Gels were soaked in denaturing solution (0.5M NaOH, 1.5M NaCl) for 30 minutes. The gels were neutralized by soaking in 1.0M Tris-HCl pH 8.0, 1.5M NaCl. DNA was transferred to nitrocellulose by a modification of the method of Southern (J. Mol. Biol. 98:503-517). DNA was blotted using 1.0M NH$_4$acetate. Filters were baked under vacuum for two hours and soaked in prehybridization solution (0.12M NaPO$_4$ pH 6.8, 2×SSC, 50% formamide, 10 mM EDTA, 1% sarcosyl and 3×Denhardts) for more than three hours. Filters were rinsed with distilled water and incubated at 37° C. overnight with fresh prehybridization solution plus denatured labelled radioactive probes. Filters were rinsed in 0.2×SSC and washed for one hour in prehybridization solution without Denhardts. Rinses and washes were repeated four times. Filters were dried and autoradiographed with Kodak X-Omat AR5 film.
SSC=150 mM NaCl, 15 mM sodium citrate pH 7.0
Denhardt's Solution=0.02% ficoll, 0.02% polyvinylpyrrolidone, 0.02% BSA

DNA SEQUENCING

DNA sequences were determined using the dideoxy chain termination method with M13 subclones (Sanger, F., Nicklen, S., and Coulson, A. R., 1977, Proc. Natl. Acad. Sci. U.S.A. 74:5463-5467; Messing, J., Crea, R., and Seeburg, P. H., 1981, Nucl. Acid Res. 9:309-321) of the Heliothis polyhedrin gene. Supernatants of M13 infected cells were centrifuged two times at 5000 rpm for 20 minutes to remove cells and cell debris. Phage were precipitated by adding 1/5 volume 20% PEG6000, 2.5M NaCl. Pellets were resuspended in 6, 6, .2 (6 mM Tris-HCl pH 8.0, 6 mM NaCl 0.2 mM EDTA) and virus reprecipitated with 1/5 volume 20% PEG, 2.5M NaCl. Care was taken to remove as much liquid from the pellet as possible. Pellets were resuspended in 6, 6, .2 and DNA was extracted with phenol saturated with 0.1M Tris pH 8.0. DNA was reextracted with phenol:chloroform (1:1), then with chloroform, and finally with ether. DNA was precipitated with ethanol twice and rinsed one time.

Single stranded DNA templates were annealed to sequencing primers (Bethesda Research Laboratories or Pharmacia) in 10 μl reactions containing 5 μl of single stranded template, 2 μl of primer, 2 μl of HB buffer (70 mM Tris pH 7.5, 70 mM $MgCl_2$, 500 mM NaCl). Reactions were heated to 95° C. for 5 minutes and allowed to cool to room temperature for 45 minutes. After annealing, 2 μl of alpha32P-dATP, 1 μl of 25 μM dATP and 2 Units of DNA Polymerase Large Fragment (Bethesda Research Laboratories, Pharmacia, or Promega Biotec) were added. Primer extensions in the presence of the dideoxy nucleotides were initiated by adding 3 μl of the annealing mix to tubes containing the appropriate mix of dideoxy (dd) and deoxy nucleotides. A reaction: 1 μl of 0.5 mM ddATP and 1 μl 125 μM dCTP, dGTP and dTTP. G reaction: 1 μl of 0.625 mM ddGTP and 1 μl 8 μM dGTP, 170 μM dCTP and 170 μM dTTP. C reaction: 1 μl 0.5 mM ddCTP and 1 ul 8 μM dCTP, 170 μM dGTP and 170 μM dTTP. T reaction: 1 μl 0.84 mM ddTTP and 1 μl of 8 μM dTTP, 170 μM dCTP and 170 μM dGTP. Reactions were incubated at 45° C. for 15 minutes. 1 μl of 0.5 mM dATP, 0.5 mM dGTP, 0.5 mM dCTP and 0.5 mM dTTP were added and the reactions were incubated for an additional 15 minutes. The reactions were stopped by adding 12 μl of 95% formamide and 10 mM EDTA pH 8.0. The samples were heated to 95° C. and loaded on denaturing acrylamide gels containing 8 M urea, 90 mM Tris pH 8.3, 90 mM boric acid and 2 mM EDTA. Gels were fixed in 10% acetic acid, 10% methanol, dried and autoradiographed.

Alternatively, DNA was sequenced as described by Chen, E., and Seeburg, P., 1985, DNA 4:165-170 using the Sequenase TM system (U.S. Biochemicals, OH)

IDENTIFICATION AND SEQUENCING OF THE POLYHEDRIN GENE OF HELIOTHIS ZEA VIRUS

Heliothis zea* DNA was obtained from virus isolated from *Heliothis zea* infected larvae. Viral HindIII and XhoI fragments were cloned into the HindIII and SalI site, respectively, of pUC12. Two plasmids were characterized: pHH5 which contains a 3.1 kb HindIII virus fragment and pHX12 which contains a 6.5 kb XhoI virus fragment. Both inserts cross-hybridized to a DNA fragment encoding part of the Autographa polyhedrin gene.

Restriction maps of pHH5 and pHX12 demonstrated that the pHH5 insert is contained within pHX12. Southern blots of pHH5 using the Autographa polyhedrin gene as a probe indicated that a 1.7 kb NruI fragment cross-hybridized to the Autographa polyhedrin gene. HincII and HindIII/SalI fragments of pHH5 and the HindIII/EcoRI fragments of pHX12 were subcloned into M13mp18 (Yanisch-Perron, C., et al., 1985, Gene 33:103-119). The EcoRI/NruI fragment of pHE2.6 (described infra in Section 6.3.2.) and the EcoRI/HindIII fragment of transfer vector 1 (described infra in Section 6.3.4. were also subcloned. The DNA sequence of selected subclones was determined using the dideoxy chain termination method (Sanger, F., et al., 1977, Proc. Natl. Acad. Sci. U.S.A. 74:5463-5467). The sequencing strategy used is diagrammed in FIG. 1B. The sequence of the Heliothis polyhedrin gene is shown in FIG. 1. A restriction enzyme map for the restriction endonucleases HindIII, NruI, HincII, and AccI was derived from the nucleotide sequence and is shown in FIG. 1A. The digest fragments and sizes are shown in Table II.

TABLE II

HindIII/ NruI/HincII/AccI RESTRICTION ENZYME DIGESTION FRAGMENTS OF THE HELIOTHIS POLHEDRIN GENE[1]

List of Fragments from 5' to 3' End

| Fragment # | Fragment size | Starts at | Ends at |
|---|---|---|---|
| 1 | — | —* | +2 |
| 2 | 250 | +3 | +252 |
| 3 | 9 | +253 | +261 |
| 4 | 14 | +262 | +275 |
| 5 | 12 | +276 | +287 |
| 6 | — | +288 | —* |

[1]Fragments shown are those expected from the DNA sequence of the Heliothis polyhedrin gene shown in FIG. 1, after digestion with HindIII, NruI, HincII, and AccI.

*Not within the sequenced region.

The DNA sequence of the subclones was compared with that of the Autographa polyhedrin gene in order to identify the coding sequence of the Heliothis polyhedrin gene. The DNA sequence shown in FIG. 1 reveals an open reading frame of nucleotides. The 7th codon of the open reading frame encodes a methionine which is followed by a sequence encoding amino acids which have 84% amino acid sequence homology to the Autographa polyhedrin sequence. This sequence terminates with a TAA codon as found in the corresponding position of the Autographa gene. We defined the first methionine in this open reading frame as the initiating codon of the Heliothis polyhedrin gene.

If the Autographa (MNPV) and Heliothis (SNPV) polyhedrin amino acid sequences are aligned to maximize sequence homology, there is 84% sequence homology between the two proteins. This compares with 77% sequence homology between Heliothis (SNPV) and Bombyx mori (MNPV) proteins (FIG. 2). The Autographa and Bombyx proteins also share 84% sequence homology. If the tyr-ser-tyr sequence at amino acid residues 5-7 of the Heliothis sequence mark the beginning of the homology between the two proteins, the Heliothis sequence contains an insertion of an additional amino acid residue at the amino terminus as compared with the Autographa and Bombyx proteins There are 36 amino acid substitutions between the Autographa and Heliothis proteins as well as a deletion of an amino acid between positions 226 and 227 of the Heliothis sequence.

The Heliothis and Bombyx sequences are somewhat more divergent, sharing only 77% sequence homology. In addition to the 52 amino acid substitutions, there are two single amino acid insertions as well as two deletions in the Heliothis sequence. Interestingly, of the four deletions and insertions between these two sequences, one insertion and one deletion are found in the Heliothis-Autographa comparison and the other insertion and deletion are found in the Autographa-Bombyx comparison. This suggests that the evolutionary divergence between Autographa and either Heliothis or Bombyx is approximately the same and that Heliothis and Bombyx are more highly divergent. Similar conclusions can be reached by comparing the overall sequence homology of the polyhedrin proteins of the three species. There does not appear to be a relationship between the degree of sequence divergence and whether the virus is an SNPV or MNPV. The degree of sequence divergence between Autographa (MNPV) and either the Heliothis (SNPV) or Bombyx (MNPV) is similar.

The pattern of hydrophilicity is very similar for the Autographa and Heliothis proteins (FIG. 3). Interestingly, the region of highest hydrophilicity of the polyhedrin proteins is the region of greatest sequence divergence. There is only 54% sequence homology between the Autographa and Heliothis polyhedrins in the region between amino acids 38 and 50 of the sequence. The Autographa and Bombyx sequences share only 31% sequence homology, while the Heliothis and Bombyx sequences are 39% homologous in this region. These values compare with approximately 80% sequence homology for the entire protein. Conceivably, these hydrophilic regions identify a site involved in some species specific interaction with other viral or cellular components. Small peptides generated from this region perhaps may be used to raise monoclonal antibodies that could discriminate among different baculoviruses.

CONSTRUCTION OF TRANSFER VECTORS

The plasmids pHH5 and pHX12 were used to construct a transfer vector, termed pHE2.6, which allows for the insertion of foreign genes within the polyhedrin gene sequence so that recombinant Hz viruses containing the foreign genes can be produced via in vivo recombination.

Figure 5B:
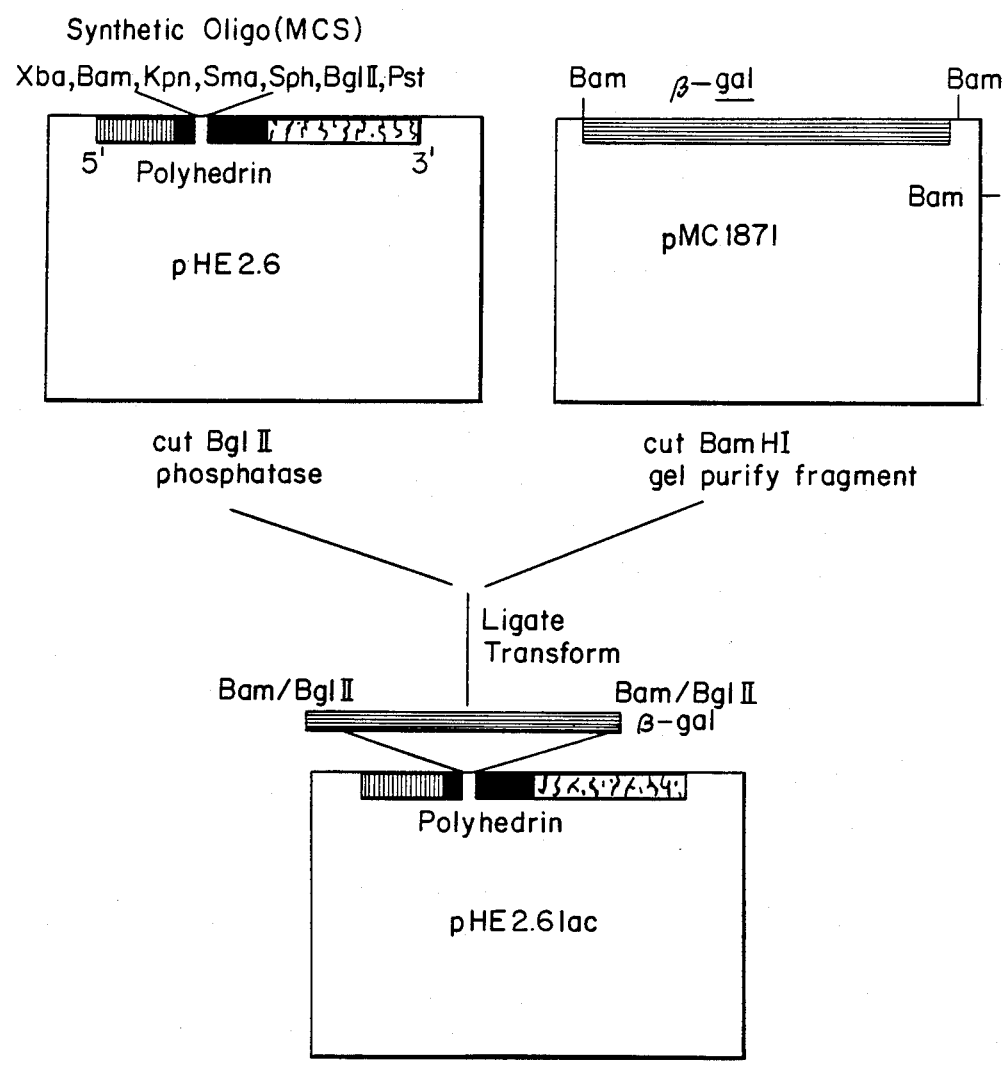
FIG. 5A. The construction of transfer vector PHE2.6, which can be used to insert foreign genes within the polyhedrin gene and to produce Hz viruses via in vivo recombination. These Hz recombinants, when placed in an appropriate host system, will express the foreign gene under the control of the Heliothis polyhedrin promoter. The following abbreviations are used in the figure: polyH (Heliothis polyhedrin gene sequence), RI (EcoRI), Sst (SstI), Sma (SmaI), Bm (BamHI) Xb (XbaI), Sal (SalI), Pst (PstI), H3 (HindIII), Nr (NruI), and Xho (XhoI).

The construction of this transfer vector is outlined in FIG. 5A, which should be referred to in order to simplify the description that follows.

PARENT PLASMIDS: pHH5 AND pHX12

The preparation of pHH5 and pHX12 is described above in Section 6.2. The pHH5 plasmid contains a 3.1 kb HindIII fragment of the Hz virus DNA (starting from nucleotide residue number 281 of the polyhedrin gene sequence depicted in FIG. 1) in the HindIII site of pUC12 (Vieira, J. and Messing, J., 1982, Gene 19:259) (FIG. 5A). The HindIII Hz DNA insert of pHH5 encodes approximately two-thirds of the polyhedrin gene comprising the carboxy-coding region (i.e., approximately one-third of the polyhedrin coding sequence comprising the amino-coding region is missing). The polyhedrin gene sequence is oriented so that the polylinker of the pUC12 parent plasmid is located upstream or 5′ to the polyhedrin gene sequence (FIG. 5A).

The XhoI Hz DNA insert of the pHX12 plasmid contains the entire polyhedrin gene sequence inserted into the SalI site of pUC12. The Hz polyhedrin gene sequence in pHX12 is oriented in the opposite direction with respect to the pUC12 polylinker as compared with the Hz polyhedrin coding sequence contained in pHH5; that is, the EcoRI site of the polylinker of pUC12 is located 3′ to the polyhedrin gene sequence in pHX12 (FIG. 5A).

CONSTRUCTION OF TRANSFER VECTORS

A restriction fragment of pHX12, containing portions of the amino-coding terminus of the Hz polyhedrin gene sequence, was used to reconstruct the polyhedrin gene in pHH5 so that a transfer vector containing the polyhedrin gene sequence interrupted at its amino-coding terminus by a multiple cloning site (MCS), would be produced.

The pHX12 plasmid was cleaved with EcoRI and NruI, and an approximately 1125 bp EcoRI-NruI fragment, containing the promoter and amino-terminal portion of the Heliothis polyhedrin gene, was isolated. This 1125 bp fragment was cloned into the EcoRI and SmaI sites of the pUC12 polylinker in pHH5. The BamHI to PstI sequence of the polylinker of this clone was then replaced with a synthetic oligonucleotide containing various restriction endonuclease recognition sites (a multiple cloning site, MCS). The sequences at the cloning junctions of the oligonucleotide have been confirmed by DNA sequence analysis.

The resulting plasmid, termed pHE2.6, contains the polyhedrin 5′ flanking region including promoter sequences, 5′ polyhedrin coding sequences, an MCS, 3′ polyhedrin coding sequences, 3′ polyhedrin flanking region, and pUC12 sequences. Foreign gene sequences can be inserted into the polylinker and the resulting plasmid vector can be used to transfect host cells infected with *Heliothis zea* virus. Hz virus recombinants will be formed which contain the foreign gene and direct its expression using the polyhedrin promoter.

TRANSFER VECTORS EXPRESSING BETA-GALACTOSIDASE

A transfer vector, termed pHE2.61ac, was constructed to contain the *E. coli* beta-galactosidase (B-gal) gene inserted within an MCS flanked by Heliothis polyhedrin sequences (FIG. 5B). A 3 kb fragment of plasmid pMC1871 (Pharmacia), containing the *E. coli* B-gal gene, was isolated by cleavage with BamHI followed by gel purification. Plasmid pHE2.6 was cleaved with BglII, treated with bacterial alkaline phosphatase, and ligated (T4 DNA ligase) to the pMC1871-derived fragment in order to insert the B-gal gene into the BglII site of pHE2.6. The resulting plasmids contained the B-gal gene in both orientations (5′ to 3′, and 3′ to 5′) with respect to the polyhedrin promoter and coding sequences. *E. coli* strain DH1 was transformed with the resulting plasmids, and the identity of transformants was confirmed by DNA fragment size determinations upon restriction digestion of their plasmid DNA. *E. coli* strain DH5 alpha (Bethesda Research Laboratories) was also transformed with the B-gal-containing plasmids, and the resulting transformants were tested according to the "bluewhite" screening technique of Messing et al. (1977, Proc. Natl. Acad. Sci. U.S.A. 74:3642–3646). Briefly, the transformed bacterial cells were mixed with the chromogenic substrate "X-gal" (5-bromo-4-chloro-3-indolyl-B-D-galactopyranoside) before plating. Blue bacterial colonies arise from bacteria containing plasmids that express functional B-gal activity. Such plasmids contain a beta-galactosidase gene which encodes the enzyme responsible for hydrolysis of "X-gal" and resultant production of a blue 5-bromo-4-chloro-indigo. Bacteria harboring plasmids that do not express functional B-gal activity give rise to white colonies since there is no ability to hydrolyze the chromogenic substrate.

The plasmid construction which contained B-gal in the appropriate orientation produced blue colonies indicative of beta-galactosidase activity. This plasmid was termed pHE2.61ac. pHE2.61ac was determined by appropriate restriction digestions to contain the B-gal gene in the proper orientation (i.e. the same 5′ to 3′ direction) to the polyhedrin promoter. Those transformants containing the parental plasmid pHE2.6 or the B-gal gene in the wrong orientation produced only white colonies.

Plasmid pHE2.61ac has been used for transfections into Heliothis virus-infected cells in order to transfer the B-gal gene fusion into Heliothis virus. Once a Heliothis virus expressing beta-galactosidase is obtained, the virus can be used as the parental virus for further manipulations involving insertions and deletions of the polyhedrin gene, through transfection of parental virus-infected cells with transfer vectors such as plasmid pHE2.6. Selection of the appropriate recombinant viruses would be greatly facilitated by detection of white plaques amidst a background of blue plaques.

GENERATION OF DELETIONS OF HELIOTHIS POLYHEDRIN AMINO-TERMINAL SEQUENCES

Figure 5C:
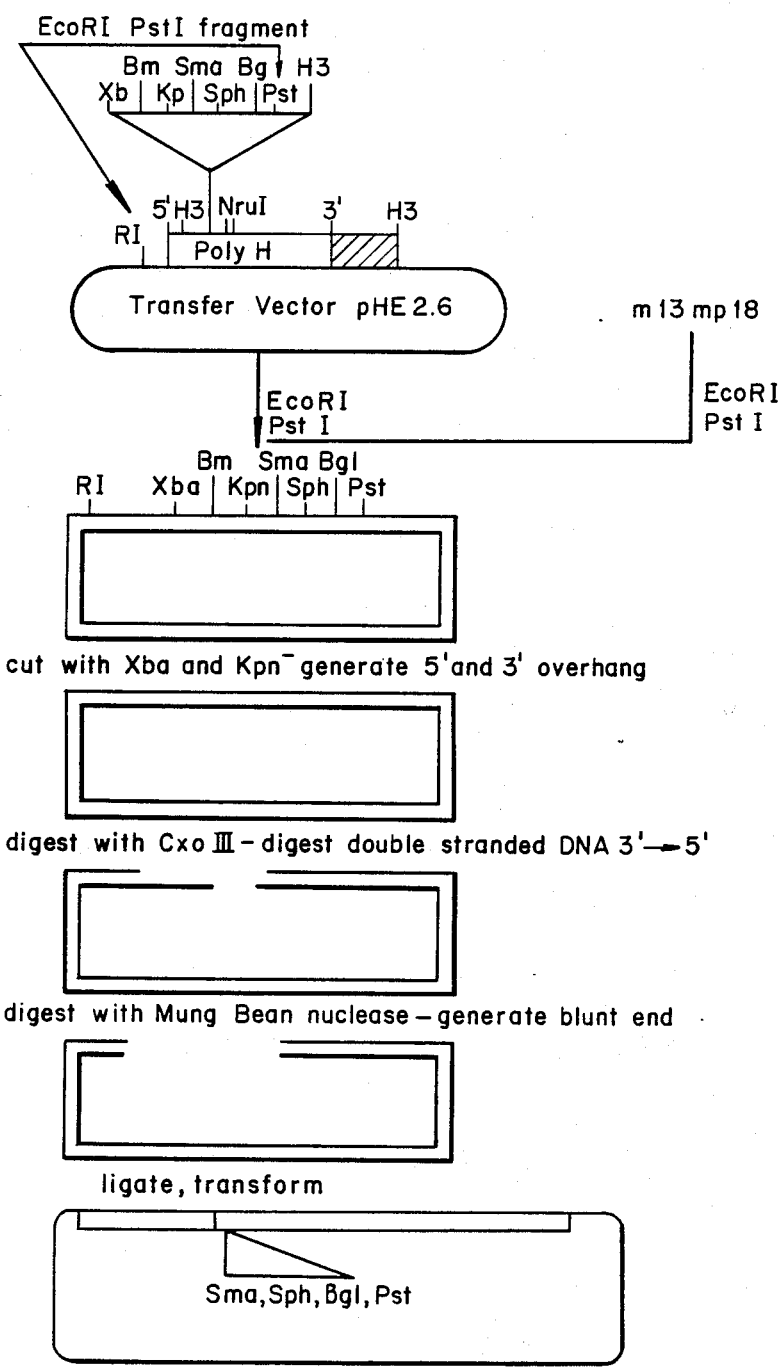

The strategy we have used to create deletions in the amino-terminus of the polyhedrin gene in Heliothis transfer vectors is diagrammed in FIG. 5C.

Plasmid pHE2.6 was digested with EcoRI and PstI. A 1.1 kb EcoRI-PstI fragment containing the Heliothis polyhedrin gene was generated, which was subcloned into M13mp18. The double-stranded replicative form of the resulting M13 derivative was digested with XbaI and KpnI, which cut within the MCS, to generate a single-stranded 5' overhang at the XbaI cleavage site and a single-sranded 3' overhang at the KpnI cleavage site. The resulting DNA was treated with Exonuclease III (exo III) which digested a single strand of the double-stranded DNA for a variable length in the 3' to 5' direction starting from the XbaI-cleaved end. The KpnI-cleaved end which has a 3' overhang is resistant to exo III digestion. The DNA was then digested with Mung Bean nuclease, which digests singlestranded DNA, to generate blunt ends by removing the single-stranded DNA left after exo III digestion. The blunt ends were ligated together with DNA ligase, resulting in transfer vectors that contain deletions of various length within the N-terminal portions of the Heliothis polyhedrin gene. The transfer vectors thus derived contain the Heliothis polyhedrin promoter, 5' polyhedrin regions of various length, an abbreviated MCS, and 3' polyhedrin sequences.

Thus far, several N-terminal deletion transfer vectors have been obtained in this fashion. Transfer vector 1 has a 282 base pair (bp) deletion spanning nucleotide number 63 of FIG. 1 through the KpnI site. Transfer vector 2 has a 274 bp deletion spanning nucleotide number 71 of FIG. 1 through the KpnI site. Additional deletion mutations are being generated. Similar manipulations can be done at other suitable restriction sites in order to obtain deletions of regions that are nonessential for OB formation.

EXAMPLE: HELIOTHIS VIRUSES FOR USE IN GENERATION OF RECOMBINANT OCCLUSION BODIES

Twenty plaque-purified strains of HzSNPV Elcar) were characterized based on their restriction endonuclease digestion patterns of viral DNA and structural protein profiles. Each of the twenty strains had a unique genotype which was distinguishable by digestion with restriction endonucleases BamHI, EcoRI, HindIII, or PstI. Most of the genomic heterogeneity between strains was located between map units 23.5 and 43.3. Differences were evident in the occluded virus structural protein profiles of all the plaque-purified strains relative to the wild-type isolate. We noted differences in pathology of the plaque-purified strains upon inoculation of *H. zea* larvae, and were able to segregate the strains into three categories based upon the relative rates of death (as measured by immobility) and of melanization (as measured by darkened appearance and disruption of cuticle) from the time of inoculation. The genotype of the weakly melanizing strain, HzS-15, was extensively characterized relative to the wild population genotype, using numerous restriction enzymes. A genomic map was constructed for HzS-15 using the enzymes BamHI, PstI, and SstI.

MATERIAL AND METHODS

IN VITRO PROPAGATION OF HzSNPV

Infectious extracellular virus (ECV) was obtained from larvae five days post infection and before melanization. Hemolymph was collected by clipping a proleg and bleeding 10 larvae into 5 ml of TNM-FH medium (Hink, W. F., 1970, Nature 266:466–467) containing $5 \times 10^{-3}$M 1-cysteine-HCl and $5 \times 10^{-3}$M dithiothreitol. The diluted hemolymph was filter-sterilized and used as inoculum for IPLB-HZ1075 cells (Goodwin, R. H., et al., 1982, In Vitro 18:843–850) adapted for growth in TNM-FH medium. Inoculation of cell cultures was accomplished by adding 5 ml of filtered inoculum to a 24 hour old monolayer of $1.0 \times 10^6$ IPLB-HZ1075 cells in a tissue culture flask (25 cm$^2$). After one hour at 29° C., the inoculum was removed and the monolayer washed once with fresh media. Five ml of TNM-FH was added and the cultures were incubated at 29° C. and monitored at 24 hour intervals for the presence of occlusion bodies.

PLAQUE PURIFICATION OF HzSNPV ISOLATES

Plaque assays were performed on supernatants of cell cultures infected with the larval-isolated HzSNPV as previously described (Fraser, 1982, J. Tis. Cult. Meth. 7:43–46). Twenty-four wild-type (MP type) plaques were picked and used as inoculum for $1 \times 10^5$ cells in each well of a 24 well plate. These once-plaque-purified isolates were re-assayed and individual plaques from the second assay were amplified first in 24-well plate cultures, and then in 25 cm$^2$ flask cultures of IPLB-HZ1075 cells.

LARVAL PROPAGATION OF VIRUS

Individual strains were amplified by oral inoculation of one to two inch long *Heliothis zea* larvae (third to fourth instar) with occlusion bodies isolated from the second cell culture passage of each plaque-purified strain. Infections were allowed to progress for 4 to 7 days before collecting the larvae. Larvae infected with each isolate were separated into either melanized or non-melanized pools upon collection, and both pools were frozen at $-20°$ C. until use.

ISOLATION OF VIRIONS FROM OCCLUSION BODIES

Infectious occlusion bodies (OBs) were harvested from pools of infected, non-melanized larvae by homogenization in TE buffer (10 mM Tris-HCl, 1 mM EDTA, pH 7.6) containing 0.1% SDS. The larval homogenate was filtered through two layers of cheesecloth and centrifuged at $1,800 \times g$ for 15 minutes. The supernatants were discarded and the OB pellet washed twice by resuspension in 20 ml of TE buffer and centrifugation at $1,800 \times g$. The washed OBs were resuspended in a final volume of 10 ml TE buffer.

Virions were isolated from the washed, partially purified OBs according to the procedure of Smith and Summers (1978, Virology 84:390–402) with slight modifications. Five ml of dissolution buffer (0.3M Na₂CO3, 0.03M EDTA, 0.51M NaCl, pH 10.9) was added to 10 ml of washed OBs (approximately 15 mg/ml), and the OBs were dissolved by incubation for 10 minutes at room temperature. The mixture was layered on 20-60% (w/w) sucrose gradients (in TE buffer) and centrifuged at 75,000× g for 60 minutes at 4° C. The single visible virion band was collected, diluted with an equal volume of TE buffer, and the virions pelleted at 55,000× g for 30 minutes (4° C.). The pelleted virions were resuspended in distilled water and stored at −20° C. until use.

ISOLATION OF VIRAL DNA

Gradient-purified virions were incubated in TE buffer containing 0.1% KCl, 0.1% SDS, and 0.1 mg/ml proteinase K (Sigma) for 3 hours at 65° C. Following two extractions with phenol and two extractions with chloroform:isoamyl alcohol (24:1), the DNA was precipitated by the addition of 1/10 volume of 2M sodium acetate, and 2 volumes of 95% ethanol. The precipitated DNA was pelleted at 1,800× g for 15 minutes and resuspended in sterile distilled water by heating at 65° C. for 30 minutes. The concentration of DNA was determined by absorbance at 260 nm, and the DNA was stored at 4° C. until use.

RESTRICTION ENDONUCLEASE DIGESTIONS

Viral DNAs were digested with BamHI, EcoRI, EcoRV, HindIII, KpnI, PstI, and SstI restriction endonucleases (Bethesda Research Laboratories) under conditions specified by the supplier. Restriction enzyme fragments were separated by electrophoresis in 0.75% agarose gels (20×20 cm) in Tris-acetate buffer (0.04M Tris-acetate, 0.1 mM EDTA, pH 8.0) containing 0.25 ug/ml ethidium bromide. Gels were electrophoresed for 17 hours at 70 volts and DNA fragments detected with UV light (306 nm). Gels were photographed using a Kodak Wratten 23A filter and Polaroid type 55 positive/negative film.

SDS-POLYACRYLAMIDE GEL ELECTROPHORESIS

Structural proteins of virions released from occlusion bodies by alkali treatment were compared by electrophoresis in discontinuous polyacrylamide slab gels according to the method of Laemmli (1970, Nature 227:680). Virion proteins were solubilized by boiling for 3 minutes in denaturation buffer (62.2 mM Tris-HCl, 2.0% SDS, 20% glycerol, 2.5% dithiothreitol, pH 6.8) at a concentration of 1 mg protein/ml. Electrophoresis was carried out at 30 milliamps for 4.5 hours in a 12% separating gel (10 cm long × 12 cm wide × 1.5 cm thick). Gels were stained with 0.125% Coomassie brilliant blue R-250 following standard protocols (Summers, M. D. and Smith, G. E., 1978, Virology 84:390-402; Monroe, J. E. and McCarthy, W. J., 1984, J. Invert. Path. 43:32-40).

CHARACTERIZATION OF HzSNPV

In VITRO PROPAGATION AND PLAQUE PURIFICATION

The IPLB-HZ1075 insect cell line grew well in TNM-FH medium supplemented with 8% fetal calf serum. Cells remained susceptible to infection by HzSNPV, but infectivity was not 100% under these conditions. The highest levels observed were between 50 and 70% infected cells with maximal titers of 5×10⁶ plaque forming units per ml. The best infections were achieved when cells were allowed to grow at least 24 hours before inoculation with virus. We have since discovered that the addition of 1% bovine serum albumin (BSA) and 2 g/l L-glutamine to the growth medium improves infectivity to about 100%.

Plaques were produced on monolayers of IPLB-HZ1075 cells using the procedures described previously (Fraser, 1982, J. Tis. Cult. Meth. 7:43-46; Fraser and McCarthy, 1984, J. Invert. Path. 43:427-429). No FP-like plaques (few polyhedra) were observed in this study. All plaques picked for isolation exhibited the wild-type morphology and produced many occlusion bodies per infected cell.

LARVAL INFECTIONS WITH OCCLUSION BODIES

The plaque-purified strains were amplified in third to fourth instar H. zea larvae. Larval propagation was necessary to rapidly expand the virus and reduce the probability of selecting in vitro passage mutants.

Mutant selection is a phenomenon which occurs readily during in vitro propagation of baculoviruses (Potter, K. N., et al., 1976, J. Virol. 18:1040-1050; Hink and Strauss, 1976, J. Invert. Path. 27:49-55; Fraser and Hink, 1982, Virology 117:366-378; Fraser and McCarthy, 1984, J. Invert. Path. 43:427-429), but is not observed during short term in vivo propagations of HzSNPV (McIntosh, A. H. and Ignoffo, C. M., 1986, Intervirol. 25:172-176).

To amplify the virus in larvae, the inoculations were performed by placing a drop of a 1×10⁶ OB/ml suspension directly on the head capsule of each larvae. Larval derived OBs were used for subsequent inoculations to characterize the relative virulence and degree of pathogenicity of each strain and the wild-type isolate.

During these in vivo amplifications, we noted differences in the gross pathology of several plaque-purified strains relative to the pathology of the wild-type isolate. Many of the plaque-purified strains caused rapid melanization and instability of the cuticle upon death of the larvae, a pathology normally seen following infection with HzSNPV. In contrast, several strains caused mortality without the usual attendant rapid melanization and cuticular breakdown.

The plaque-purified virus strains could be separated into three groups based on their relative ability to cause melanization in infected third instar larvae (Table III).

TABLE III

| (Separation of HzSNPV Elcar) Strains on the Basis of Ability to Cause Melanization | |
|---|---|
| Melanization Ability | Isolate |
| Rapid Melanization and Death | W+, 1, 2, 4, 11, 12, 13, 14, 17, 18, 20, 23 |
| Slow Melanization and Death | 5, 7, 8, 9, 21, 22, 24, 25 |
| No Melanization[a] | 15 |

[a] "No Melanization" is defined as less than 30% melanization by nine days after larval death.

The wild-type virus isolate (W+) and several of the plaque-purified strains (1, 2, 4, 11, 12, 13, 14, 17, 18, 20, 23) caused larval death within four to five days post inoculation. The dead larvae rapidly melanized over a period of 1 to 3 hours, turning a dark brown overall, and the cuticle was easily disrupted.

Larvae infected with several other strains (5, 7, 8, 9, 15, 21, 22, 24, 25) also reached apparently complete infection by 4–5 days post inoculation as evidenced by the abundance of occlusion bodies in infected tissues, but the larvae did not die or melanize rapidly. The larvae became soft and incapable of motion in the posterior two-thirds of the body after 4–5 days, but actual death (i.e., unresponsiveness to probing) and subsequent melanization required several more days, and in some cases even weeks, e.g. HzS-15.

Strain HzS-15 caused a similar pathology to the other slow-melanizing strains. However, HzS-15 was remarkable in that most larvae infected with this strain did not begin melanizing until greater than 7 days post inoculation, with many taking several weeks to completely melanize. Furthermore, HzS-15 is highly virulent.

To further characterize these apparent differences in pathology between plaque-purified strains, we standardized the inoculations using a surface treatment bioassay with 20 neonate (24 hour old) larvae per isolate. Two larvae were added to individual 1 ounce plastic portion cups containing an agar based diet (Ignoffo, C. M., 1963, Ann. Entom. Assoc. Am. 56:178–182) surface treated with 100 μl of a $1 \times 10^7$ OB/ml suspension (1250 OB$mm^2$). All infected larvae died within 4 days post infection at this dosage. Larvae were monitored daily for mortality (as measured by unresponsiveness to probing) and melanization (as measured by coloration and cuticular disruption upon prodding).

Three groupings were generated based upon relative percentages of larvae melanizing within a given time period (Table IV), essentially confirming the earlier observations (Table III).

TABLE IV
PERCENT OF LARVAE MELANIZING OVER TIME

| Melanization Rate | Strain | Days After Larval Death | | | |
|---|---|---|---|---|---|
| | | 0-1 | 2-3 | 4-9 | 9 |
| | w+ | 75 | 25 | — | — |
| | 1 | 80 | 20 | — | — |
| | 2 | 81 | 19 | — | — |
| | 4 | 95 | 5 | — | — |
| | 11 | 80 | 20 | — | — |
| rapid melanization[a] | 12 | 78 | 17 | 5 | — |
| | 13 | 94 | 6 | — | — |
| | 14 | 94 | 6 | — | — |
| | 17 | 88 | 12 | — | — |
| | 18 | 93 | 7 | — | — |
| | 20 | 100 | — | — | — |
| | 23 | 85 | 5 | 5 | 5 |
| | 5 | 6 | 0 | 26 | 67 |
| | 7 | 10 | 20 | 20 | 50 |
| | 8 | 5 | 5 | 37 | 53 |
| slow melanization[b] | 9 | 19 | 6 | 31 | 56 |
| | 21 | 69 | 12 | 13 | 6 |
| | 22 | 44 | 19 | 19 | 18 |
| | 24 | 0 | 7 | 27 | 67 |
| | 25 | 5 | 10 | 35 | 50 |
| non-melanizing[c] | 15 | 5 | 11 | 11 | 73 |

[a]Greater than 90% mortality within 3 days, and at least 75% of the larvae melanized within one day of death.
[b]Greater than 30% of the larvae melanized within 9 days of death.
[c]Less than 30% of the larvae melanized by 9 days after death.

At least 75% of the larvae infected with the rapidly melanizing strains completely melanized within 24 hours of death. The slow melanizing strains produced greater than 30% melanization response within nine days following larval death. Once again, HzS-15 was remarkable, causing less than 30% melanization by nine days post mortality.

RESTRICTION ENZYME DIGESTION PATTERNS OF VIRAL DNAs

The genomes of all twenty strains were compared following digestions with BamHI, EcoRI, HindIII, and PstI. Each strain could be distinguished from all others on the basis of the combined restriction digestion patterns. No single genotype was predominant. For example, in the HindIII digests there were only three strains with identical fragment patterns (FIG. 4). These three strains could be distinguished from the others upon digestion with BamHI. Comparisons of the several individual digests suggested that there is a hypervariable region of the HzSNPV genome between map units 23.5 and 43.3 (Knell and Summers, 1984, J. Gen. Virol. 65:445–450).

Strain HzS-15 was singled out as unique due to its remarkably long melanization period and complex occluded virion structural protein profile. We compared this strain with the wild-type isolate using several additional enzymes (FIG. 5). The wild-type virus and HzS-15 exhibited similar restriction patterns with enzymes BamHI, KpnI, and PstI. Different restriction patterns were observed with the enzymes EcoRI, EcoRV, HindIII, and SstI. The differences in EcoRI and SstI banding patterns can be attributed to the hypervariable region identified in the HindIII digests. No conclusions can be drawn about the region of EcoRV variability since no mapping data is available for this enzyme.

Figure 6:
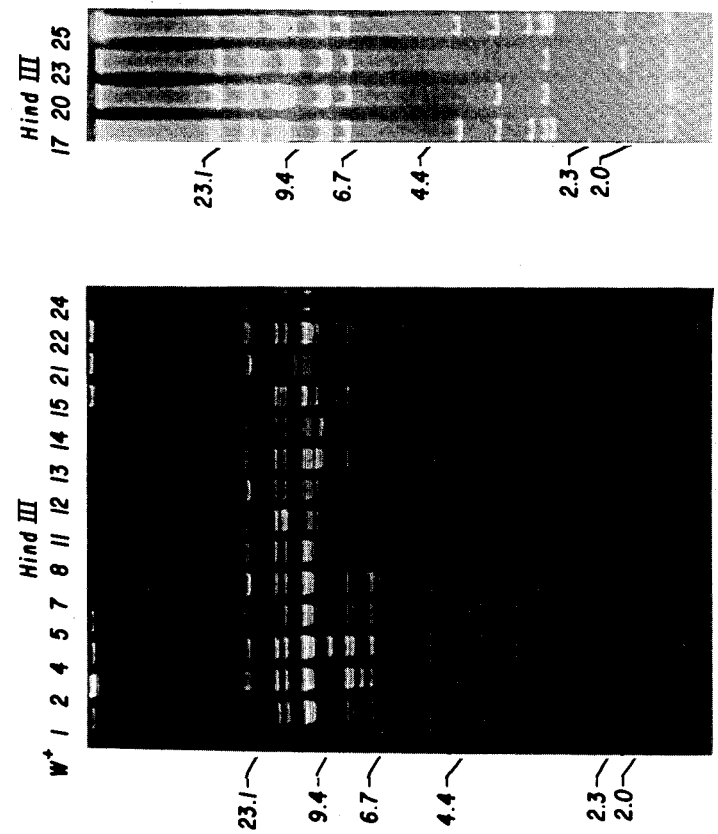
FIG. 6. HindIII restriction endonuclease analysis of HzSNPV Elcar TM wild-type and plaque purified isolates. Viral DNA was purified from band isolated virions as described in the methods. Viral DNAs were digested with HindIII and fractionated on a 0.75% agarose gel. Most of the differences between the wild-type (W+) and plaque purified (1-25) strains occur between map units 23.5 and 43.3, which correspond to the region between HindIII bands H through G (Knell and Summers, 1984, J. Gen. Virol. 65:445-450).

Since HzS-15 and the wild-type isolate produce similar BamHI restriction patterns, we used the restriction enzyme map of Knell and Summers supra as a reference in constructing a physical map of HzS-15 (FIG. 6). The map of HzS-15 was constructed from analyses of single restriction enzyme digests and double restriction enzyme digests with BamHI, PstI, and SstI (Tables V, VI).

TABLE V
SIZES OF HzS-15 RESTRICTION FRAGMENTS[a]

| Fragment | Enzymes (Single Digestion) | | | | |
|---|---|---|---|---|---|
| | BamHI | EcoRV | HindIII | PstI | SstI |
| A | 36.82 | 14.08 | 25.70 | 39.33 | 28.97 |
| B | 33.61 | 12.93 | 16.27 | 36.72 | 25.66 |
| C | 15.46 | 10.92 | 15.15 | 33.47 | 23.22 |
| D | 13.66 | 9.53 | 14.25 | 11.50 | 19.22 |
| E | 12.62 | 8.94 | 11.35 | 6.26 | 11.59 |
| F | 7.62 | 8.94 | 10.72 | 3.54 | 9.76 |
| G | 4.00 | 8.32 | 10.11 | 0.66 | 9.67 |
| H | 3.96 | 8.32 | 7.82 | | 4.06 |
| I | 1.87 | 7.68 | 7.55 | | |
| J | 1.83 | 6.83 | 3.69 | | |
| K | 1.29 | 6.01 | 2.75 | | |
| L | | 3.90 | 2.60 | | |
| M | | 3.38 | 1.72 | | |
| N | | 3.01 | | | |
| O | | 3.01 | | | |
| P | | 2.84 | | | |
| Q | | 2.66 | | | |
| R | | 1.70 | | | |
| S | | 1.60 | | | |
| T | | 1.60 | | | |
| U | | 1.47 | | | |
| V | | 0.99 | | | |
| W | | 0.92 | | | |
| X | | 0.54 | | | |
| Y | | 0.43 | | | |
| Z | | 0.33 | | | |
| AA | | 0.28 | | | |
| Total | 132.74 | 131.25 | | | |
| 1290 | | | | | |

[a]Sizes are given in kilobase pairs.

TABLE VI

SIZES OF HzS-15 RESTRICTION FRAGMENTS[a]

| Fragment | Enzymes (Double Digestion) | | |
|---|---|---|---|
| | BamHI/PstI | BamHI/SstI | PstI/SstI |
| A | 28.64 | 22.65 | 28.97 |
| B | 25.78 | 15.46 | 25.66 |
| C | 15.46 | 15.20 | 21.76 |
| D | 8.59 | 11.50 | 11.50 |
| E | 7.26 | 11.19 | 11.50 |
| F | 6.56 | 10.36 | 8.00 |
| G | 6.26 | 7.83 | 6.14 |
| H | 5.22 | 7.83 | 5.52 |
| I | 5.12 | 7.62 | 5.42 |
| J | 4.33 | 5.53 | 3.35 |
| K | 4.00 | 4.06 | 2.69 |
| L | 3.96 | 4.06 | 2.09 |
| M | 3.54 | 4.00 | 1.40 |
| N | 3.08 | 3.96 | 1.03 |
| O | 1.87 | 3.40 | 0.66 |
| P | 1.83 | 3.31 | |
| Q | 1.29 | 1.83 | |
| R | 0.99 | 1.45 | |
| S | | 1.29 | |
| T | | 0.45 | |
| V | | | |
| W | | | |
| X | | | |
| Y | | | |
| Z | | | |
| AA | | | |

[a]Sizes are given in kilobase pairs.

Ambiguities in double digestion analyses of the complete viral genome were resolved using double and triple digestions of individual cloned PstI and BamHI fragments.

Several differences were evident between HzS-15 and the wild-type map of Knell and Summers (1984, supra). An additional SstI restriction site present in HzS-15 at map unit 43.9 produced two fragments, B and G, related to the wild-type SstI fragment A. The HzS-15 SstI-A fragment is related to wild-type fragment B. The loss of an SstI restriction site at 93.6 map units of the wild-type map generates a fused fragment, H, in HzS-15 that is related to both SstI-G and -H of the wild-type genome. In addition, the location of wild-type SstI fragments E and F of Knell and Summers (1984, supra) had to be interchanged to correspond with our mapping data.

COMPARISON OF VIRION STRUCTURAL PROTEINS

The varied larval pathology prompted an investigation of potential similarities in structural proteins between strains exhibiting similar pathology.

Figure 7:
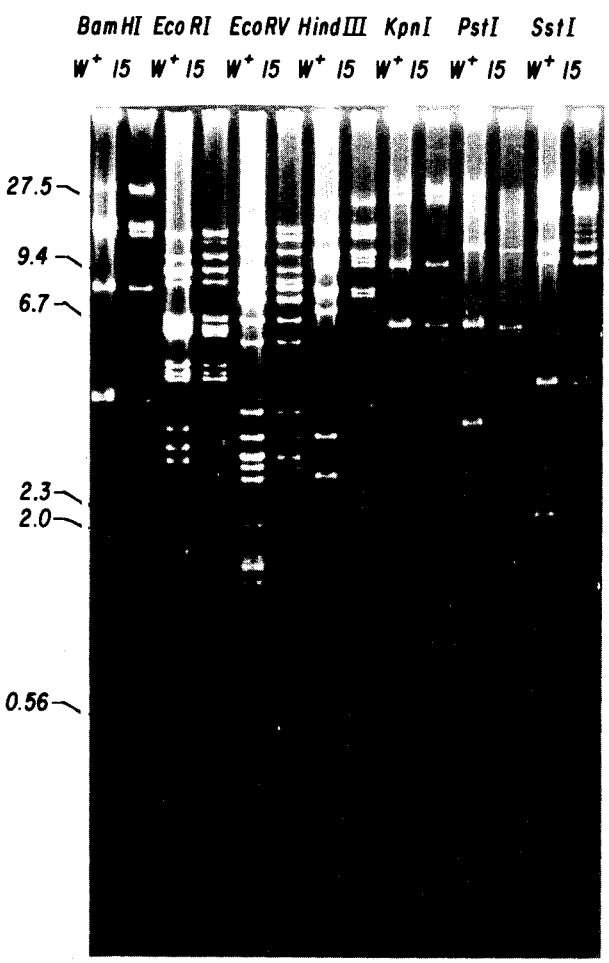
FIG. 7. Comparison of the wild-type Elcar TM isolate and HzS-15 strain with enzymes BamHI, EcoRI, EcoRV, HindIII, KpnI, PstI, and SstI. Wild-type isolate (W+) and the plague-purified HzS-15 strain were digested with restriction enzymes and fractionated on a 0.75% agarose gel. The banding patterns for BamHI, KpnI, and PstI are identical, while those of EcoRI, EcoRV, HindIII, and SstI are different. Many of the differences in the enzyme banding patterns of the two isolates could be localized to map units 23.5 through 43.3. The differences in the banding patterns for the enzyme EcoRV could not be positioned because no restriction maps exist for this enzyme.

Virions were liberated from larval-derived occlusion bodies by alkali treatment and purified by banding in linear sucrose gradients. Electrophoresis of occluded virion structural proteins of the wild-type isolate revealed 13 major polypeptides following staining with Coomassie blue R-250. These proteins ranged in size from 69.9 to 17.8 kilodaltons (FIG. 7). Five of these polypeptides (VP 32.1, VP 37.2, VP 41.1, VP 49.2, and VP 62.9) were found in the occluded virion protein profiles of all the plaque-purified strains. The remaining eight wild-type polypeptides varied in occurrence among the plaque-purified strains.

The total number of major polypeptides in the plaque-purified strains varied from a low of 13 to a high of 19, and ranged in size from 17.8 to 84.1 kilodaltons. VP 46.6 was easily visible in profiles of all the plaque-purified strains, but was not apparent in the profile of the wild-type isolate. Other unusual polypeptides were VP 62.0, found only in HzS-21, and several proteins between 21.1 and 25.7 kilodaltons which were evident only in strains 18 through 25.

The HzS-15 strain exhibited most of the wild-type polypeptides except VP 33.8 and VP 66.1, and also exhibited many of the additional polypeptides found individually in several of the other strains. Several protein bands were apparently unique to HzS-15 including VP 51., and three bands above VP 69.0.

There was no apparent correlation between any of the occluded virion structural proteins and the observed differences in rate of melanization of infected larvae.

EXAMPLE: CELL LINE HOSTS FOR USE IN GENERATION OF RECOMBINANT OCCLUSION BODIES

A *Heliothis zea* derived cell line, IPLB-HZ1075, was subcloned by dilution plating. Twenty-four isolates, (HZ1075/UND-A through X), were originally identified. Many of the isolates with highly vacuolated cells eventually died during subcloning and amplification. Surviving isolates were characterized as to predominant morphology, cell doubling time, and ability to produce both ECV and OBs when infected with HzSNPV. Confirmation of the cell isolates' origin was made by isozyme analysis of the isolates, parental IPLB-HZ1075 cell line and *H. zea* larvae using the enzymes FUM, LDH and MDH. A comparison of invertebrate cel lines in our laboratory by isozyme analysis proved that all were separable using the enzymes LDH and MDH.

MATERIALS AND METHODS

CLONING OF CELL STRAINS

The IPLB-HZ1075 cell line was obtained from Dr. J. Vaughn (USDA Invertebrate Pathology Laboratory, Beltsville) and adapted to growth in TNM-FH medium over several passages. Cloning of cell strains was accomplished by diluting cells to an average density of 1 cell per 100 µl, and plating 100 µl in each well of a 96 well culture plate. The wells were examined after 12 hours and those containing only one cell each were marked. The growth medium for cell clones was composed of an equal mixture of filter-sterilized, conditioned TNM-FH medium and fresh TNM-FH medium (50% conditioned medium). The conditioned medium was obtained from 24 hour old, actively growing cultures of IPLB-HZ1075 cells, and was filter-sterilized to insure no carryover of cells. The strains were maintained in the 96 well plates by replenishing the 50% conditioned medium every 5 days until crowding forced subculturing into 24 well plates.

The cell strains were designated HZ1075/UND-A through X. A total of 24 strains were originally isolated but many eventually died during amplification and subculturing. Of those that survived, one was lost to contamination after only partial characterization.

CELL GROWTH CURVES

Individual tissue culture flasks (25 cm$^2$) were seeded with $1 \times 10^6$ cells of each strain in 3 ml of TNM-FH. The cells were allowed to attach and enter log phase growth for 24 hours after which an initial cell count was made. Three defined regions on the flask were counted at 48 hour intervals for up to 8 days following the initial count. Cell clumping was not a problem for most cell strains, and when it did occur, counts were taken on several focal planes.

QUANTITATION OF POLYHEDRA AND INFECTIOUS EXTRACELLULAR VIRUS PRODUCTION

Each strain was inoculated at a density of $1.25 \times 10^5$ cells per well in separate wells of a 24 well cluster plate and the cells were allowed to attach for 24 hours. After the attachment period the medium was replaced with 100 ul of virus inoculum containing approximately $0.5 \times 10^4$ plaque forming units of a plaque-purified strain of HzSNPV (HzS-15). One hour was allowed for adsorption of the virus, after which the inoculum was replaced with 1 ml of fresh TNM-FH medium. The cells were monitored for 10 days, after which both the media and cells were collected for quantitation of ECV and OBs.

At 10 days post-inoculation, the cultures were collected and the cells and OBs were pelleted by centrifugation at $15,000 \times g$ for 2 minutes. The ECV-containing supernatants were decanted and titered using the 50% tissue culture infective dose (TCID50) method (Yamada et al., 1982, J. Invert. Path. 39:185-191) in Tarasaki microtiter plates (Lux)). Tenfold serial dilutions of infectious cell culture supernatants were combined with an equal volume of HZ1075/UND-K cells at a density of $5 \times 10^5$ cells per ml, and 100 µl of each dilution mix was aliquoted to each of ten wells in the Tarasaki plates. Wells were scored five days post infection for the presence of OBs in cell nuclei, and the TCID50 was calculated according to Reed and Meunch (1938, Amer. J. Hyg. 27:493-497).

The OBs were released from the infected cells by resuspending the pellets from each well in 1 ml of TE buffer (0.01M Tris-HCl, 0.001M EDTA, pH 7.5) containing 0.1% SDS.

The OBs were pelleted from the cell lysate at $15,000 \times g$ for 5 minutes, washed once with TE buffer, and resuspended in a final volume of 250 µl TE. The average number of OBs per ml of the starting cell culture was calculated from three independent direct hemocytometer counts.

ISOZYME ANALYSIS OF CELL ISOLATES

Monolayers of cells (25 cm$^2$) were collected and pelleted at $1800 \times g$ for 10 minutes. The media was decanted and the cells resuspended in lysis buffer (lysis buffer=0.0152M Tris, 0.046M citric acid, 10% sucrose, 1% Triton X-100, 0.02 mM bromophenol blue). The cells were broken by freezing (at $-70°$ C.) and thawing (at 37° C.) three times, and the cell lysates were cleared by centrifugation at $15,000 \times g$ for 3 minutes. Cleared supernatants could be stored at $-70°$ C. for prolonged periods without noticeable alteration of enzymatic activity.

Isozymes were detected following electrophoresis of the cleared cell lysates in 5% polyacrylamide gels in either TBE buffer (81.2 mM Tris, 20 mM boric acid, 1.5 mM EDTA, pH 8.9) for enzymes esterase (EST) and fumarate dehydratase (FUM), or 2×TC buffer (19.4 mM Tris, 4.25 mM citric acid, pH 7.1) for enzymes lactate dehydrogenase (LDH) and malate dehydrogenase (MDH). Vertical slab gels ($20 \times 20$ cm) were run at 350 volts for 2 hours in either TBE buffer or TC buffer, and stained for the respective enzymes following the protocols of Harris and Hopkinson, 1977, Handbook of Enzyme Electrophoresis in Human Genetics. Amsterdam: North Holland Publishing Co., p. 297.

CHARACTERIZATION OF THE CELL LINES

CELL MORPHOLOGY

Twenty-four cell strains labeled HZ1075/UND-A through X were originally isolated by limited dilution plating in 96-well plates. Many of the strains were composed of cells with extensive vacuolation. Most of these highly vacuolated strains eventually died, leaving a total of 13 strains, one of which was eventually lost to contamination.

The twelve surviving strains were fibroblastic in character, and each could be distinguished based upon a predominant cell morphology. Overall morphologies were characterized as predominantly ellipsoidal with 2 or more extensions (UND-B,C,F,H,M,O,R,U) or irregular with several protoplasmic extensions (UND-G,H,L,K,U,V) (Note that the UND-H and UND-U cell populations consisted largely of cells of both morphologies.) All cell strains exhibited mixed morphologies even though each had arisen from a single cell. Strain UND-B had the most uniform morphology with predominantly ellipsoid-shaped cells. Strain UND-G was characterized by extensive cytoplasmic vacuolation.

CELL GROWTH CURVES

Figure 8:
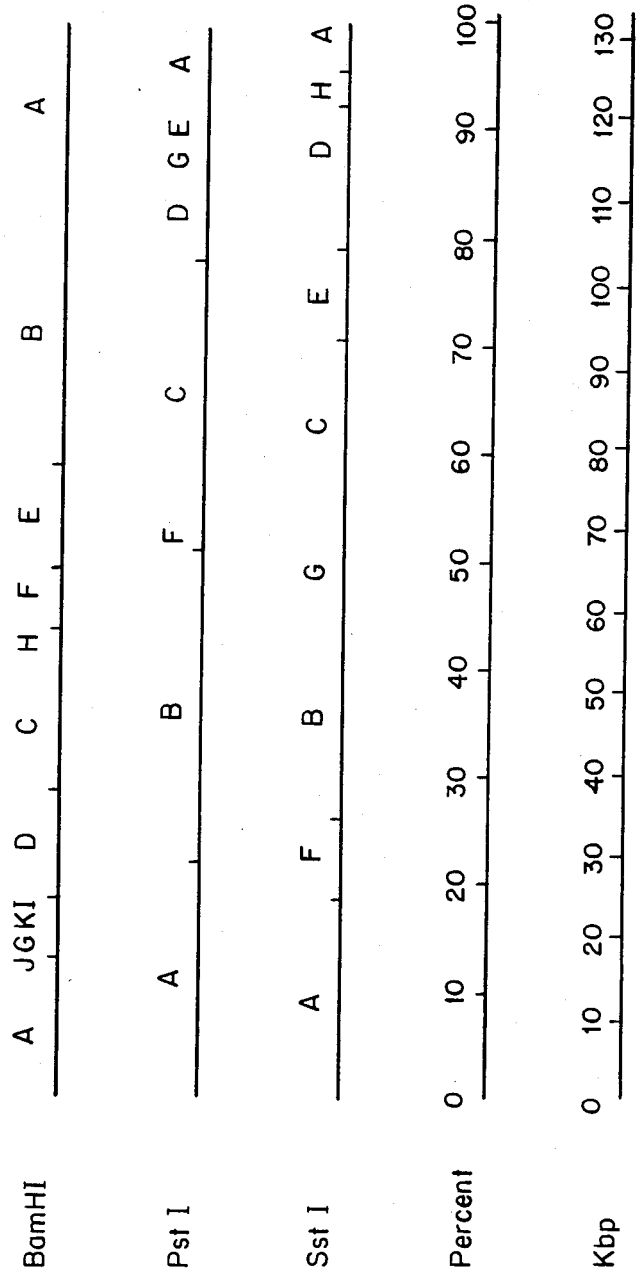
FIG. 8 A linear genomic map of the plague-purified strain, HzS-15. The genomic map was made with virion purified DNA digested either singly or with combinations of BamHI, PstI, and SstI. Any ambiguities in the map were resolved by double digestions of cloned BamHI and PstI fragments. The genomic map of Knell and Summers (1984, J. Gen. Virol. 65:445-450) was used as a reference since the restriction endoncluease banding pattern for BamHI was identical for both isolates.

Cell doubling times for the 12 surviving strains and the parental IPLB-HZ1075 cell line were determined by counting three defined areas of each cell monolayer in 25 cm$^2$ tissue culture flasks at 48 hour intervals. All but two of the cell strains reached stationary growth phase after 96 hours. Strain UND-C entered stationary growth phase by 144 hours, while UND-K exhibited a biphasic growth curve with an apparent primary stationary phase from 96 to 144 hours, and a second growth period between 144 and 196 hours (FIG. 8). The population doubling times were calculated for each strain (Table VII) and ranged from 37.33 hours to 65.48 hours. The majority of cell strains had calculated doubling times between 45 and 60 hours.

TABLE VII

CELL DOUBLING TIMES AND RELATIVE VIRAL PRODUCTION OF CLONED IPLB-HZ1075 CELL STRAINS[1]

| STRAIN | DOUBLING TIME (HRS.) | AVERAGE POLYHEDRAL COUNT (/ML) | TCID$_{50}$ |
|---|---|---|---|
| B | 50.90 | $4.23 \times 10^6$ [c,d] | $6.02 \times 10^4$ |
| C | 48.30 | $5.09 \times 10^6$ [c] | $2.86 \times 10^4$ |
| F | 59.19 | $1.37 \times 10^6$ [f,g] | $4.47 \times 10^3$ |
| G | 52.16 | $9.29 \times 10^6$ [a] | $1.09 \times 10^4$ |
| H | 37.33 | $1.36 \times 10^6$ [f,g] | $1.00 \times 10^3$ |
| K | 46.65 | $9.74 \times 10^6$ [k] | $1.69 \times 10^4$ |
| L | 65.48 | $3.76 \times 10^6$ [d,e] | $7.36 \times 10^3$ |
| M | 39.02 | $6.61 \times 10^6$ [b] | $8.48 \times 10^3$ |
| O | 64.57 | $2.42 \times 10^6$ [e,f] | $1.82 \times 10^4$ |
| R | 41.08 | $5.08 \times 10^6$ [c] | $4.47 \times 10^4$ |
| U | 51.94 | $1.06 \times 10^6$ [g] | $1.09 \times 10^3$ |
| V | 59.82 | $2.62 \times 10^6$ [e] | $6.02 \times 10^3$ |
| HZ1075 | 63.15 | $3.42 \times 10^6$ [d,e] | $1.00 \times 10^3$ |

[1]Cell doubling times and relative viral production of cloned IPLB-HZ1075 cell strains. Doubling times for each cell strain were calculated using the cell growth curves of FIG. 8. Doubling times varied from a low of 37.33 hours in strain UND-H to a high of 65.48 hours in strain UND-L. The average doubling time was 51.37 hours. Duncan's multiple range analysis was used to determine significant differences in OB production. The average number of OBs presented for each cell strain represents three hemocytometer counts. Cell strains with the same superscript letter are not significantly different.

SUSCEPTIBILITY TO HzSNPV

The relative susceptibility of each cell strain to a plaque-purified HzS-15 strain of HzSNPV was gauged by determining the total number of OBs produced and the total infectious ECV released by 10 days post infection. The relative number of OBs produced by 10 days post infection in each strain varied from $1.06 \times 10^6$ per ml (UND-U) to $9.74 \times 10^6$ per ml (UND-K). Duncan's multiple range analysis showed that the average OB counts can be separated into seven statistically related groups (Table VII). The $TCID_{50}$ values ranged from $1.0 \times 10^3$ per ml (UND-H) to $6.02 \times 10^4$ per ml (UND-B) (Table VII).

There was no apparent correlation between the ability to produce OBs and high ECV titers. The population doubling times were also unrelated to either ECV or OB production. For example, UND-B, with a population doubling time of 50.9 hours, produced relatively moderate numbers of OBs ($4.23 \times 10^6$ per ml) but released a relatively high titer of ECV ($6.02 \times 10^4$ $TCID_{50}$ per ml). Strain UND-U with a doubling time of 51.94 hours (similar to that of UND-B) produced significantly fewer OBs ($1.06 \times 10^6$ per ml) and released relatively few ECV ($1.09 \times 10^3$ $TCID_{50}$/ml). Finally, UND-G had a doubling time of 52.16 hours (not significantly different from UND-B or -U) and had the second highest level of OB production ($9.29 \times 10^6$ per ml) but only a moderate level of ECV release ($1.09 \times 10^4$ $TCID_{50}$/ml).

ISOZYME ANALYSIS OF CELL STRAINS AND CELL LINES

To confirm the origin of the cloned cell strains, we compared their staining patterns for the isozymes fumarate hydratase (FUM), lactate dehydrogenase (LDH), esterase (EST) (FIG. 9), and malate dehydrogenase (MDH, not shown) with those of both the IPLB-HZ1075 parental cell line and larval tissues from the host of origin, H. zea. The FUM, LDH, and MDH patterns of all the cloned cell strains were identical to those of H. zea larval tissues and the parental IPLB-HZ1075 cell line.

The pattern obtained with esterase staining was particularly complex. While all the cloned strain patterns were similar to the larval and parental cell line patterns, individual differences were apparent between cloned cell strains. This further substantiates the clonal character of these cell strains.

The IPLB-HZ1075 cell line was compared to other lepidopteran and one dipteran cell lines maintained in our laboratory. Cell homogenates were prepared and electrophoresed as described above, and stained for either LDH or MDH (FIG. 10). The Rf values for each of the cell line isozyme bands were calculated using the IPLB-Hz1075 bands as reference (Rf=1.0) and are presented in Table VIII.

TABLE VIII

Rf VALUES OF SEVERAL INSECT CELL LINES FOR LDH AND MDH[a]

| CELL LINE | LDH[b] | MDH[c] | INSECT OF ORIGIN |
|---|---|---|---|
| ACT-10 | 1.03 | 10.0 | AEDES AEGYPTI |
| BTI-EAA | 0.77 | 4.0 | ESTIGMENE ACREA |
| IPLB-HZ1075 | 1.00 | 1.0 | HELIOTHIS ZEA |
| IPLB-SF-21AE | 0.77 | 1.0 | SPODOPTERA FURGIPERDA |
| TN-368 | 0.58 | 1.9 | TRICHOPLUSIA NI |

[a] Cell extracts were electrophoresed in a 5% polyacrylamide gel (95% acrylamide, 5% bis-acrylamide) in TC buffer and stained for LCH or MDH. Rf values were calculated relative to the migration of the IPLB-HZ1075 enzyme.
[b] Lactate Dehydrogenase
[c] Malate Dehydrogenase The pattern obtained for MDH distinguished the IPLB-HZ1075 cell line from all but one (IPLB-SF21AE) of the lepidopteran cell lines, and from the single dipteran cell line originated from Aedes aegypti. Although the Spodoptera frugiperda IPLB-SF21AE cell line was indistinguishable from IPLB-HZ1075 by staining for MDH, it was distinguishable by staining for LDH.

EXAMPLE: LARVAL HOSTS FOR USE IN GENERATION OF RECOMBINANT OCCLUSION BODIES

The subsections below describe a method for growing Heliothis zea larvae in order to mass-culture recombinant viruses made in accordance with the invention. The non-melanizing strains of HzSNPV, such as those described in Section 6, supra, are preferred for use in the larval expression systems of the present invention.

INSECT DIET PREPARATION

This procedure describes the preparation of diet for Trichoplusia ni and Heliothis zea. The diet for Estigmene acrea requires twice the amount of vitamin mix.

| FORMULA | | |
|---|---|---|
|  | Per Liter | Per 500 ml |
| Pinto beans in 90 ml water | 18 g | 9 g |
| Agar (Sigma) | 25 g | 12.5 g |
| Vitamin diet fortification mixture (ICN) | 3.3 g | 1.66 g |
| Casein (Sigma) | 42 g | 21 g |
| Sucrose (ICN) | 42 g | 21 g |
| Wheat Germ (NIC) | 36 g | 18 g |
| Wesson's Salt Mix (ICN) | 12 g | 6 g |
| Alfacel (non-nutritive bulk) | 6 g | 3 g |
| Methyl Paraben in 18 ml 95% ethanol | 1.66 g | 0.83 g |
| Sorbic Acid (Sigma) | 1.66 g | 0.83 g |
| Ascorbic Acid (Sigma) | 5 g | 2.5 g |
| Streptomycin Sulfate (Sigma) | 0.16 g | 0.08 g |

The diet mix is prepared as follows:
1. The methyl paraben is dissolved in alcohol before the procedure is started.
2. Bring 100 ml of water to a boil. While rapidly stirring, slowly add the agar. Rapid stirring is necessary to prevent the agar from clumping. If the agar clumps, it must be broken up with a spatula.
3. Reheat the mix until small bubbles appear on the side of the beaker.
4. Mix the melted agar and the pinto beans using a blender.
5. Mix on high for 1.5 minutes.
6. Add the rest of the components and mix on high for another 1.5 minutes.
7. Dispense the media into the appropriate containers. Allow to cool at room temperature (15–30 minutes).
8. Store the media in the refrigerator in a sealed container until needed.

COLONY MAINTENANCE

The diet prepared as described is dispensed so that each larva receives a minimum of approximately 10 ml.

REARING OF T. NI OR H. ZEA

The rearing conditions for *T. ni* or *H. zea* are: 28°–30° C., relative humidity of 65–70%, and photoperiod of 12 hours (each 24 hours).

Upon pupation, the pupae are combined into a flight cage of one cubic foot size, at 40 pupae/cage. The adult moths are allowed to emerge and feed on a mixture of 250 g sucrose, 25 ml honey, 5 g ascorbic acid, 5 g methyl paraben (dissolved initially in 5 ml 95% ethanol before addition), plus 500 ml distilled $H_2O$ (components are dissolved with moderate heat). The feeding mix is presented to the adult moths in a 15 ml conical centrifuge tube equipped with a cap through which a two inch long dental wick extends, so that the adults can feed on the dental wick. The walls of the flight cage are lined with sterilized paper towels, on which the adult moths lay their eggs. The paper towels containing the eggs are removed from the cage with aseptic precautions and transferred to a plastic box, termed a crisper, in which some of the agar-based diet mixture is present. The larvae emerge from the eggs in the crisper. Since the larvae are positively phototropic, a light is shone at the end of the crisper where the diet mix is located, so that the larvae move toward the diet mix and feed upon it. The feeding of the larvae on the diet mix increases yield of larvae, since the larvae are cannibalistic and would otherwise eat other larvae and unhatched eggs. Because the larvae are cannibalistic, they are segregated within a day after they emerge. This segregation is accomplished by hand, using an artist's brush which has been sterilized in 0.25% Clorox TM, and rinsed with double distilled $H_2O$. The brush is used to gently lift the larvae and place each individual larva alone into a cup. The larvae are allowed to grow in the cups until pupation, at which time the pupae are placed into the flight cages.

Since *T. ni* are not as cannibalistic as *H. zea*, a slightly different protocol is alternatively used. After *T. ni* eggs are laid upon the paper towels, a one inch square piece of the paper towel is placed on the lid of a quart cup (J. Cup, Dart Container Corp., Mason, Michigan, Cat. No. 8SJ20) containing 20–30 ml of liquid agar-based diet mixture that has solidified. The cup is inverted on top of the paper. The larvae hatch and migrate up toward the diet surface. The paper is then removed from the bottom and the cups are turned right-side up. The larvae are allowed to grow in the cups until pupation, at which time the pupae are placed into the flight cages.

REARING OF G. MELONELLA

The rearing of *G. melonella* largely follows the same protocol as described in Section 9.2.1. *supra* for *T. ni* or *H. zea*, with the following differences:

No photoperiod is necessary for *G. melonella* growth. The temperature can range from 25° to 30° C. The relative humidity of ambient room conditions is suitable.

The larva diet for *G. melonella* is composed of a mixture of 200 ml honey, 100 ml glycerine, and 1 box Gerber TM's mixed cereal. The diet mixture is put into a quart Mason jar fitted with a wire-mesh screen at the top, into which the *G. melonella* eggs are placed. After the larvae emerge, more diet mix is added as necessary until the larvae form cocoons. Since *G. melonella* larvae are not as cannibalistic as *H. zea* larvae, it is not necessary to segregate the larvae. When the larvae are in the last instar stage and start forming cocoons, they are taken out of the jar by hand (with gloves) and placed together in a crisper. The insects pupate and the adults emerge within the crisper. The adult moths lay eggs in the cracks or crevices of the crisper without feeding. Eggs are thus laid at the interface of the lid and the box, so that when the lid is removed, the eggs adhere to the lid. The eggs are then stripped off the lid by using a razor blade, and placed in a Mason jar containing the diet mixture.

GERM-FREE COLONIES

We are engaged in the establishment of insect colonies which are totally germ-free. We have been able to sterilize *H. zea* and *T. ni.* eggs, with egg survival of the sterilization process. The eggs are placed on toweling paper and exposed to peracetic acid for 30 minutes. The eggs are then placed in a sterile environment (an isolater) and rinsed off with sterile water while within the isolater. The eggs thus sterilized give rise to germ-free larvae.

EXAMPLE: HELIOTHIS POLYHEDRIN GENE AND PROMOTER IN AUTOGRAPHA SHUTTLE VECTOR

Figure 13:
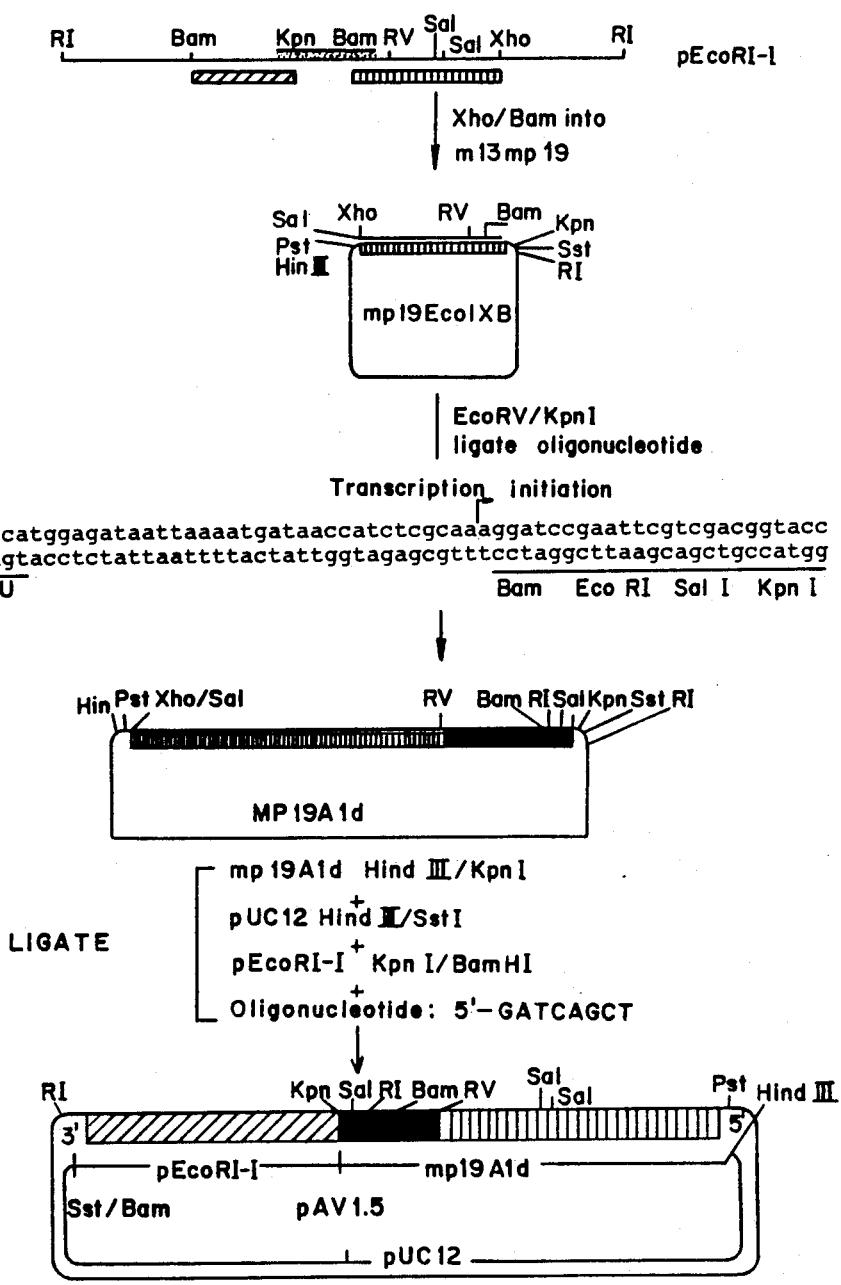
FIG. 13. The construction of cassette vector pAV1.5, which can be used to insert foreign genes within the Autographa polyhedrin sequence which can then be transferred to the Autographa virus genome via in vivo recombination. pAV1.5 can also be used for further genetic manipulations such as insertion of the Heliothis polyhedrin gene, as shown in FIG. 14. The following abbreviations are used in the figure: RI (EcoRI), Sst (SstI), Bam (BamHI), Kpn (KpnI), Sal (SalI), RV (EcoRV), Pst (PstI), H3 (HindIII), and Xho (XhoI).
Figure 14:
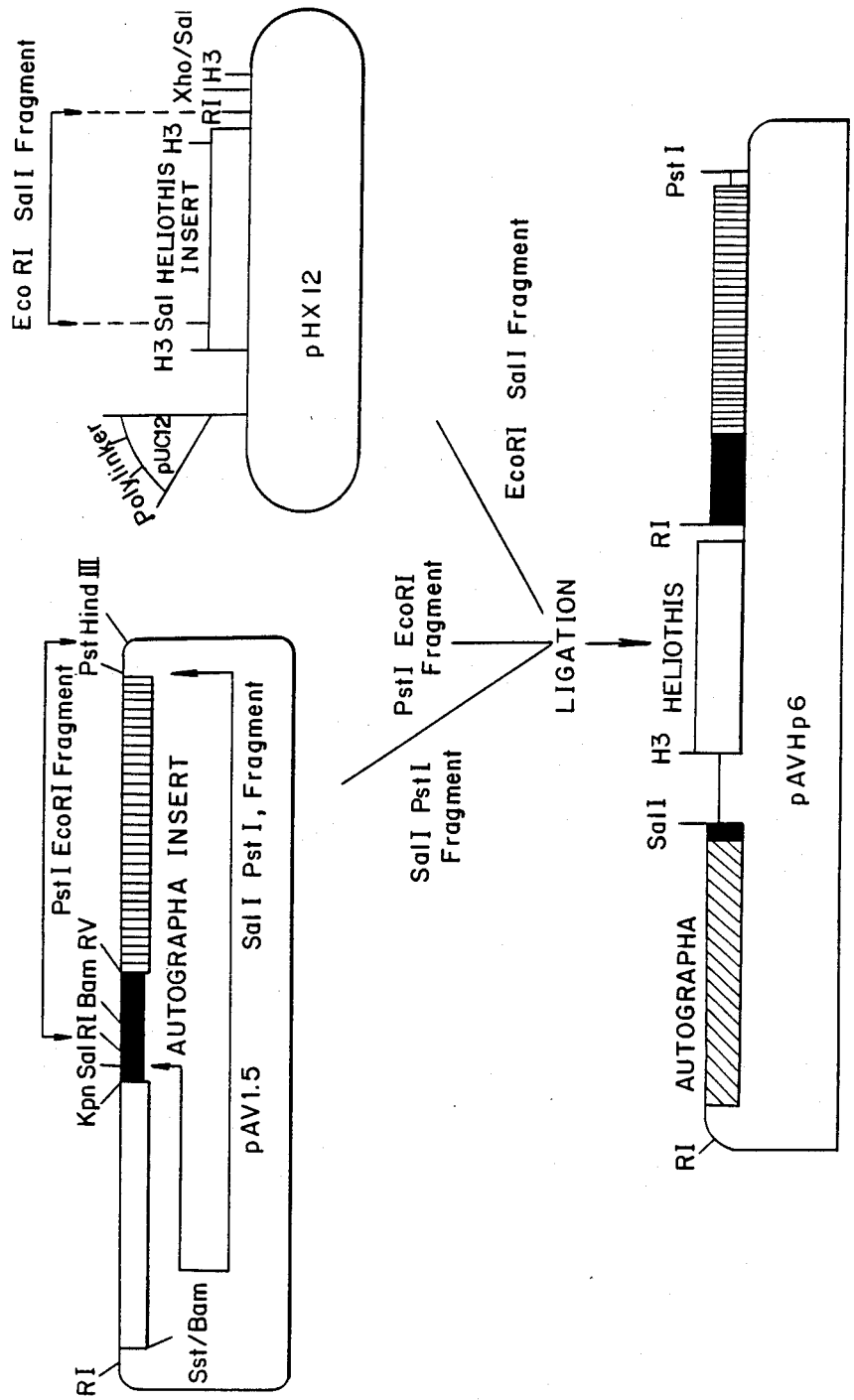
FIG. 14. The construction of cassette vector pAVHp6, which can be used to insert foreign genes within the Heliothis and/or the Autographa polyhedrin genes, and which can be used to transfer such foreign genes into Autographa virus by in vivo recombination. The following abbreviations are used in the figure: Sst (SstI), Bam (BamHI), RI (EcoRI), Kpn (KpnI), Sal (SalI), RV (EcoRV), Pst (PstI), H3 (HindIII), and Xho (XhoI).

Plasmid pEcoRI-I (Adang, M. J. and Miller, L. K., 1982, J. Virol. 44:782–793; Rohel, D. Z., et al., 1983, Virology 124:357–365; Smith, G. E., et al., 1982, J. Virol. 44:199–208), containing the polyhedrin gene of AcNPV, was used as starting material for the construction of an Autographa shuttle vector containing the Heliothis polyhedrin gene and promoter (FIGS. 13, 14). A 2 kb XhoI to BamHI fragment was isolated and subcloned into the SalI and BamHI sites of M13mp19, generating clone mp19pEcoIXB. A DNA fragment was synthesized, corresponding to the Autographa polyhedrin sequence extending from the EcoRV site in the promoter region to the transcription initiation site, followed by a multiple cloning site (MCS) containing BamHI, EcoRI, SalI, and KpnI restriction enzyme recognition sites. Synthesis of the oligonucleotide was by use of an Applied Biosystems Model 380A DNA synthesizer (automated phosphoramidite chemistry). The synthetic fragment was cloned between the EcoRV and KpnI sites of mp19pEcoIXB, resulting in clone mp19AId.

The HindIII to KpnI fragment of mp19AId was isolated. (The XhoI site was lost in the cloning into the SalI site of mp19, and the HindIII site of the mp19 MCS is a convenient nearby site). The KpnI to BamHI fragment of pEcoRI-I was also isolated. These two fragments were cloned into the HindIII and SstI sites of the MCS of pUC12 (FIG. 13). The ligation included a synthetic oligonucleotide, 5'-GATCAGCT-3', in order to permit the ligation of the BamHI end of the pEcoRI-I fragment into an SstI end of pUC12, and to remove the BamHI site probably by the mechanism shown below.

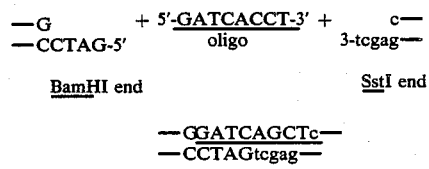

The resulting clone, pAV1.5, included Autographa sequences extending from the XhoI site 5' of the polyhedrin gene to the transcription initiation site, a MCS, and Autographa sequences extending from the KpnI site in the carboxy-coding end of the polyhedrin gene to a BamHI site 3' of the gene. The XhoI and BamHI sites were lost.

Plasmid pAV1.5 and plasmid pHX12 were used as the parental plasmids for the construction shown in FIG. 14. A 2 kb PstI-EcoRI fragment of pAV1.5 (containing the Autographa polyhedrin promoter) and a 4.2 kb SalI-PstI fragment of pAV1.5 (containing pUC12 sequences) were isolated. A 2.2 kb EcoRI-SalI fragment of pHX12 (containing the Heliothis polyhedrin promoter and coding sequences) was isolated, and ligated to the PstI-EcoRI and SalI-PstI pAV1.5-derived fragments. The resulting plasmid, termed pAVHp6, contains the Heliothis polyhedrin promoter and coding sequences, flanked by Autographa polyhedrin sequences including the Autographa polyhedrin promoter. pAVHp6 can thus be used to transfer the Heliothis polyhedrin gene into AcNPV through in vivo recombination, resulting in a recombinant virus that can comprise an expression system in accordance with the present invention. pAVHp6 can also be used to create a recombinant AcNPV with two polyhedrin promoters. One thus has the potential to express two different heterologous genes within the same virus. In addition, if foreign DNA is inserted and expressed under the control of the Autographa promoter in such a recombinant virus, the parental Heliothis polyhedrin promoter and gene can presumably ensure the retention of occlusion body formation.

AUTOGRAPHA SHUTTLE VECTORS ENCODING AN EPITOPE OF THE INFLUENZA HEMAGGLUTININ WITHIN THE POLYHEDRIN GENE

The strategy being used to construct an Autographa shuttle vector containing sequences which encode an epitope of influenza hemagglutinin within a portion of the polyhedrin coding sequences is diagrammed in FIG. 15.

FIG. 15 depicts a strategy for cloning amino acids 98-106 of the influenza hemagglutinin into the amino-terminal coding sequence of the Autographa polyhedrin gene. This strategy can be used to attempt to insert the influenza sequence into the Autographa polyhedrin sequence contained in the M13 derivative mp19EcoIXB (described in Section 10., supra) within the sequence encoding the second amino acid of the polyhedrin protein. An oligonucleotide (termed Rol-1) can be synthesized (Applied Biosystems Model 380A), which is homologous to the region containing the HpaII cleavage site within the codon for amino acid 2. Rol-1 is annealed to mp19EcoIXB single-stranded DNA, which is then cut with HpaII. Annealing of the oligonucleotide creates the requisite double-stranded region for restriction endonuclease cleavage. The linear single-stranded DNA with HpaII-derived ends is isolated by heat denaturation and gel purification. An oligonucleotide corresponding to amino acids 98-106 of influenza hemagglutinin (termed Rol-2) is synthesized. Rol-2 is then annealed to a third synthetic oligonucleotide (Rol-3) which is complementary to Rol-2. In addition, Rol-3 has 5' and 3' termini which extend beyond Rol-2 which are complementary to the HpaII derived ends of the isolated single-stranded phage DNA. Thus the annealed Rol-2/Rol-3 DNA can be ligated to the isolated single-stranded phage DNA, forming a circular DNA molecule.

After transformation of bacterial cells with the ligated complex, the desired transformant can be selected by hydridization to radiolabeled Rol-3 according to the procedure of Benton and Davis (1977, Science 196:180–182). In addition, Rol-3 encodes two restriction sites, MluI and NsiI, which are not found in the parental mp19EcoIXB DNA. Thus, the identity of selected transformants can be confirmed by the presence of MluI and NsiI restriction sites in the phage DNA isolated from transformants.

As an alternative, a similar strategy to that described supra may be used in order to cut the polyhedrin sequence contained within mp19EcoIXB at the BamHI site within the sequence encoding amino acid 58.

EXAMPLE: PRODUCTION OF RECOMBINANT OCCLUSION BODIES EXPOSING AN EPITOPE OF INFLUENZA HEMAGGLUTININ

The subsections below describe manipulations of the polyhedrin gene of *Autographa californica* to form recombinant occlusion bodies that expose antigenic determinants of foreign organisms. The construction of 5 different recombinant polyhedrin genes containing a short DNA sequence encoding an influenza hemaglutinin epitope are described. The five recombinants are named InHem-1, InHem-2, InHem-43, InHem-50, and InHem-43/50, in which "InHem" signifies the influenza hemagglutinin epitope and the numbered suffix indicates the amino acid residue of the baculovirus polyhedrin sequence into which the hemagglutinin epitope was inserted. Three of these genes encode proteins that form recombinant OBs (InHem-1, InHem-43 and In-Hem-50) while the other two do not form lattices. Interestingly, insertion of the hemagglutinin epitope into the polyhedrin variable region around amino acids 38-50 results in cuboidal OBs that do not embed virions.

The immunological data generated demonstrate that the recombinant OBs are antigenic and immunoreact with antibodies specific for the foreign epitope. For example, monoclonal antibodies raised to the authentic influenza hemagglutinin epitope bind to the denatured recombinant polyhedrin proteins in Western blots. Furthermore, these antibodies also interact with non-denatured purified recombinant OBs. The ability of the recombinant OBs to precipitate or capture antibodies to the influenza hemagglutinin epitope suggests that the recombinant structures may be valuable as diagnostic reagents. Additionally, preliminary results with a limited number of animals indicates that one of the recombinants induces an immunogenic response to the hemagglutinin epitope.

CONSTRUCTION OF SHUTTLE VECTORS

Alternations within the polyhedrin gene were introduced into the baculovirus genome by homologous recombinations in vivo following cotransfection of susceptible cells with both viral DNA and transfer plasmids containing the altered gene. The transfer plasmids are bacterial plasmids containing the viral segment surrounding the polyhedrin gene. In particular, a series of transfer vectors that contain 2kb of baculovirus sequences 5' of the polyhedrin gene, the sequence of the altered polyhedrin gene, and approximately 1.5 kb of 3' flanking sequences were used. The long flanking sequences facilitated the transfer of the polyhedrin gene in the transfer plasmid into the viral genome by homologous recombination in vivo.

Since the initial regions chosen for manipulation were contained on a 2 kb fragment extending from an XhoI site upstream of the polyhedrin gene to a BamHI site corresponding to amino acid residue number 58 of the polyhedrin gene, this fragment was subcloned into mp19 (see FIG. 16). As shown in FIG. 16A, the m19 subclone of the Autographa polyhedrin gene, mp19Xho/Bam, described supra, contains a 2kb insert extending from an XhoI site 5′ of the polyhedrin gene. New restriction sites were introduced into the gene by in vitro mutagenesis using the procedures developed by Kunkel, 1985, Proc. Natl. Acad. Sci. 82:488–492. By propagating the mp19 Xho/Bam subclone in a dut⁻-ung⁻ strain in the presence of uridine monophosphate, we isolated uracilcontaining plus-strand DNA. The minus strand was synthesized in vitro in the presence of deoxyribonucleotides and primed with a synthetic oligonucleotide that hybridized to the region to be mutated. The primer contained the appropriate mismatches to introduce the desired mutation. When the double strand was used to transfect dut⁺ung⁺ E. coli, progeny derived from the minus strand were preferentially recovered. The uracil containing plus strand is not efficiently used as a template in a ung⁺dut⁺ strain.

The following procedures were used to introduce the influenza epitope in the modifiable region between amino acids 43 and 50 of the polyhedrin sequence (See FIG. 16A). Using the oligonucleotide Crec5:

5′GGTAGCCTCTTAGATCTCATGTTCGGCG-3′ a GC base pair at nucleotide 127 was changed to a TA base pair. This change introduced a BglII site into the wild type polyhedrin gene sequence. The alteration in the mp19 subclone was transferred into the transfer vector by replacing the Pst/Bam fragment of the transfer vector with the corresponding fragment of the mutated mp19 subclone (Crec5mp19Xho/Bam). The resulting transfer vector, pAV15, contained a new unique BglII site at a position corresponding to amino acid residue number 43 and a naturally occurring BamHI site at a position corresponding to amino acid residue number 58. A synthetic oligonucleotide encoding the influenza epitope followed by the polyhedrin sequence from amino acid residue 50 to 58 was cloned into the BglII/BamHI site of pAV15 (see FIG. 16A). Taking advantage of the degeneracy of the genetic code the oligonucleotide introduced an XbaI site at a position corresponding to amino acid residue number 50 of the polyhedrin sequence. The resulting transfer vector, pAV15Inhem, contained an altered polyhedrin gene coding for a polyhedrin in which amino acid residues between 43 and 50 were replaced with the influenza epitope.

Figure 16B:
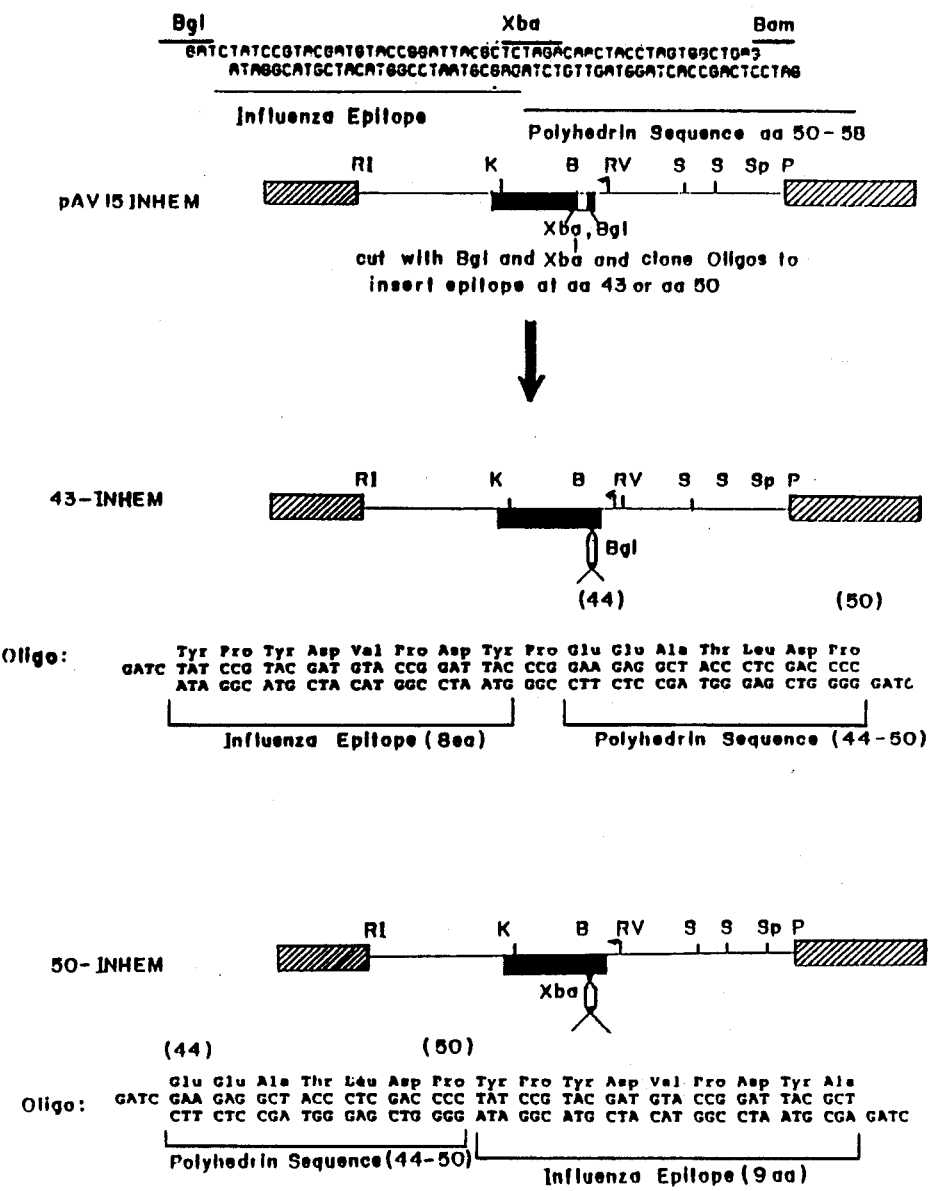
FIG. 16B. The construction of two transfer vectors, pAV15-InHem43 and pAV15InHem-50. These contain the epitope of influenza hemagglutinin at positions 43 and 50, respectively, of the polyhedrin sequence.

By cloning synthetic oligonucleotides between the BglII and XbaI sites of pAV15Inhem, new transfer vectors were constructed coding for polyhedrin products in which amino acids between 43 and 50 (those that were deleted in pAV15Inhem) were reinserted either before or after the influenza epitope (see FIG. 16B). Thus, three transfer vectors were constructed. In the first, pAV15Inhem, the influenza epitope replaced the sequence between amino acids, 43 and 50. In the second, pAVInhem-43, the epitope was inserted at amino acid residue 43 of the polyhedrin sequence. In the third, pAVInhem-50, the epitope was placed at amino acid residue 50. No polyhedrin sequences were deleted from the latter two constructs.

Figure 17B:
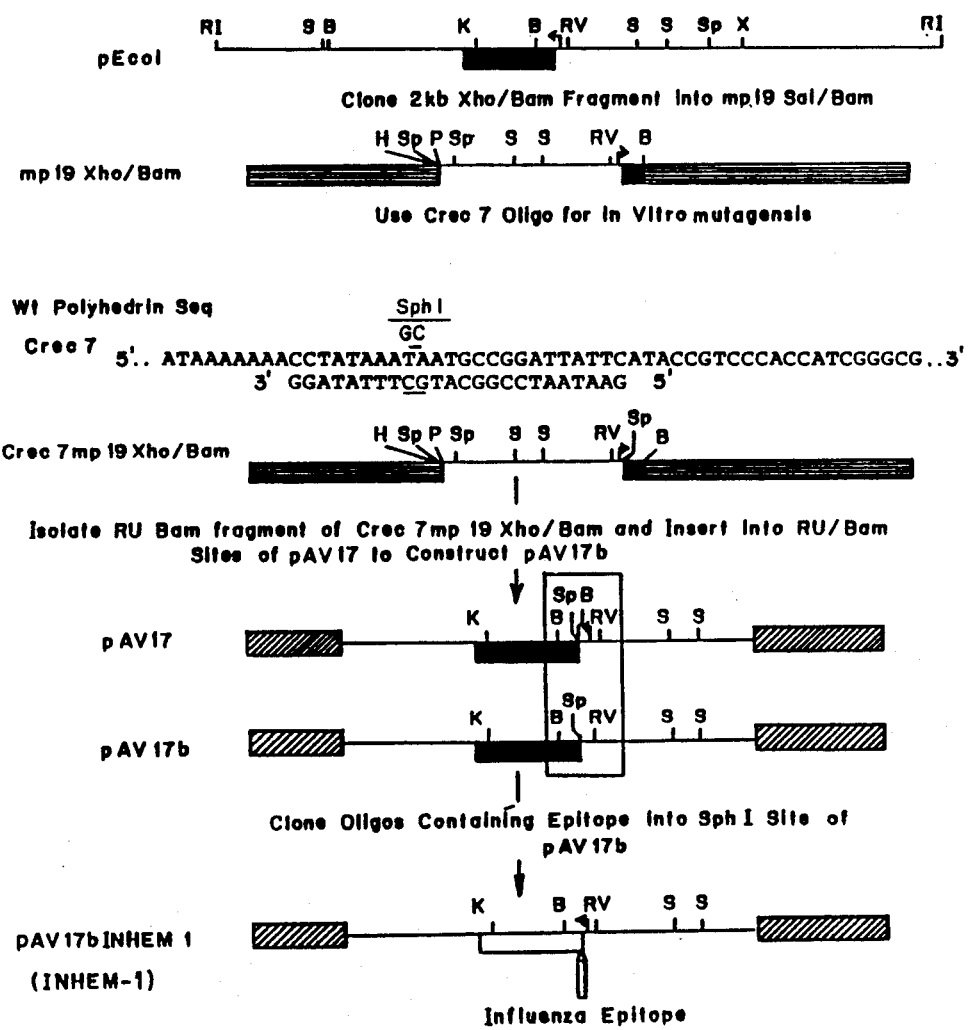

Using similar strategies, a SphI site was introduced at the initiating methionine. The influenza epitope was then inserted after amino acid residue number 1 (pAV17b Inhem-1) as shown in FIG. 17A and FIG. 17B. As shown in FIG. 17A and 17B, pAV1.5 (FIG. 13) was used to construct three intermediate plasmids, pAVII, pAV12 and pAV13; these, in turn, were used to construct pAV17 which has a unique SphI site located at the ATG of the polyhedrin gene (FIG. 17A). Using a synthetic oligonucleotide and the in vitro mutagenesis technique, pAV17 was converted to pAV17b (FIG. 17B) which is characterized by the unique SphI site at the initiating ATG of the polyhedrin gene and a unique BamHI site within the polyhedrin gene (i.e., the BamHI site located at amino acid -8 in pAV17 was eliminated). A synthetic oligonucleotide encoding the influenza hemagglutinin epitope was then cloned into the SphI site of pAV17b resulting in pA117b-InHem-1 (FIG. 17B).

Figure 18:
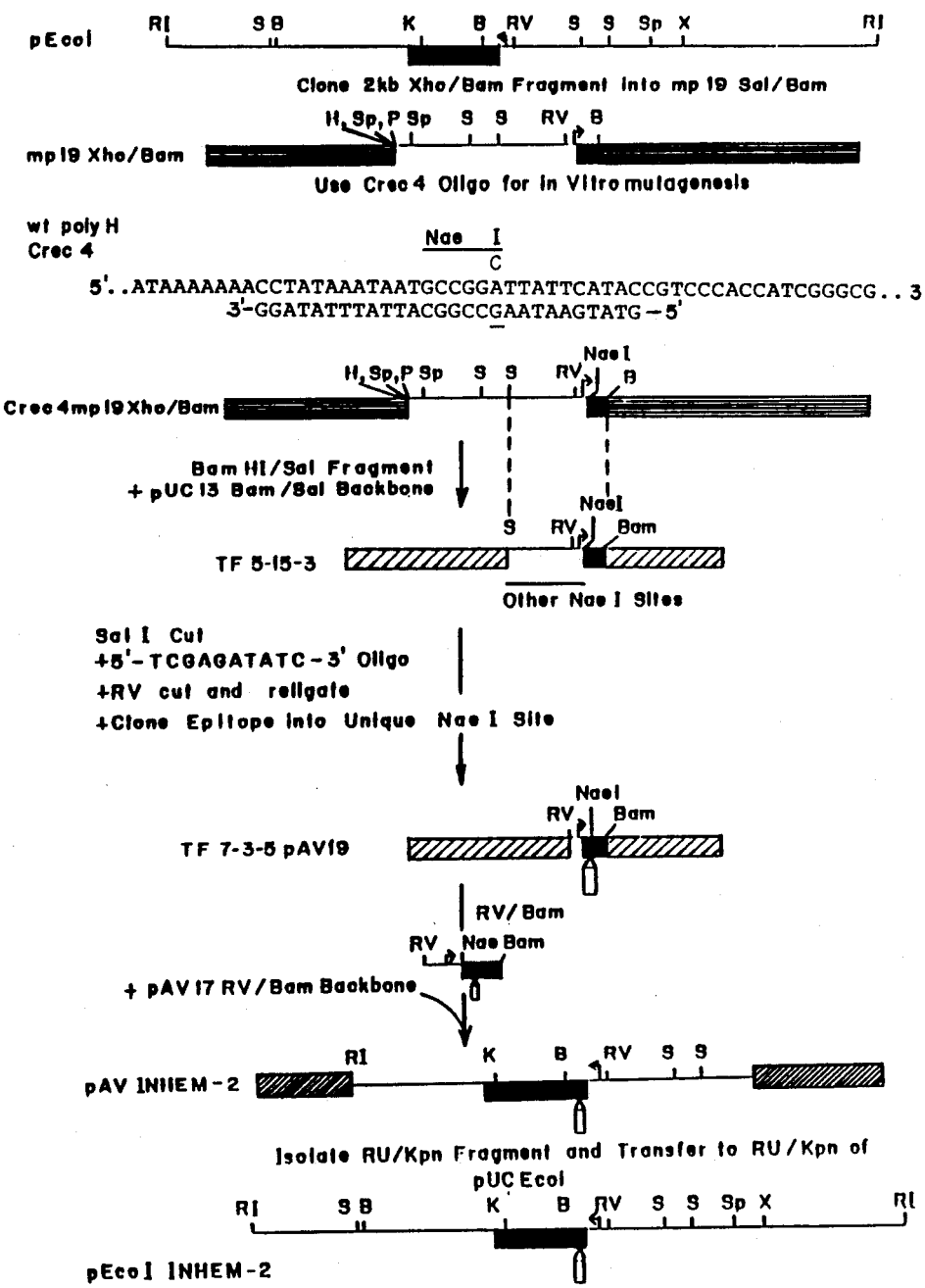
FIG. 18. The construction of vector pAV17b InHem-2 in which the epitope of influenza hemagglutinin is located after amino acid residue number 2 of polyhedrin.

In another set of constructs (see FIG. 18.) a unique NaeI site was introduced within the polyhedrin gene enabling the insertion of the influenza epitope after amino acid residue number 2 (pAV17bInhem-2 as shown in FIG. 18).

A cassette vector was constructed using pBR322 as the plasmid backbone. This vector, called pBRX13, allows for the insertion of the coding sequence for any epitope into the polyhedrin gene spanning the coding region for amino acid residue numbers 36 through 50. Once the recombinant polyhedrin is constructed, the entire polyhedrin gene sequence can be cut out of the pBRX13 vector and cloned into a transfer vector where it is flanked by baculoviral sequences that allow for in vivo recombination with virus.

Figure 19:
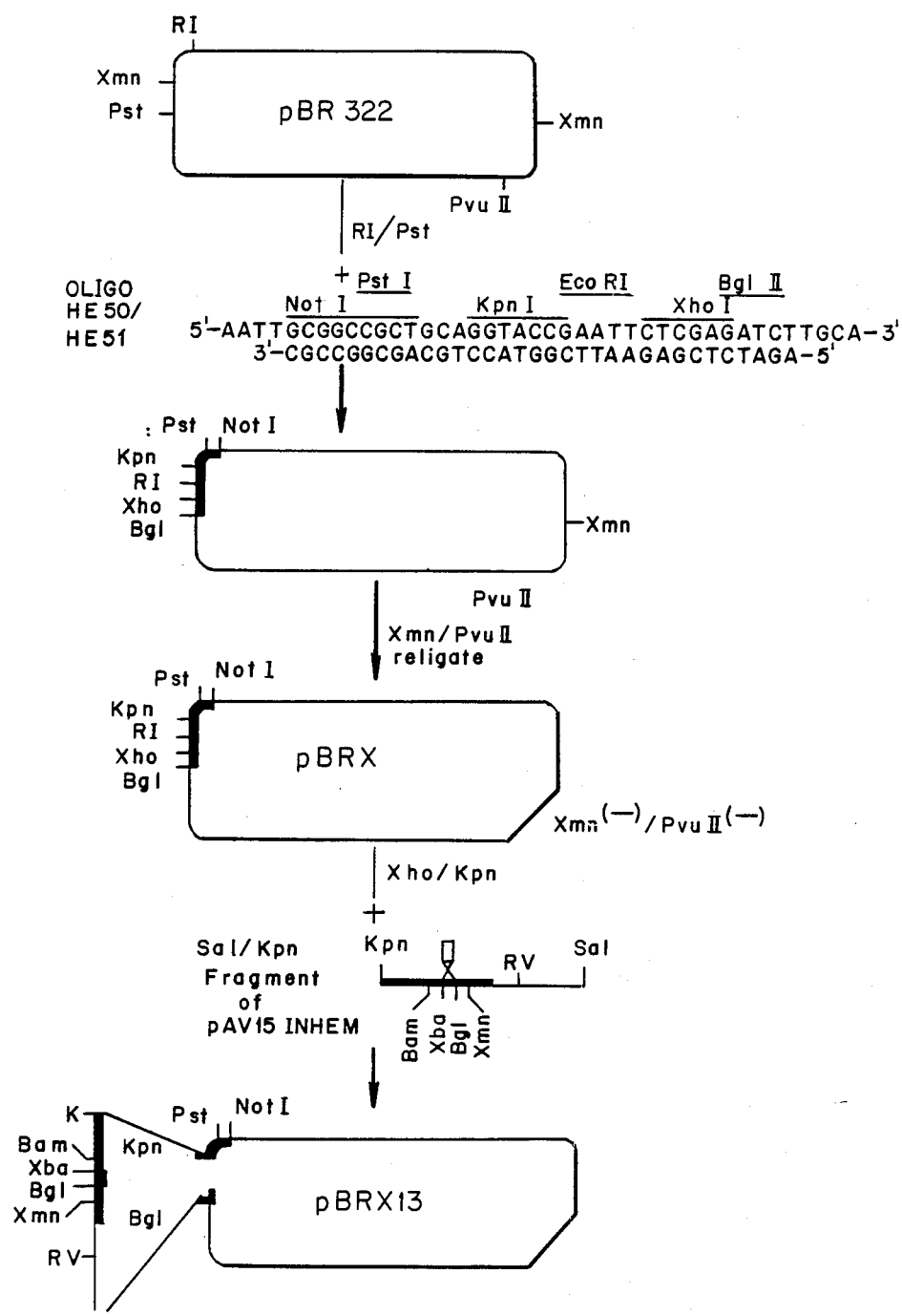
FIG. 19. The construction of pBRX13. This plasmid can be used to insert a coding sequence for any epitope into the polyhedrin gene spanning the coding region for amino acid residues 36–50. The resulting recombinant polyhedrin gene can be excised from pBRX13 and cloned into a transfer vector.

The construction of the pBRX13 vector, illustrated in FIG. 19, was accomplished as follows: pBR322 was cut with EcoRI and PstI and the following oligonucleotide (HE50/HE51) was cloned into the pBR322 backbone so that the EcoRI, PstI and one XmnI site of pBR322 is eliminated and replaced with a unique KpnI and XhoI site:

```
         Pst I                              BglII
  Not I           Kpn I    EcoRII   XhoI
5′-AATTGCGGCCGCTGCAGGTACCGAATTCTCGAGATCTTGCA-3′
3′-CGCCGGCGACGTCCATGGCTTAAGAGCTCTAGA-5′
```

The resulting plasmid, which is now amp$^s$tet$^r$, was cut with XmnI and PvuII and religated in order to eliminate a second XmnI site (and PvuII site) located in the pBR322 backbone. The resulting plasmid was named pBRX. Then the SalI/KpnI fragment of pAV15InHem (which encodes the entire polyhedrin gene containing the influenza hemagglutinin epitope) was cloned into the XhoI/KpnI site of pBRX. The resulting plasmid, pBRX13 contains the first 213 a.a. of the polyhedrin sequence except that the coding region for amino acid residues 43-50 is replaced by the influenza epitope. The polyhedrin sequence of pBRX13 contains a unique XmnI, BglII and XbaI site spanning the amino acid 36-50 region so that the coding sequence for any epitope can be cloned into this region. Once a foreign epitope is cloned into the unique sites, the entire recombinant polyhedrin gene can be excised from pBRX-13 using KpnI and EcoRV. This fragment can then be cloned into a transfer vector so that the recombinant polyhedrin sequence is flanked by baculovirus sequences to allow for in vivo recombination with virus.

PREPARATION OF RECOMBINANT VIRUSES

The transfer of the altered polyhedrin genes into the baculovirus genome was accomplished by homologous recombination in vivo between viral DNA and the transfer plasmids. The viral and plasmid DNAs were introduced into susceptible cells by cotransfection. Transfections involving calcium phosphate precipitation of DNA yielded the most consistent results. Cells were preceded on 60 mm culture dishes in growth media. Calcium phosphate precipitated DNA was added to the media and the cells incubated for 12-18 hours. The media was then removed and fresh media added. The cells were then incubated for 4 or 5 days at which time most cells were infected with virus. Although only a small percentage of the cells are initially transfected, the rest of the cells are infected by the progeny of later rounds of infection.

The progeny of the transfection were plaqued and the recombinant viruses were identified from the parental virus on the basis of plaque morphology. Two types of cotransfections were set up to identify recombinant occlusion body formation. In the first cotransfection, viral DNA was derived from a strain in which the polyhedrin gene had been replaced with the bacterial CAT gene. Since this virus has no polyhedrin gene it fails to make OBs. If the recombinant polyhedrin gene encodes a protein that will form an occlusion body, the recombinant virus is detected in plaque assays among the large number of parental types which fail to make OBs. Since viruses producing occlusion bodies form refractile plaques, these recombinants are easily detected against the OB negative background. The second cotransfection involved the use of wild type viral DNA. In this case, a recombinant failing to make OBs could be detected among the wild type progeny. In this case the rare recombinant forms a non-refractile plaque.

We identified five recombinant viruses: Inhem-1, Inhem-2, Inhem-43 and Inhem-50 containing the altered polyhedrin gene in which the influenza hemaglutinin epitope is inserted after amino acids 1, 2, 43, and 50, respectively. In the polyhedrin gene of the recombinant virus Inhem-43/50, the influenza epitope replaces the polyhedrin sequence between amino acids 43 and 50.

Three of the recombinant viruses encode polyhedrin proteins that form occlusion bodies. Inhem-1 forms OBs that are indistinguishable from wild type by light microscopy. Unlike the irregular occlusions formed by wild type, Inhem-43 and Inhem-50 form large cuboidal occlusions. A clue indicating how the Inhem-43 and Inhem-50 alterations result in the formation of a regular cuboidal lattice was provided by electron micrographs of the recombinant occlusions. Apparently Inhem-43 and Inhem-5 do not embed virions in the OBs. Conceivably the virions embedded in the wild type OB act as impurities and interfere with regular lattice formation. By failing to embed virions these mutants may form large, regular lattices. The other two recombinants, Inhem-2 and Inhem-43/50 did not form occlusion bodies.

IMMUNOLOGICAL ANALYSES OF THE RECOMBINANT OCCLUSION BODIES

The data discussed below indicate that the recombinant OBs described above expose the influenza hemagglutinin epitope as analyzed by ELISA immunoassay, immunoprecipitation and Western immunoblotting. In addition, preliminary results indicate that the recombinant OBs are immunogenic and capable of eliciting an immune response specific for the hemagglutinin epitope.

ELISA ANALYSIS OF SURFACE EXPRESSION OF UNDENATURED INFLUENZA EPITOPE ON RECOMBINANT OCCLUSION BODIES

Plates were coated with 100 µg/ml ACTR (Autographa wild type virus) or 100 µl of recombinant OBs isolated from one T75 flask in 2 ml of TE buffer (43-2B1, 43-2B1A, 50-11A1, 50-1 1B1). After overnight incubation at 4° C., the plates were washed three times with PBS and coated with 1% BSA for 45 minutes at 37° C. 100 µl of anti-influenza hemagglutinin in 2% BSA was added to each well and incubated for 90 minutes at 37° C. After three washes with PBS 100 µl an anti-mouse IgG conjugated to alkaline phosphatase ($10^3$ dilution) in 1% BSA was added to each well. The wells were washed 3 times with PBS after which 100 µl of 0.4 mg/ml p-nitrophenol phosphate in diethanolamine buffer was added to each well and incubated at room temperature for 30 minutes. The plates were read at a wavelength of 405 nm after 30 minutes. The results are shown in Table IX below.

TABLE IX

| ELISA ASSAY FOR PRESENTATION OF INFLUENZA EPITOPE BY RECOMBINANT OCCLUSION BODIES | |
|---|---|
| Recombinant Virus | $A_{405}$ nm |
| ACTR | 0.168 |
| 43-2B1 | 0.864 |
| 43 2B1A | 0.777 |
| 50-1 1A1 | 0.895 |
| 50-1 1B1 | 0.787 |
| TE Buffer | 0.141 |

WESTERN BLOT ANALYSES OF DENATURED RECOMBINANT OCCLUSION BODIES

Western blot analyses indicated that monoclonal antibodies raised to the peptide sequence of the influenza hemagglutinin epitope cross react with the denatured recombinant polyhedrin protein. Proteins from lysates of cells infected with the recombinant viruses were electrophoretically separated in acrylamide gels and blotted onto nitocellulose. Incubation of the blots with a monoclonal antibody (courtesy of Dr. Ian Wilson) raised to the peptide sequence of the epitope indicated that the monoclonal antibody recognized the recombinant polyhedrin but did not recognize wild type polyhedrin.

IMMUNOPRECIPITATION ASSAYS OF RECOMBINANT INFLUENZA/POLYHEDRIN CRYSTALS

Immunoprecipitation data indicate that the anti-influenza hemagglutinin monoclonal antibody (MAb) also interacts with non-denatured recombinant polyhedrin. In these experiments purified occlusion bodies from InHem-43, InHem-50 or ACTR (wild type) infected cells were incubated with either BSA, mouse anti-influenza Mab, or mouse antiplasminogen Mab (as the negative control). The occlusion bodies were pelleted and washed repeatedly. The OBs were then incubated with alkaline phosphatase conjugated rabbit anti-mouse antibody. The OBs were pelleted, washed several times and then incubated with a chromogenic substrate.

The results indicate that the OBs from InHem-43 and InHem-50, but not from ACTR, bound to and precipitated the anti-influenza Mab. These recombinant OBs did not precipitate the anti-plasminogen Mab, indicating that the binding to the anti-influenza epitope represents a specific rather than non-specific interaction. These results indicate that the influenza epitope is exposed on non-denatured recombinant OBs and can be recognized by the antibodies raised to the authentic epitope.

Details of the method and results presented in Table X are described in more detail: 1.3 ml polypropylene tubes were coated for about 1 hour at 37° C. with 1% BSA in PBS. 100 μl of purified polyhedra (1 T75 flask prep in 2 mls TE Buffer) was added to each coated tube and washed 3 times with 1% BSA (centrifuge between washes for 5 minutes). 100 μl anti-influenza hemagglutinin (at about 0.1 mg/ml) in 2% BSA was added to the polyhedra pellet and made up to 0.5 ml with 1% BSA. The samples were incubated at room temperature for about 90 minutes with mixing. The samples were pelleted and washed 3 times with 1% BSA. Anti-mouse IgG conjugated to alkaline phosphatase (100 μl) at $10^3$ dilution in 1% BSA was added and made up to 500 μl with 1% BSA. The samples were incubated at room temperature for 90 minutes. They were then centrifuged and washed 3 times with 1% BSA. 0.5 ml of O-nitrophenol $PO_4$ substrate (0.4 mg/ml) in diethanolamine buffer was added and the samples mixed for 30 minutes at room temperature. They were then centrifuged and the supernatant read at a wavelength of 405 nm.

TABLE X

PRECIPITATION OF INFLUENZA HEMAGGLUTININ MONOCLONAL ANTIBODY WITH RECOMBINANT OCCLUSION BODIES

| Sample | Antibody | $A_{405}$ nm |
|---|---|---|
| 43-2B1 | 1% BSA | 0.001 |
| 43-2B1A | BSA | 0.004 |
| 50-11A1 | BSA | 0.003 |
| 50-11B1 | BSA | 0.002 |
| ACTR | BSA | 0.003 |
| 43-2B1 | anti-inf. hemag. | 1.291 |
| 43-2B1A | anti-inf. hemag. | 1.219 |
| 50-11A1 | anti-inf. hemag. | 0.915 |
| 50-1 1B1 | anti-inf. hemag. | 0.596 |
| ACTR | anti-inf. hemag. | 0.017 |
| 43-2B1 | 28G (Pg antibody) | N.D. |
| 43-2B1A | 28G (Pg antibody) | 0.055 |
| 50-1 1A1 | 28G (Pg antibody) | 0.073 |
| 50-1 1B1 | 28G (Pg antibody) | 0.063 |
| ACTR | 28G (Pg antibody) | 0.064 |

Similar results were obtained for InHem-1.

IMMUNOGENICITY OF THE RECOMBINANT OCCLUSION BODIES

The data in Table XI show results of preliminary studies testing the immunogenicity of the recombinant OBs. In these tests, mice were incoulated with purified OBs from Inhem-43 infected cells. At various times the animals were bled and the sera tested for antibodies specific for the influenza hemagglutinin epitope in ELISA assays. In these assays we looked for the presence of mouse antibodies that would bind to the 9 amino acid peptide fixed to plastic wells. The preliminary results indicate that the recombinant OBs induced an immunogenic response to the influenza peptide. The measurements represent a single animal per time point.

TABLE XI

INDUCTION OF ANTIBODIES SPECIFIC FOR INFLUENZA HEMAGGLUTININ EPITOPE USING RECOMBINANT OBs AS IMMUNOGEN

| | $A_{405}$ nm* | | |
|---|---|---|---|
| | Serum Dilution | | |
| Time | $10^2$ | $2 \times 10^2$ | $5 \times 10^2$ |
| 0 weeks | 0.280 | 0.296 | 0.269 |
| 1 | 0.361 | 0.319 | 0.308 |
| 2 | 0.455 | 0.377 | 0.330 |
| 3 | 0.813 | 0.636 | 0.384 |
| 4 | 0.548 | 0.492 | 0.366 |

*Mab to peptide 1.480

DEPOSIT OF MICROORGANISMS

The following *E. coli* strains carrying the listed plasmids have been deposited with the Agricultural Research Culture Collection (NRRL), Peoria, Ill., and have been assigned the following accession numbers:

| *E. coli* Strain | Plasmid | Accession Number |
|---|---|---|
| K12 (DH5) | pHX12 | NRRL B-18172 |
| K12 (DH5) | pHH5 | NRRL B-18173 |
| K12 (DH5) | pHE2.6 | NRRL B-18174 |
| K12 (DH5) | pHE2.61ac | NRRL B-18175 |
| K12 (DH5) | pAVHp6 | NRRL B-18176 |
| K12 (Dh5 alpha) | pAV15InHem-43 | B-18308 |
| K12 (Dh5 alpha) | paV15InHem-50 | B-18309 |
| K12 (Dh5 alpha) | pAV17bInHem-1 | B-18310 |
| K12 (Dh5 alpha) | pAV17bInHem-2 | B-18311 |
| K12 (Dh5 alpha) | pBRX-13 | B-18312 |

The following *Heliothis zea* cell line and *Heliothis zea* NPV isolate have been deposited with the American Type Culture Collection, Rockville, MD, and have been assigned the listed accession numbers:

| | Accession Number |
|---|---|
| *Heliothis zea* cell line: IPLB-HZ1075/UND-K | ATCC CRL 9281 |
| *Heliothis zea* NPV isolate: HzS-15 | ATCC VR 2156 |

The present invention is not to be limited in scope by the microorganisms and cell line deposited since the deposited embodiment is intended as a single illustration of one aspect of the invention and any microorganisms or viruses which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for purposes of description, and figures which diagrammatically depict DNA sequences are not necessarily drawn to scale.

What is claimed is:

1. A recombinant occlusion body comprising repeating subunits in which each subunit comprises a polyhedrin fusion protein comprising a portion of the polyhedrin protein which participates in crystallization, fused to a foreign amino acid sequence.

2. The recombinant occlusion body according to claim 1 in which the foreign amino acid sequence is related to an epitope of a pathogenic microorganism.

3. The recombinant occlusion body according to claim 2 in which the pathogenic microorganism comprises a virus.

4. The recombinant occlusion body according to claim 3 in which the epitope comprises influenza hemagglutinin.

5. The recombinant occlusion body according to claim 4 in which the epitope comprises amino acids 98-106 of influenza hemagglutinin.

6. The recombinant occlusion body according to claim 3 in which the virus comprises Hepatitis A virus.

7. The recombinant occlusion body according to claim 2 in which the foreign amino acid sequence is exposed on the surface of the occlusion body.

8. The recombinant occlusion body according to claim 1 in which the foreign amino acid sequence comprises an antigenic determinant of a foreign protein.

9. The recombinant occlusion body according to claim 1 in which the foreign amino acid sequence replaces all or a portion of the amino terminus of the polyhedrin protein amino acid sequence.

10. The recombinant occlusion body according to claim 1 in which the foreign amino acid sequence replaces all or a portion of a region homologous to the amino acid sequence substantially as depicted in FIG. 1 from amino acid residue number 37 to 49.

11. The recombinant occlusion body according to claim 5 in which the foreign amino acid sequence replaces all or a portion of a region homologous to the amino acid sequence substantially as depicted in FIG. 1 from amino acid residue number 37 to 49.

12. The recombinant occlusion body according to claim 1 in which the foreign amino acid sequence is inserted after amino acid residue number 1 of the Autographa polyhedrin sequence substantially depicted in FIG. 2.

13. The recombinant occlusion body according to claim 1 in which the foreign amino acid sequence replaces amino acid residue number 43 of the Autographa polyhedrin sequence substantially depicted in FIG. 2.

14. The recombinant occlusion body according to claim 1 in which the foreign amino acid sequence replaces amino acid residue number 50 of the Autographa polyhedrin sequence substantially as depicted in FIG. 2.

15. A polyhedrin fusion protein which is capable of crystallizing with other polyhedrin proteins to form recombinant occlusion bodies, comprising: a portion of the polyhedrin protein which participates in crystallization fused to a foreign amino acid sequence.

16. The recombinant polyhedrin protein of claim 15 in which the foreign amino acid sequence comprises an epitope of a pathogenic microorganism.

17. The recombinant polyhedrin protein of claim 16 in which the pathogenic microorganism comprises a virus.

18. The recombinant polyhedrin protein of claim 17 in which the pathogenic microorganism comprises influenza virus.

19. The recombinant polyhedrin protein of claim 18 in which the foreign amino acid sequence comprises amino acids 98-106 of the influenza hemagglutinin.

20. The recombinant polyhedrin protein of claim 17 in which the pathogenic microorganism comprises Hepatitis A virus.

21. The recombinant polyhedrin protein of claim 15 in which the second amnio acid sequence replaces all or a portion of the amino terminus of the polyhedrin protein.

22. The recombinant polyhedrin protein of claim 15 in which the second amino acid sequence replaces all or a portion of a region homologous to the amino acid sequence substantially as depicted in FIG. 1 from amino acid residue number 37 to 49.

23. The recombinant polyhedrin protein of claim 15 in which the second amino acid sequence comprises an antigenic determinant of a foreign protein.

24. The recombinant polyhedrin protein of claim 15 in which the foreign amino acid sequence is inserted after amino acid residue number 1 of the Autographa polyhedrin sequence substantially as depicted in FIG. 2.

25. The recombinant polyhedrin protein of claim 15 in which the foreign amino acid sequence replaces amino acid residue number 43 of the Autographa polyhedrin sequence substantially as depicted in FIG. 2.

26. The recombinant polyhedrin protein of claim 15 in which the foreign amino acid sequence replaces amino acid residue number 50 of the Autographa polyhedrin sequence substantially as depicted in FIG. 2.

27. A recombinant virus which directs the expression of polyhedrin fusion proteins that crystallize to form recombinant occlusion bodies, comprising:
    (a) a polyhedrin promoter; and
    (b) a nucleotide sequence encoding a polyhedrin fusion protein comprising (i) a first nucleotide sequence encoding a portion of the polyhedrin structural protein that participates in crystallization and (ii) a second nucleotide sequence encoding a foreign protein, in which the first and second nucleotide sequences are in the same translational reading frame uninterrupted by translation termination signals; and
in which the nucleotide sequence encoding the polyhedrin fusion protein is under the control of the polyhedrin promoter so that polyhedrin fusion proteins which crystallize to form recombinant occlusion bodies are produced in a suitable host infected with recombinant virus.

28. The recombinant virus according to claim 27 comprising a baculovirus.

29. The recombinant virus according to claim 28 comprising a nuclear polyhedrosis virus.

30. The recombinant virus according to claim 29 comprising *Autographa californica* nuclear polyhedrosis virus.

31. The recombinant virus according to claim 29 comprising *Heliothis zea* nuclear polyhedrosis virus.

32. The recombinant virus according to claim 28 comprising a granulosis virus.

33. The recombinant virus according to claim 27 in which the foreign peptide comprises an epitope of a pathogenic microorganism.

34. The recombinant virus according to claim 33 in which the pathogenic microorganism comprises a virus.

35. The recombinant virus according to claim 34 in which the epitope is related to an epitope of influenza hemagglutinin.

36. The recombinant virus according to claim 27 in which the nucleotide sequence encoding the foreign peptide replaces all or part of the polyhedrin gene that encodes the amino terminus of the polyhedrin protein.

37. The recombinant virus according to claim 27 in which the nucleotide sequence encoding the foreign peptide replaces all or part of a region of the polyhedrin gene that is homologous to the nucleotide sequence substantially as depicted in FIG. 1 from nucleotide number 142 to 180.

38. The recombinant virus according to claim 27 in which the nucleotide sequence encoding the foreign peptide is inserted after amino acid number 1 of the Autographa polyhedrin gene substantially a depicted in FIG. 2.

39. The recombinant virus according to claim 27 in which the nucleotide sequence encoding the foreign peptide replaces the part of the Autographa polyhedrin gene that encodes amino acid residue number 43 substantially as depicted in FIG. 2.

40. The recombinant virus according to claim 27 in which the nucleotide sequence encoding the foreign peptide replaces the part of the Autographa polyhedrin gene that encodes amino acid residue number 50 substantially as depicted in FIG. 2.

41. A transfer vector encoding a polyhedrin fusion protein that crystallizes to form recombinant occlusion bodies comprising:
   (a) a first nucleotide sequence encoding a portion of the polyhedrin structural protein that participates in crystallization; and
   (b) a second nucleotide sequence encoding a foreign peptide in which the first and second nucleotide sequences are in the same translational reading frame uninterrupted by translation termination signals; and
   (c) baculovirus flanking sequences surrounding the first and second nucleotide sequence so that recombination with baculovirus can occur in vivo.

42. The transfer vector according to claim 41, in which the nucleotide sequence encoding the foreign peptide replaces all or part of the polyhedrin gene that encodes the amino terminus of the polyhedrin protein.

43. The transfer vector according to claim 41, in which the nucleotide sequence encoding the foreign peptide replaces all or part of a region of the polyhedrin gene that is homologous to the nucleotide sequence substantially as depicted in FIG. 1 from nucleotide number 142 to 180.

44. The transfer vector according to claim 41 in which the nucleotide sequence encoding the foreign peptide is inserted after the coding sequence for amino acid number 1 of the Autographa polyhedrin gene substantially as depicted in FIG. 2.

45. The transfer vector according to claim 41 in which the nucleotide sequence encoding the foreign peptide replaces the part of the Autographa polyhedrin gene that encodes amino acid residue number 43 substantially as depicted in FIG. 2.

46. The transfer vector according to claim 41 in which the nucleotide sequence encoding the foreign peptide replaces the part of the Autographa polyhedrin gene that encodes amino acid residue number 50 substantially as depicted in FIG. 2.

47. The transfer vector according to claim 41, comprising pAV15InHem-43, substantially as deposited with the NRRL and assigned accession number B18308.

48. The transfer vector according to claim 41, comprising pAV15InHem-50, substantially as deposited with the NRRL and assigned accession number B18309.

49. The transfer vector according to claim 41, comprising pAV17bInHem-1, substantially as deposited with the NRRL and assigned accession number B18310.

50. The transfer vector according to claim 41, comprising pAV17bInHem-2, substantially as deposited with the NRRL and assigned accession number B18311.

51. A recombinant vector, pBRX13, substantially as deposited with the NRRL and assigned accession number B18312.

* * * * *